(12) United States Patent
Harvey et al.

(10) Patent No.: US 9,790,173 B2
(45) Date of Patent: Oct. 17, 2017

(54) ALPHA-7 NICOTINIC ACETYLCHOLINE RECEPTOR MODULATORS AND USES THEREOF-I

(71) Applicant: MERCK SHARP & DOHME CORP., Rahway, NJ (US)

(72) Inventors: Andrew Harvey, Thebarton (AU); Thomas Avery, Thebarton (AU); Dharam Paul, Thebarton (AU); Justin Ripper, Thebarton (AU); Belinda Huff, Thebarton (AU); Rajinder Singh, Thebarton (AU); Laurent Schaeffer, Illkirch (FR); Christophe Joseph, Illkirch (FR); Christophe Morice, Illkirch (FR); Bruno Giethlen, Illkirch (FR)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/435,814

(22) Filed: Feb. 17, 2017

(65) Prior Publication Data

US 2017/0158628 A1 Jun. 8, 2017

Related U.S. Application Data

(63) Continuation of application No. 14/418,695, filed as application No. PCT/AU2013/000849 on Aug. 1, 2013, now abandoned.

(30) Foreign Application Priority Data

Aug. 1, 2012 (AU) .................... 2012903296
Jan. 18, 2013 (AU) .................... 2013900167

(51) Int. Cl.
  *C07D 261/14* (2006.01)
  *C07C 217/82* (2006.01)
  *C07C 311/30* (2006.01)
  *C07C 311/37* (2006.01)
  *C07D 213/74* (2006.01)
  *C07D 295/135* (2006.01)

(52) U.S. Cl.
  CPC ......... *C07C 311/37* (2013.01); *C07C 217/82* (2013.01); *C07C 311/30* (2013.01); *C07D 213/74* (2013.01); *C07D 261/14* (2013.01); *C07D 295/135* (2013.01)

(58) Field of Classification Search
  CPC ... C07C 311/37; C07C 217/82; C07D 213/74; C07D 216/14
  USPC ....................................... 514/239
  See application file for complete search history.

(56) References Cited

U.S. PATENT DOCUMENTS

| | | | |
|---|---|---|---|
| 6,235,791 B1* | 5/2001 | Breliere ............ | A61K 31/137 514/212.01 |
| 8,642,660 B2* | 2/2014 | Goldfarb ........... | A61K 31/122 514/18.9 |
| 9,062,013 B2* | 6/2015 | Harvey ............. | C07C 233/59 |
| 2002/0032199 A1 | 3/2002 | Poss et al. | |
| 2003/0073849 A1 | 4/2003 | Mattson et al. | |
| 2009/0163545 A1* | 6/2009 | Goldfarb ........... | A61K 31/122 514/312 |

FOREIGN PATENT DOCUMENTS

| | | |
|---|---|---|
| EP | 1930001 | 6/2008 |
| WO | WO9804251 | 2/1998 |
| WO | WO0185701 | 11/2001 |
| WO | WO02079152 | 10/2002 |
| WO | WO2009043784 | 4/2009 |
| WO | WO2010070032 | 6/2010 |
| WO | WO2011019538 | 8/2012 |
| WO | WO2012103583 | 8/2012 |

OTHER PUBLICATIONS

U.S. Appl. No. 14/418,695, filed Jan. 30, 2015.
Dimauro et al, Structural modifications of N-arylamide oxadiazoles: Identification of N-arylpiperidine oxadiazoles as potent and selective agonists of CB2, Bioorganic & Medicinal Chemistry Letters, vol. 18, Issue 15, Aug. 1, 2008, pp. 4267-4274.
Gündisch D, Eibl C. Nicotinic acetylcholine receptor ligands; a patent review (2006-2011). Expert opinion on therapeutic patents. 2011;21(12):1867-1896.
International Search Report and Written Opinion of the International Searching Authority Application No. PCT/AU2013/000849 dated Nov. 1, 2013.

* cited by examiner

*Primary Examiner* — Rita Desai
(74) *Attorney, Agent, or Firm* — Matthew A. Leff; John C. Todaro

(57) ABSTRACT

The present invention relates to chemical compounds of formula (I), with the substituents as described in the specification, useful in the positive modulation of the alpha 7 nicotinic acetylcholine receptor (α7 nAChR). The invention also relates to the use of these compounds in the treatment or prevention of a broad range of diseases in which the positive modulation of α7 nAChR is advantageous, including neurodegenerative and neuropsychiatric diseases and also neuropathic pain and inflammatory diseases.

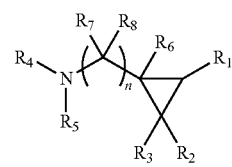

7 Claims, No Drawings

ALPHA-7 NICOTINIC ACETYLCHOLINE RECEPTOR MODULATORS AND USES THEREOF-I

FIELD OF THE INVENTION

The present invention relates to chemical compounds useful in the positive modulation of the alpha 7 nicotinic acetylcholine receptor (α7 nAChR). The invention also relates to the use of these compounds in the treatment or prevention of a broad range of diseases in which the positive modulation of α7 nAChR is advantageous, including neurodegenerative and neuropsychiatric diseases and also neuropathic pain and inflammatory diseases.

BACKGROUND

The α7 nAChRs are rapidly desensitizing ligand-gated ion channels that are abundantly expressed in the cerebral cortex and the hippocampus, a limbic structure intimately linked to attention processing and memory formation. α7 nAChRs modulate neurotransmitter release and are responsible for direct fast excitatory neurotransmission. At the cellular level, activation of α7 nAChRs can regulate interneuron excitability, modulate the release of excitatory and inhibitory neurotransmitters, and contribute to neuroprotective effects.

Several lines of evidence indicate that impaired attention and cognition, which are characteristic of neurological and psychiatric disorders such as Alzheimer's disease (AD), schizophrenia, Parkinson's disease (PD), multiple sclerosis, attention deficit hyperactivity disorder (ADHD), mild cognitive impairment (MCI), age associated memory impairment (AAMI), may involve degeneration or hypo-function of cholinergic input. Moreover, genetic linkage has identified α7 AChRs as a predisposing factor related to sensory gating deficits. Thus, targeting the α7 nAChRs represents a therapeutic strategy for ameliorating cognitive deficits associated with neurodegenerative and neuropsychiatric diseases.

A number of reports also suggest that α7 nAChRs mediate protection against neurotoxicity induced by amyloid beta and excitotoxic insults. Peripherally, α7 nAChRs are expressed in macrophages and their stimulation is essential for inhibiting the release of proinflammatory cytokines (e.g. TNF-α, IL-1) via the cholinergic anti-inflammatory pathway which is triggered in response to signals from the vagus nerve. Thus, the clinical use of positive modulators of the α7 nAChRs could also represent a strategy against inflammatory diseases.

A growing body of evidence indicates the role of the alpha7 nicotinic receptor subtype in neuropathic pain. Both agonists and positive allosteric modulators have been shown to play an important role in chronic inflammatory and neuropathic pain signaling and to attenuate neuropathic pain in preclinical models.

Selective positive allosteric modulation (PAM) of the α7 nAChR is a recently proposed therapeutic approach for treating these disease states. A key advantage of this approach is that modulation only occurs in the presence of endogenous agonist thereby preserving the temporal and spatial integrity of neurotransmission. Several different profiles have been described for PAMs of the α7 nAChR ranging from Type I modulators that predominately affect the peak current and may also increase channel affinity for the agonist, to Type II modulators that affect the peak current, delay the desensitization of the receptor and may reactivate desensitized receptors. Several PAMs have been described in the literature with some Type I examples including 5-Hydroxyindole, NS-1738, Ivermectin, Galantamine and Genistein; Type II examples including PNU-120596, TQS and A-867744 and some intermediate examples being SB-206553 and JNJ-1930942. All PAMs demonstrate enhanced receptor responses to the endogenous ligands acetylcholine and choline, as well as to nicotine and other agonists.

The present invention seeks to address some of the shortcomings of the prior art therapeutics and is directed to a new class of compounds which exhibit positive modulation of α7 nAChR.

SUMMARY OF THE INVENTION

In one aspect the invention provides compounds of formula (I) or salts thereof:

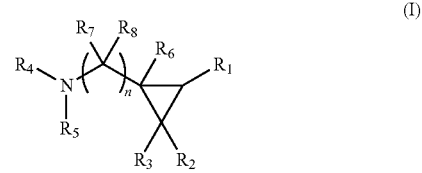

wherein
$R_1$ is selected from optionally substituted aryl, optionally substituted benzyl, optionally substituted heteroaryl, or optionally substituted heterocyclyl;
$R_2$ is selected from hydrogen, $C_1$-$C_4$ alkyl, F, Cl, CN, phenyl or $C_1$-$C_4$ haloalkyl;
$R_3$ is selected from hydrogen, $C_1$-$C_4$ alkyl, F, Cl, CN, or $C_1$-$C_4$ haloalkyl; or
$R_2$ and $R_3$ together form $C_{4-9}$ cycloalkyl or $C_{4-9}$ cycloalkenyl;
$R_4$ is selected from optionally substituted heteroaryl, optionally substituted heterocyclyl, or optionally substituted aryl;
$R_5$ is selected from hydrogen or $C_1$-$C_4$ alkyl;
$R_6$-$R_8$ are independently selected from halogen or hydrogen; and
n is 1-3,
wherein when $R_2$ and $R_3$ are hydrogen, and n is 1, $R_1$ is not (1) phenyl or phenyl substituted with cyclohexyl, heterocyclyl, F or $OCH_3$; or (2) optionally substituted heteroaryl.

In an embodiment $R_1$ is selected from an optionally substituted aryl, optionally substituted heteroaryl, or optionally substituted heterocyclyl.

In an embodiment $R_1$ is an optionally substituted aryl group and more preferably an optionally substituted phenyl group.

Accordingly, in a further aspect the invention provides compounds of formula (Ia) or salts thereof:

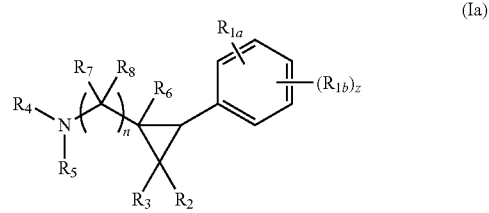

wherein

R$_{1a}$ is selected from the group consisting of optionally substituted lower alkyl, optionally substituted aryl, optionally substituted aryloxy, optionally substituted heteroaryl, optionally substituted heterocyclyl, —P═O(OH)(NH$_2$), —C(O)NR'R', —NR'S(O)$_2$NR'R', —NR'—S(O)$_2$R', —NR'C(O)R', —S(O)$_2$—NR'R' and —NR'R' (where each R' is independently selected from hydrogen, lower alkyl, C$_3$-C$_7$ cycloalkyl, heterocyclyl, heteroaryl, —OH, or NH$_2$), —S(O)R" (where R" is lower alkyl, or cycloalkyl), and —S(O)$_2$R''' (where R''' is lower alkyl, or cycloalkyl);

each R$_{1b}$ is independently selected from the group consisting of cyano, halo, nitro, optionally substituted lower alkyl, optionally substituted aryl, optionally substituted aryloxy, optionally substituted arylalkyl, optionally substituted heteroaryl, optionally substituted heterocyclyl, optionally substituted C$_{3-7}$ cycloalkyl, —P═O(OH)(NH$_2$), —OR, —C(O)R, —C(O)OR, —OC(O)R (where R is selected from hydrogen, optionally substituted alkyl, optionally substituted alkenyl, optionally substituted alkynyl, optionally substituted C$_{3-7}$ cycloalkyl, optionally substituted heterocyclyl, optionally substituted heteroaryl, and optionally substituted aryl), —C(O)NR'R", —NR'C(O)R", —S(O)$_2$—NR'R" and —NR'R" (where R' and R" are independently selected from hydrogen or lower alkyl), —S(O)R''' (where R''' is lower alkyl, or cycloalkyl), —S(O)$_2$R''' (where R''' is lower alkyl, cycloalkyl or OH), or any two adjacent R$_{1b}$ or R$_{1a}$ and R$_{1b}$ together form heterocyclyl or heteroaryl;

z is 0-4;

R$_2$ is selected from hydrogen, C$_1$-C$_4$ alkyl, F, Cl, CN, phenyl or C$_1$-C$_4$ haloalkyl;

R$_3$ is selected from hydrogen, C$_1$-C$_4$ alkyl, F, Cl, CN, or C$_1$-C$_4$ haloalkyl; or R$_2$ and R$_3$ together form C$_4$-C$_9$ cycloalkyl or C$_4$-C$_9$ cycloalkenyl;

R$_4$ is selected from optionally substituted heteroaryl, optionally substituted heterocyclyl, or optionally substituted aryl;

R$_5$ is selected from hydrogen or C$_1$-C$_4$ alkyl;

R$_6$-R$_8$ are independently selected from halogen or hydrogen; and n is 1-3.

In an embodiment z is 1.
In an embodiment z is 2.
In an embodiment z is 0.
In an embodiment z is 0 and R$_{1a}$ is in the para position.

In an embodiment R$_{1a}$ is independently selected from the group consisting of optionally substituted lower alkyl, optionally substituted aryl, optionally substituted aryloxy, optionally substituted heteroaryl, optionally substituted heterocyclyl, —P═O(OH)(NH$_2$), —C(O)NR'R', —NR'S(O)$_2$NR'R', —NR'—S(O)$_2$R', —NR'C(O)R', —S(O)$_2$—NR'R' and —NR'R' (where each R' is independently selected from hydrogen, lower alkyl, C$_3$-C$_7$ cycloalkyl, heterocyclyl, heteroaryl, —OH, NH$_2$), —S(O)R" (where R" is lower alkyl, or cycloalkyl), and —S(O)$_2$R''' (where R''' is lower alkyl, or cycloalkyl).

In another embodiment R$_2$ is C$_1$-C$_3$ alkyl and R$_3$ is C$_1$-C$_3$ alkyl.

In another embodiment R$_3$ and R$_2$ together form a C$_4$-C$_9$ cycloalkyl.

Accordingly, in a further aspect the invention provides compounds of formula (Ib) or salts thereof:

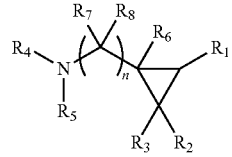

(Ib)

wherein

R$_1$ is selected from optionally substituted aryl, optionally substituted benzyl, optionally substituted heteroaryl or optionally substituted heterocyclyl;

R$_2$ and R$_3$ together form C$_{4-9}$ cycloalkyl;

R$_4$ is selected from optionally substituted heteroaryl, optionally substituted heterocyclyl, or optionally substituted aryl;

R$_5$ is selected from hydrogen or C$_1$-C$_4$ alkyl;

R$_6$-R$_8$ are independently selected from halogen or hydrogen; and n is 1-3.

Accordingly, in a further aspect the invention provides compounds of formula (Ic) or salts thereof:

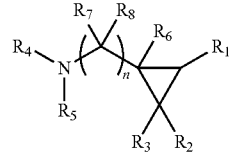

(Ic)

wherein

R$_1$ is selected from optionally substituted aryl, optionally substituted benzyl, optionally substituted heteroaryl or optionally substituted heterocyclyl;

R$_2$ and R$_3$ each independently represent C$_1$-C$_3$ alkyl;

R$_4$ is selected from optionally substituted heteroaryl, optionally substituted heterocyclyl, or optionally substituted aryl;

R$_5$ is selected from hydrogen or C$_1$-C$_4$ alkyl;

R$_6$-R$_8$ are independently selected from halogen or hydrogen; and n is 1-3.

In an embodiment R$_1$ in (Ib) and (Ic) is a phenyl group substituted with R$_{1a}$ wherein R$_{1a}$ is selected from the group consisting of optionally substituted lower alkyl, optionally substituted aryl, optionally substituted aryloxy, optionally substituted heteroaryl, optionally substituted heterocyclyl, —P═O(OH)(NH$_2$), —C(O)NR'R', —NR'S(O)$_2$NR'R', —NR'—S(O)$_2$R', —NR'C(O)R', —S(O)$_2$—NR'R' and —NR'R' (where each R' is independently selected from hydrogen, lower alkyl, C$_3$-C$_7$ cycloalkyl, heterocyclyl, heteroaryl, —OH, or NH$_2$), —S(O)R" (where R" is lower alkyl, or cycloalkyl), or —S(O)$_2$R''' (where R''' is lower alkyl, or cycloalkyl).

In a further aspect the invention provides a method for the treatment or prevention of cognitive deficits associated with neurodegeneration or neuropsychiatric diseases, said method including the step of administering a compound of formula (I), (Ia), (Ib) or (Ic), or a pharmaceutically acceptable salt thereof, or a composition comprising a compound of formula (I), (Ia), (Ib) or (Ic), and related formulae as herein defined or a pharmaceutically acceptable salt thereof.

In still a further aspect the invention provides a method for the treatment or prevention of inflammatory diseases, said method including the step of administering a compound of formula (I), (Ia), (Ib) or (Ic), and related formulae as herein defined or a pharmaceutically acceptable salt thereof, or a composition comprising a compound of formula (I), (Ia), (Ib) or (Ic), and related formulae as herein defined or a pharmaceutically acceptable salt thereof.

In still a further aspect the invention provides a method for the treatment or prevention of neuropathic pain, said method including the step of administering a compound of formula (I), (Ia), (Ib) or (Ic), and related formulae as herein defined or a pharmaceutically acceptable salt thereof, or a composition comprising a compound of formula (I), (Ia), (Ib) or (Ic), and related formulae as herein defined or a pharmaceutically acceptable salt thereof.

In another aspect the invention provides the use of a compound of formula (I), (Ia), (Ib) or (Ic), and related formulae as herein defined or a salt thereof in the manufacture of a medicament for the treatment or prevention of cognitive deficits associated with neurodegeneration or neuropsychiatric diseases.

In another aspect the invention provides the use of a compound of formula (I), (Ia), (Ib) or (Ic), and related formulae as herein defined or a salt thereof in the manufacture of a medicament for the treatment or prevention of inflammatory diseases.

In another aspect the invention provides the use of a compound of formula (I), (Ia), (Ib) or (Ic), and related formulae as herein defined or a salt thereof in the manufacture of a medicament for the treatment or prevention of neuropathic pain.

In another aspect of the invention there is provided a method of positively modulating α7nAChRs in a cell by contacting the cell with a compound of formula (I), (Ia), (Ib) or (Ic), and related formulae as herein defined or a pharmaceutically acceptable salt thereof, to said cell.

In a further aspect of the invention there is provided a pharmaceutical composition for use as a neuroprotective agent, the composition comprising an effective amount of a compound of formula (I), (Ia), (Ib) or (Ic), and related formulae as herein defined or a pharmaceutically acceptable salt thereof and optionally a carrier or diluent.

In still a further aspect of the invention there is provided a pharmaceutical composition for use as an anti-inflammatory agent, the composition comprising an effective amount of a compound of formula (I), (Ia), (Ib) or (Ic), and related formulae as herein defined or a pharmaceutically acceptable salt thereof and optionally a carrier or diluent.

In still a further aspect of the invention there is provided a pharmaceutical composition for treating neuropathic pain, the composition comprising an effective amount of a compound of formula (I), (Ia), (Ib) or (Ic), and related formulae as herein defined or a pharmaceutically acceptable salt thereof and optionally a carrier or diluent.

In another aspect of the invention there is provided a process for the preparation of compounds of formula (I), (Ia), (Ib) or (Ic), and related formulae as herein defined or salts thereof.

DETAILED DESCRIPTION OF THE INVENTION

The term "alkyl" as used alone or in combination herein refers to a straight or branched chain saturated hydrocarbon group. The term "$C_{1-12}$ alkyl" refers to such a group containing from one to twelve carbon atoms and "lower alkyl" refers to $C_{1-6}$ alkyl groups containing from one to six carbon atoms, such as methyl ("Me"), ethyl ("Et"), n-propyl, iso-propyl, n-butyl, isobutyl, sec-butyl, tert-butyl and the like.

The term "cycloalkyl" refers to non-aromatic, saturated non-aromatic carbocycles. The term "$C_{4-9}$ cycloalkyl", for Instance, refers to such a group having from 4 to 9 carbon atoms. Examples include cyclobutyl, cyclopentyl and cyclohexyl.

The term "alkenyl" refers to a straight or branched hydrocarbon containing one or more double bonds, preferably one or two double bonds. The term "$C_{2-12}$ alkenyl", for instance, refers to such a group containing from two to twelve carbon atoms. Examples of alkenyl include allyl, 1-methylvinyl, butenyl, iso-butenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

The term "cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

The term "alkynyl" refers to a straight or branched hydrocarbon containing one or more triple bonds, preferably one or two triple bonds. The term "$C_{2-12}$ alkynyl", for instance, refers to such a group containing from two to twelve carbon atoms. Examples include 2-propynyl and 2- or 3-butynyl.

The term "alkoxy" as used alone or in combination refers to a straight or branched chain alkyl group covalently bound via an oxygen linkage (—O—) and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Preferred aryl groups include phenyl, naphthyl, indenyl, azulenyl, fluorenyl or anthracenyl.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl, benzothienyl, or benzofuranyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

Examples of 5-membered monocyclic heterocyclyl and heteroaryl groups include furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls).

Examples of 6-membered monocyclic heterocyclyl and heteroaryl groups include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl.

Examples of 8, 9 and 10-membered bicyclic heterocyclyl and heteroaryl groups include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazol, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like.

The term "arylalkyl" refers to carbocyclic aromatic rings or ring systems as previously described and substituted by an alkyl group, also as previously described. Unless otherwise indicated the aryl substituent is attached by the alkyl part of the substituent. An example of an arylalkyl group is a benzyl group. Likewise the terms "aryl $C_{1-12}$ alkyl", "aryl $C_{2-12}$ alkenyl" and "aryl $C_{2-12}$ alkynyl" refer to carbocyclic aromatic rings or ring systems as previously described and substituted by a $C_{1-12}$ alkyl, $C_{2-12}$ alkenyl or $C_{2-12}$ alkynyl group, as previously described.

The terms "halo" and "halogen" refers to fluoro, chloro, bromo and iodo groups.

The term "halo alkyl" group has one or more of the hydrogen atoms on an alkyl group replaced with halogens. Notable examples are —$CF_3$ or —$CF_2H$.

The term "aryloxy" refers to an aryl group as earlier described linked to the parent structure via an oxygen linkage (—O—). A notable example is phenoxy. Similarly the term "heteroaryloxy" refers to a heteroaryl group as earlier described linked to the parent structure via an oxygen group. A notable example is a 4, 6 or 7-benzo[b]furanyloxy group.

The term "optionally substituted" means that a group may include one or more substituents. One or more hydrogen atoms on the group may be replaced by substituent groups independently selected from halogens (for example halo alkyl such as —$CF_3$ or —$CF_2H$), $C_{1-6}$ alkyl, $C_{2-8}$ alkenyl, $C_{2-6}$ alkynyl, —$(CH_2)_pC_{3-7}$ cycloalkyl, —$(CH_2)_pC_{4-7}$ cycloalkenyl, —$(CH_2)_p$ aryl, —$(CH_2)_p$ heterocyclyl, —$(CH_2)_p$ heteroaryl, —$C_6H_4S(O)_qC_{1-6}$ alkyl, —$C(Ph)_3$, —CN, —OR, —O—$(CH_2)_{1-6}$—R, —O—$(CH_2)_{1-6}$—OR, —OC(O)R, —C(O)R, —C(O)OR, —OC(O)NR'R", NR'R", —NRC(O)R', —NRC(O)NR'R", —NRC(S)NR'R", —NRS(O)$_2$R', —NRC(O)OR', —C(NR)NR'R", —C(=NOR')R, —C(=NOH)NR'R", —C(O)NR'R", —C(=NCN)—NR'R", —C(=NR)NR'R", —C(=NR')SR", —NR'C(=NCN)SR", —CONRSO$_2$R', —C(S)NR'R", —S(O)$_q$R, —SO$_2$NR'R", —SO$_2$NRC(O)R', —OS(O)$_2$R, —PO(OR)$_2$ and —NO$_2$;

where p is 0-6, q is 0-2 and each R, R' and R" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —CO$_2$H, CF$_3$, CN, phenyl, NH$_2$ and —NO$_2$; or when R' and R" are attached to the same nitrogen atom, they may, together with the atom to which they are attached, form a 6 to 7 membered nitrogen containing heterocyclic ring.

A list of preferred optional substituents includes: halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —CF$_3$), $C_{1-6}$ haloalkoxy (such as —OCF$_3$), —OH, phenyl, benzyl, phenoxy, benzyloxy, benzoyl, —NH$_2$, alkyl, —N(C$_{1-4}$ alkyl)$_2$, —CN, —NO$_2$, mercapto, —P=O(OH)(NH$_2$), —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

Unless otherwise defined and only in respect of the ring atoms of non-aromatic carbocyclic or heterocyclic compounds, the ring atoms of such compounds may also be optionally substituted with one or two =O groups, instead of or in addition to the above described optional substituents.

When the optional substituent is or contains an alkyl, alkenyl, alkynyl, cycloalkyl, aryl, heteroaryl or heterocyclyl group, the group may itself be optionally substituted with one to six of the same or different substituents selected from halogen, $C_{1-6}$ alkyl, $C_{1-6}$ alkoxy, $C_{2-6}$ alkenyl, $C_{2-6}$ alkynyl, $C_{1-6}$ haloalkyl (in particular —CF$_3$), $C_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —P=O(OH)(NH$_2$), —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

In an embodiment and with specific reference to compounds of formulae (I), (Ia), or (Ib) $R_2$ is selected from $C_1$-$C_4$ alkyl, $C_1$-$C_4$ haloalkyl, phenyl, F or Cl, and $R_3$ is selected from hydrogen, $C_1$-$C_4$ alkyl, $C_1$-$C_4$ haloalkyl, or F, Cl, or CN, or $R_2$ and $R_3$ together form $C_{4-9}$ cycloalkyl or $C_{4-9}$ cycloalkenyl.

In an embodiment $R_6$-$R_8$ are hydrogen.

Accordingly, in another aspect the invention provides compounds of formula (I'), or salts thereof:

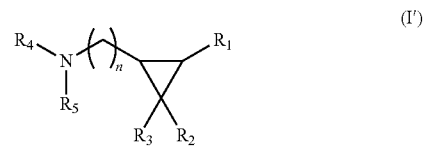

(I')

wherein $R_1$ is selected from optionally substituted aryl, optionally substituted benzyl, optionally substituted heteroaryl, or optionally substituted heterocyclyl;

$R_2$ is selected from $C_1$-$C_4$ alkyl, F, Cl, phenyl or $C_1$-$C_4$ haloalkyl;

$R_3$ is selected from hydrogen, $C_1$-$C_4$ alkyl, F, Cl, CN, or $C_1$-$C_4$ haloalkyl; or $R_2$ and $R_3$ together form $C_{4-9}$ cycloalkyl or $C_{4-9}$ cycloalkenyl;

$R_4$ is selected from optionally substituted heteroaryl, optionally substituted heterocyclyl, or optionally substituted aryl;

$R_5$ is selected from hydrogen or $C_1$-$C_4$ alkyl; and n is 1-3.

Also, in another aspect the invention provides compounds of formula (Ia'), or salts thereof:

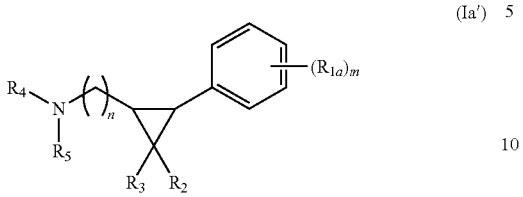

wherein
each $R_{1a}$ is independently selected from the group consisting of optionally substituted lower alkyl, optionally substituted aryl, optionally substituted aryloxy, optionally substituted heteroaryl, optionally substituted heterocyclyl, —P=O(OH)(NH$_2$), —C(O)NR'R', —NR'S(O)$_2$NR'R', —NR'—S(O)$_2$R', —NR'C(O)R', —S(O)$_2$—NR'R' and —NR'R' (where each R' is independently selected from hydrogen, lower alkyl, C$_3$-C$_7$ cycloalkyl, heterocyclyl, heteroaryl, —OH, or NH$_2$), —S(O)R'' (where R'' is lower alkyl, or cycloalkyl), —S(O)$_2$R''' (where R''' is lower alkyl, or cycloalkyl), or any two adjacent $R_{1a}$ together form heterocyclyl or heteroaryl;
m is 0-5;
$R_2$ is selected from C$_1$-C$_4$ alkyl, C$_1$-C$_4$ haloalkyl, phenyl, F, or Cl;
$R_3$ is selected from hydrogen, C$_1$-C$_4$ alkyl, C$_1$-C$_4$ haloalkyl, F, Cl, or CN; or
$R_2$ and $R_3$ together form C$_{4-9}$ cycloalkyl or C$_{4-9}$ cycloalkenyl;
$R_4$ is selected from optionally substituted heteroaryl, optionally substituted heterocyclyl, or optionally substituted aryl;
$R_5$ is independently selected from hydrogen, or C$_1$-C$_4$ alkyl; and
n is 1-3.
In relation to the aforementioned compounds the following definitions may also apply:
a) $R_2$ and $R_3$ are both C$_1$-C$_3$ alkyl (preferably methyl), or $R_2$ and $R_3$ together form a C$_4$-C$_9$ cycloalkyl ring.
b) $R_2$ and $R_3$ are both F.
c) $R_2$ and $R_3$ are both methyl.
d) $R_2$ is methyl, and $R_3$ is hydrogen.
e) $R_2$ and $R_3$ together form a C$_4$-C$_9$ cycloalkyl ring, preferably cyclopentyl or cyclohexyl ring.
In relation to the aforementioned compounds the following further additional definitions may also apply:
f) $R_2$ and $R_3$ are both independently C$_1$-C$_3$ alkyl (preferably methyl), or both F, or $R_2$ and $R_3$ together, form a C$_4$-C$_9$ cycloalkyl ring, and $R_4$ is selected from heteroaryl or aryl each of which may be independently substituted by one to three substituents selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NHC$_{1-4}$ alkyl, —N(C$_{1-4}$ alkyl)$_2$, —CN, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, —S(O)R''' (where R''' is lower alkyl or cycloalkyl) and —S(O)$_2$R''' (where R''' is lower alkyl, or cycloalkyl).
g) $R_2$ and $R_3$ are both CH$_3$, and $R_4$ is selected from heteroaryl or aryl each of which may be independently substituted by one to three substituents selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NHC$_{1-4}$ alkyl, —N(C$_{1-4}$ alkyl)$_2$, —CN, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, —S(O)R''' (where R''' is lower alkyl or cycloalkyl) and —S(O)$_2$R''' (where R''' is lower alkyl, or cycloalkyl).
h) $R_2$ is methyl, $R_3$ is hydrogen, and $R_4$ is selected from heteroaryl or aryl each of which may be independently substituted by one to three substituents selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NHC$_{1-4}$ alkyl, —N(C$_{1-4}$ alkyl)$_2$, —CN, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, —S(O)R''' (where R''' is lower alkyl or cycloalkyl) and —S(O)$_2$R''' (where R''' is lower alkyl, or cycloalkyl).
i) $R_2$ and $R_3$ together, form a C$_4$-C$_9$ cycloalkyl ring, preferably cyclopentyl or cyclohexyl ring, and $R_4$ is selected from heteroaryl or aryl each of which may be independently substituted by one to three substituents selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NHC$_{1-4}$ alkyl, —N(C$_{1-4}$ alkyl)$_2$, —CN, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, —S(O)R''' (where R''' is lower alkyl or cycloalkyl) and —S(O)$_2$R''' (where R''' is lower alkyl, or cycloalkyl).

In relation to the aforementioned compounds of formulae (Ia) and (Ia') the following additional definitions may also apply;
j) $R_2$ and $R_3$ are both independently C$_1$-C$_3$ alkyl (preferably methyl), or both F, or $R_2$ and $R_3$ together, form a C$_4$-C$_9$ cycloalkyl ring, and $R_4$ is selected from heteroaryl or aryl each of which may be independently substituted by one to three substituents selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NHC$_{1-4}$ alkyl, —N(C$_{1-4}$ alkyl)$_2$, —CN, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, —S(O)R''' (where R''' is lower alkyl or cycloalkyl) and —S(O)$_2$R''' (where R''' is lower alkyl, or cycloalkyl), and m is 1 or 2, and each $R_{1a}$ is independently selected from the group consisting of optionally substituted lower alkyl, optionally substituted aryl, optionally substituted aryloxy, optionally substituted heteroaryl, optionally substituted heterocyclyl, —P=O(OH)(NH$_2$), —C(O)NR'R', —NR'S(O)$_2$NR'R', —NR'—S(O)$_2$R', —NR'C(O)R', —S(O)$_2$—NR'R' and —NR'R' (where each R' is independently selected from hydrogen, lower alkyl, C$_3$-C$_7$ cycloalkyl, heterocyclyl, heteroaryl, —OH, or NH$_2$), —S(O)R'' (where R'' is lower alkyl, or cycloalkyl), —S(O)$_2$R''' (where R''' is lower alkyl, or cycloalkyl), or any two adjacent $R_{1a}$ together form heterocyclyl or heteroaryl.
k) $R_2$ and $R_3$ are both CH$_3$, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NHC_{1-4}$ alkyl, —$N(C_{1-4}$ alkyl$)_2$, —CN, —$S(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, —S(O)R''' (where R''' is lower alkyl or cycloalkyl) and —$S(O)_2R'''$ (where R''' is lower alkyl, or cycloalkyl), and m is 1 or 2, and each $R_{1a}$ is independently selected from the group consisting of optionally substituted lower alkyl, optionally substituted aryl, optionally substituted aryloxy, optionally substituted heteroaryl, optionally substituted heterocyclyl, —P=O(OH)($NH_2$), —C(O)NR'R', —NR'S(O)$_2$NR'R', —NR'—S(O)$_2$R', —NR'C(O)R', —S(O)$_2$—NR'R' and —NR'R' (where each R' is independently selected from hydrogen, lower alkyl, $C_3$-$C_7$ cycloalkyl, heterocyclyl, heteroaryl, —OH, or $NH_2$), —S(O)R'' (where R'' is lower alkyl, or cycloalkyl), —$S(O)_2R'''$ (where R''' is lower alkyl, or cycloalkyl), or any two adjacent $R_{1a}$ together form heterocyclyl or heteroaryl.

l) $R_2$ is methyl, $R_3$ is hydrogen, and $R_4$ is selected from heteroaryl or aryl each of which may be independently substituted by one to three substituents selected from halogen (in particular; Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NHC_{1-4}$ alkyl, —$N(C_{1-4}$ alkyl$)_2$, —CN, —$S(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, —S(O)R''' (where R''' is lower alkyl or cycloalkyl) and —$S(O)_2R'''$ (where R''' is lower alkyl, or cycloalkyl), and m is 1 or 2, and each $R_{1a}$ is independently selected from the group consisting of optionally substituted lower alkyl, optionally substituted aryl, optionally substituted aryloxy, optionally substituted heteroaryl, optionally substituted heterocyclyl, —P=O(OH)($NH_2$), —C(O)NR'R', —NR'S(O)$_2$NR'R', —NR'—S(O)$_2$R', —NR'C(O)R', —S(O)$_2$—NR'R' and —NR'R' (where each R' is independently selected from hydrogen, lower alkyl, $C_3$-$C_7$ cycloalkyl, heterocyclyl, heteroaryl, —OH, or $NH_2$), —S(O)R'' (where R'' is lower alkyl, or cycloalkyl), —$S(O)_2R'''$ (where R''' is lower alkyl, or cycloalkyl), or any two adjacent $R_{1a}$ together form heterocyclyl or heteroaryl.

m) $R_2$ and $R_3$ together form a $C_4$-$C_9$ cycloalkyl ring, preferably cyclopentyl or cyclohexyl ring, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NHC_{1-4}$ alkyl, —$N(C_{1-4}$ alkyl$)_2$, —CN, —$S(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, —S(O)R''' (where R''' is lower alkyl or cycloalkyl) and —$S(O)_2R'''$ (where R''' is lower alkyl, or cycloalkyl), and m is 1 or 2, and each $R_{1a}$ is independently selected from the group consisting of optionally substituted lower alkyl, optionally substituted aryl, optionally substituted arylyoxy, optionally substituted heteroaryl, optionally substituted heterocyclyl, —P=O(OH)($NH_2$), —C(O)NR'R', —NR'S(O)$_2$NR'R', —NR'—S(O)$_2$R', —NR'C(O)R', —S(O)$_2$—, NR'R' and —NR'R' (where each R' is independently selected from hydrogen, lower alkyl, $C_3$-$C_7$ cycloalkyl, heterocyclyl, heteroaryl, —OH, or $NH_2$), —S(O)R'' (where R'' is lower alkyl, or cycloalkyl), —$S(O)_2R'''$ (where R''' is lower alkyl, or cycloalkyl), or any two adjacent $R_{1a}$ together form heterocyclyl or heteroaryl.

In relation to the aforementioned compounds the following further definitions may apply:

n) $R_2$ and $R_3$ together form a cyclohexyl or cyclopentyl ring.

o) $R_2$ and $R_3$ together form a cyclohexyl or cyclopentyl ring, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NHC_{1-4}$ alkyl, —$N(C_{1-4}$ alkyl$)_2$, —CN, —$S(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, —S(O)R''' (where R''' is lower alkyl or cycloalkyl) and $S(O)_2R'''$ (where R''' is lower alkyl, or cycloalkyl).

p) $R_2$ and $R_3$ together form a cyclohexyl or cyclopentyl ring, and $R_4$ is selected from heteroaryl or aryl each of which may be independently substitUted by one to three substituents selected from halogen (in particular, Cl, Br or F), $C_{1-6}$ alkyl, $C_{1-6}$ alkoxy, $C_{1-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NHC_{1-4}$ alkyl, —$N(C_{1-4}$ alkyl$)_2$, —CN, —$S(O)_2NH_2$, —$S(O)_2NHC_{1-4}$ alkyl, —$S(O)_2N(C_{1-4}$ alkyl$)_2$, $C_{1-13}$ alkylcarbonyl, $C_{1-6}$ alkoxycarbonyl, and sulfone (in particular $S(O)_2C_{1-4}$ alkyl), and m is 1 or 2, and each $R_{1a}$ is independently selected from the group consisting of optionally substituted lower alkyl, optionally substituted aryl, optionally substituted aryloxy, optionally substituted heteroaryl, optionally substituted heterocyclyl, —P=O(OH)($NH_2$), —C(O)NR'R', —NR'S(O)$_2$NR'R', —NR'—S(O)$_2$R', —NR'C(O)R', —S(O)$_2$—NR'R' and —NR'R' (where each R' is independently selected from hydrogen, lower alkyl, $C_3$-$C_7$ cycloalkyl, heterocyclyl, heteroaryl, —OH, or $NH_2$), —S(O)R'' (where R'' is lower alkyl, or cycloalkyl), —$S(O)_2R'''$ (where R''' is lower alkyl, or cycloalkyl), or any two adjacent $R_{1a}$ together form heterocyclyl or heteroaryl;

In relation to the aforementioned compounds one or more of the following preferred definitions (where appropriate) may also apply:

q) each $R_{1a}$ is independently selected from the group consisting of optionally substituted lower alkyl, optionally substituted aryl, optionally substituted aryloxy, optionally substituted heteroaryl, optionally substituted heterocyclyl, —P=O(OH)($NH_2$), —C(O)NR'R', —NR'S(O)$_2$NR'R', —NR'—S(O)$_2$R', —NR'C(O)R', —S(O)$_2$—NR'R' and —NR'R' (where each R' is independently selected from hydrogen, lower alkyl, $C_3$-$C_7$ cycloalkyl, heterocyclyl, heteroaryl, —OH, or $NH_2$), —S(O)R'' (where R'' is lower alkyl, or cycloalkyl), —$S(O)_2R'''$ (where R''' is lower alkyl, or cycloalkyl), or any two adjacent $R_{1a}$ together form heterocyclyl or heteroaryl;

r) m is 1.

In a further embodiment and with reference to all of the aforementioned compounds $R_5$ is H or $CH_3$.

In a further embodiment and with reference to all of the aforementioned formulae, the following additional preferred definitions may also apply.

$R_4$ is selected from:

(a)

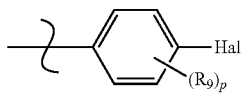

wherein Hal is a halogen;
p is 0, 1 or 2; and
each $R_9$ is independently selected from halogen, CN, $NO_2$, haloalkyl, aryl, heteroaryl, $C_{1-3}$ alkoxy, $C_{1-3}$ haloalkoxy, $C_{1-3}$ alkyl, or $CO_2R'$ (where R' is a lower alkyl or H);

Or (b)

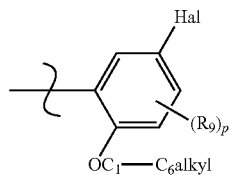

wherein Hal is a halogen;
p is 0, 1 or 2; and
each $R_9$ is independently selected from halogen, CN, $NO_2$, haloalkyl, aryl, heteroaryl, $C_{1-3}$ alkoxy, $C_{1-3}$ haloalkoxy, $C_{1-3}$ alkyl, or $CO_2R'$ (where R' is a lower alkyl or H);

or (c) a heteroaryl substituted from 1 to 3 times from a group selected from $C_1$-$C_3$ alkyl, $C_{1-6}$ alkoxy, $C_{2-6}$ alkenyl, $C_{2-6}$ alkynyl, $C_{1-6}$ haloalkyl, $C_{1-3}$ haloalkoxy, —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$ alkoxycarbonyl, $CO_2H$, —S(O)R''' (where R''' is lower alkyl or cycloalkyl) and —$S(O)_2R'''$ (where R''' is lower alkyl, cycloalkyl or OH).

In an embodiment $R_4$ is selected from pyridyl, pyrazolyl or thiazolyl.

In yet a further embodiment and with reference to the compounds of the invention of formulae (I) and (Ib):

$R_1$ is phenyl independently substituted by one or two substituents selected from independently selected from the group consisting of optionally substituted lower alkyl, optionally substituted aryl (preferably optionally substituted phenyl), optionally substituted aryloxy (preferably optionally substituted phenyloxy), optionally substituted heteroaryl, optionally substituted heterocyclyl, —P=O(OH)($NH_2$), —C(O)NR'R', —NR'S(O)$_2$NR'R', —NR'—S(O)$_2$R', —NRC(O)R', —S(O)$_2$—NR'R' and —NR'R' (where each R' is independently selected from hydrogen, lower alkyl, $C_3$-$C_7$ cycloalkyl, heterocyclyl, heteroaryl, —OH, or $NH_2$), —S(O)R''' (where R''' is lower alkyl, or cycloalkyl), —$S(O)_2R'''$ (where R''' is lower alkyl, cycloalkyl), or any two adjacent substituents together form heterocyclyl or heteroaryl;

$R_2$ and $R_3$ are the same and represent $C_{1-4}$ alkyl, or together a $C_5$-$C_6$ cycloalkyl;

$R_4$ is heteroaryl or heteroaryl independently substituted one or two times by $C_{1-4}$ alkyl, $C_{1-4}$ haloalkyl, halogen, or $C_{1-4}$ alkoxy; or is phenyl or phenyl independently substituted one or two times by $C_{1-4}$ alkyl, $C_{1-4}$ haloalkyl, halogen, or $C_{1-4}$ alkoxy; and $R_5$ is H or lower alkyl.

In a further embodiment and with reference to any one of formula (I), (Ia), (Ib), (Ic) or (Ia'), n is 1-3, for instance, n=1, n=2, or n=3. Preferably n=1.

In an embodiment m is 1 and $R_{1a}$ is selected from:
—$S(O)_2R'''$ (where R''' is lower alkyl, or cycloalkyl),
—$S(O)_2NR'R''$ (where R' is hydrogen and R'' is selected from hydrogen, lower alkyl, —OH, or $NH_2$),
lower alkyl, substituted 1 or 2 times with a substituent group selected from $CF_3$ and $NH_2$,
lower haloalkyl,
optionally substituted heterocyclyl (preferably 4 or 5-membered heterocyclyl),
—NR'S(O)$_2$NR'R' (where each R' is independently selected from hydrogen or lower alkyl, $C_3$-$C_7$ cycloalkyl, heterocyclyl, or heteroaryl), or
—NR'—S(O)$_2$R' (where each R' is independently selected from hydrogen or lower alkyl, $C_3$-$C_7$ cycloalkyl, heterocyclyl, or heteroaryl).

In a further embodiment the $R_{1a}$ substituent is in the para position.

In an embodiment m is 1 and $R_{1a}$ is selected from

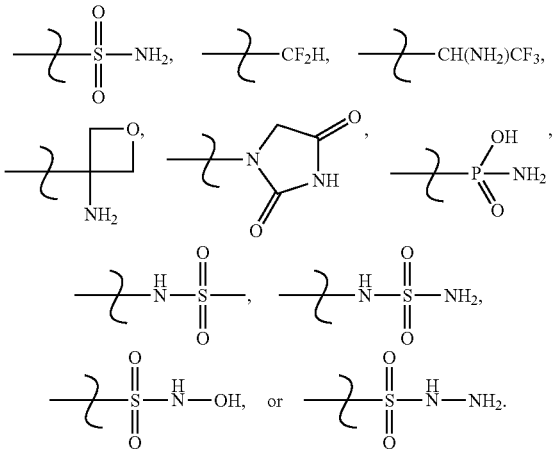

In an embodiment m is 1 and the substituent is in the para position.

In a further preferred embodiment and with reference to any one of formula (I), (Ia), (Ib), (Ic), or (Ia'), n is 1 and $R_1$ or

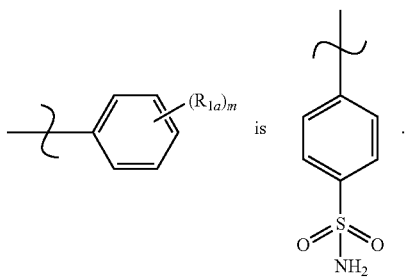

In an embodiment $R_{1a}$ is

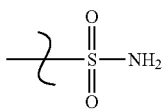

and $R_4$ is

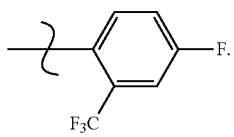

In an embodiment $R_{1a}$ is

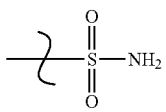

and $R_4$ is

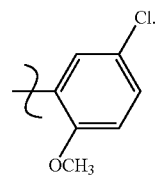

In the list below (which are representative examples of compounds of the present invention) the structures contain one or more stereogenic centers, the respective structures are depicted without absolute configuration. These structures also include pure stereoisomers in each possible absolute configuration as well as mixtures of isomers in all ratios including racemates.

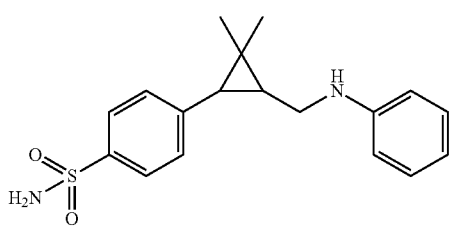

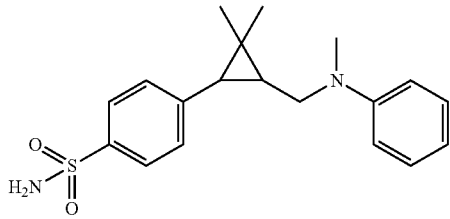

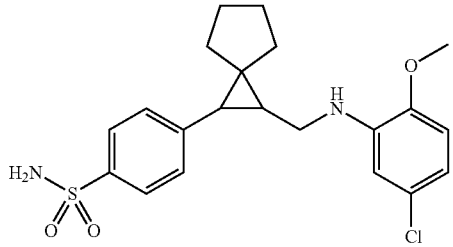

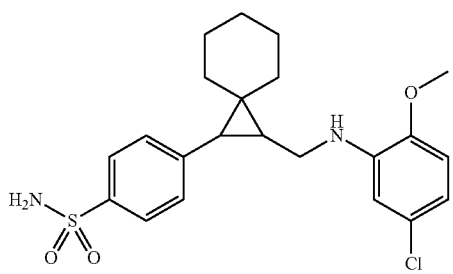

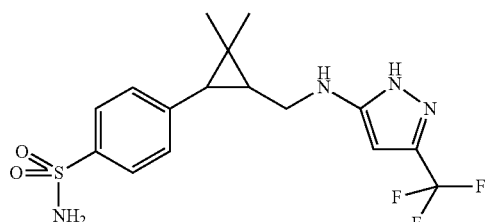

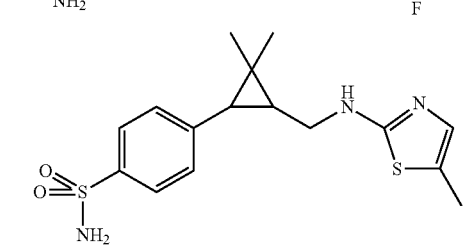

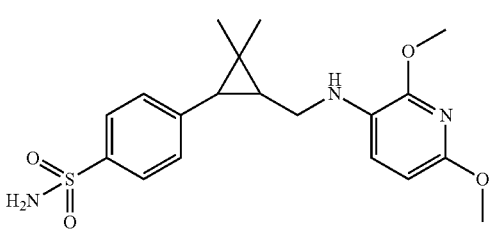

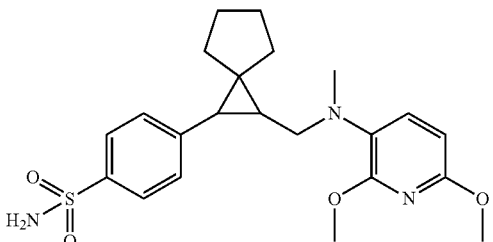

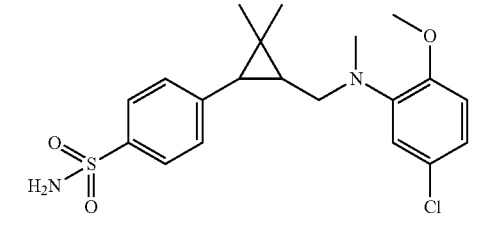

-continued
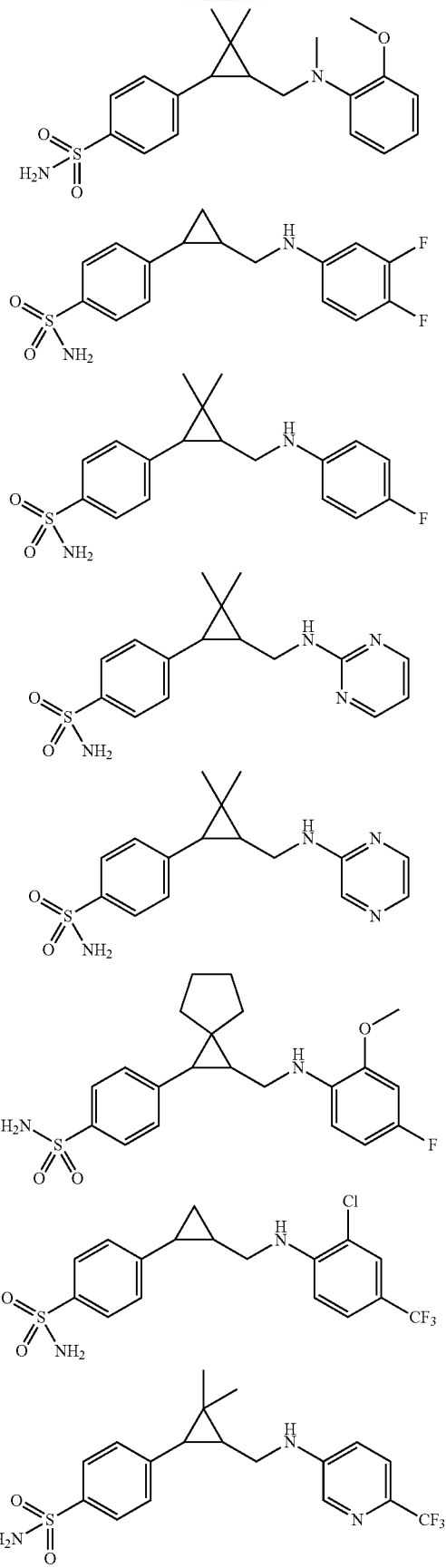
-continued
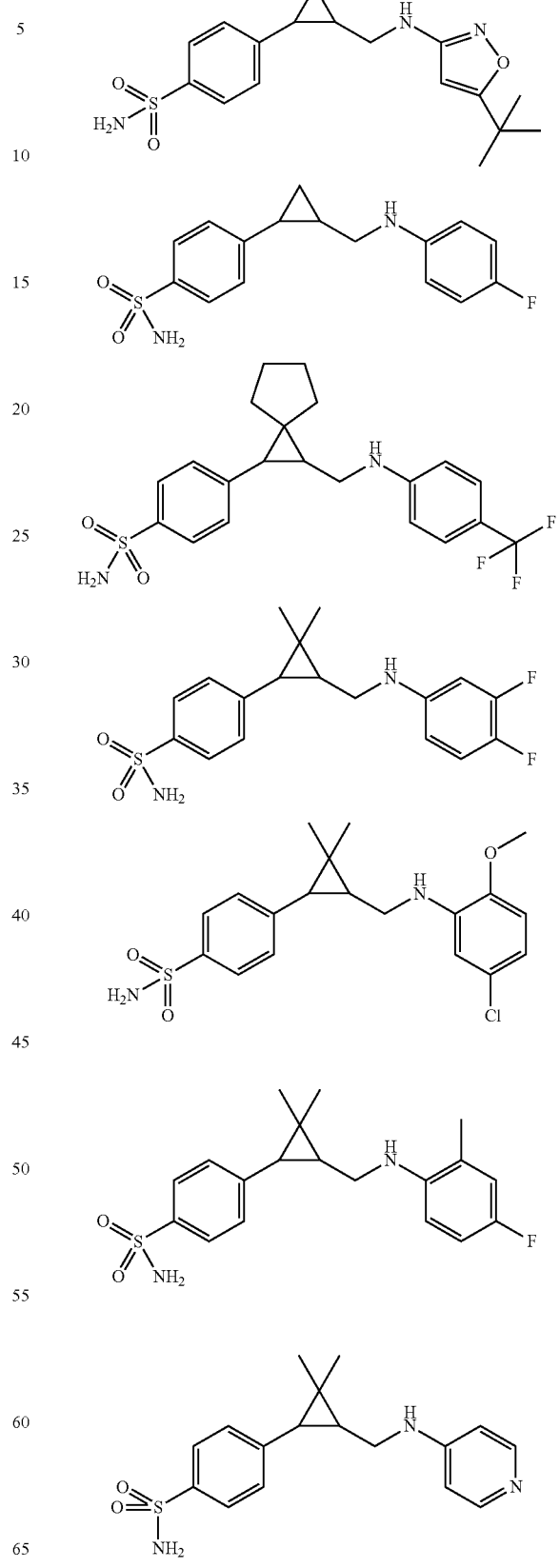

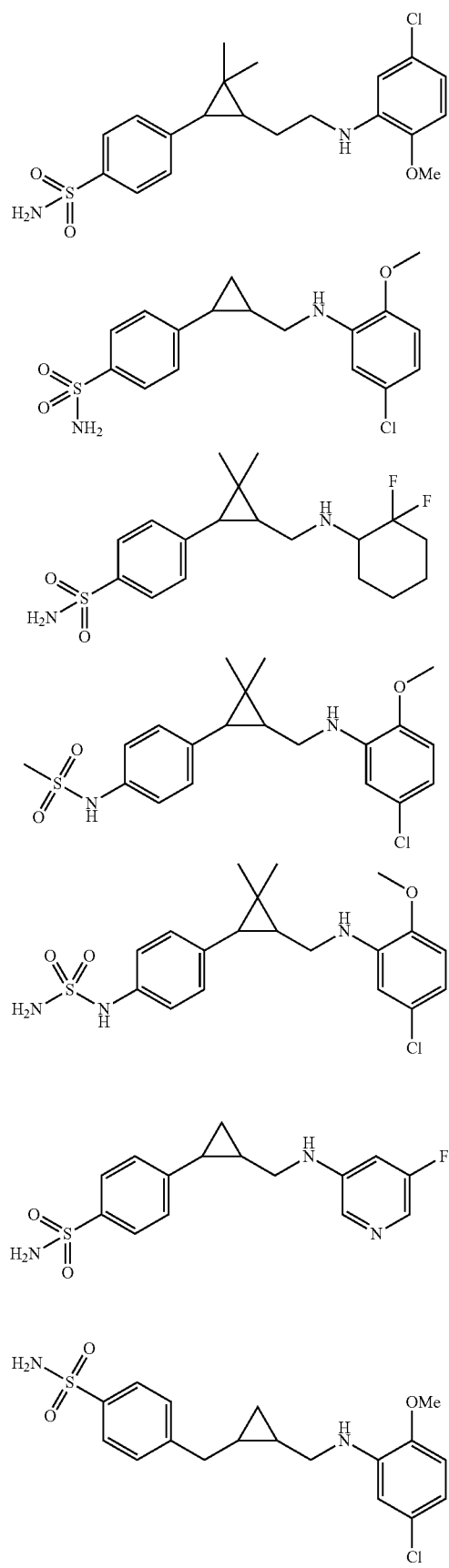
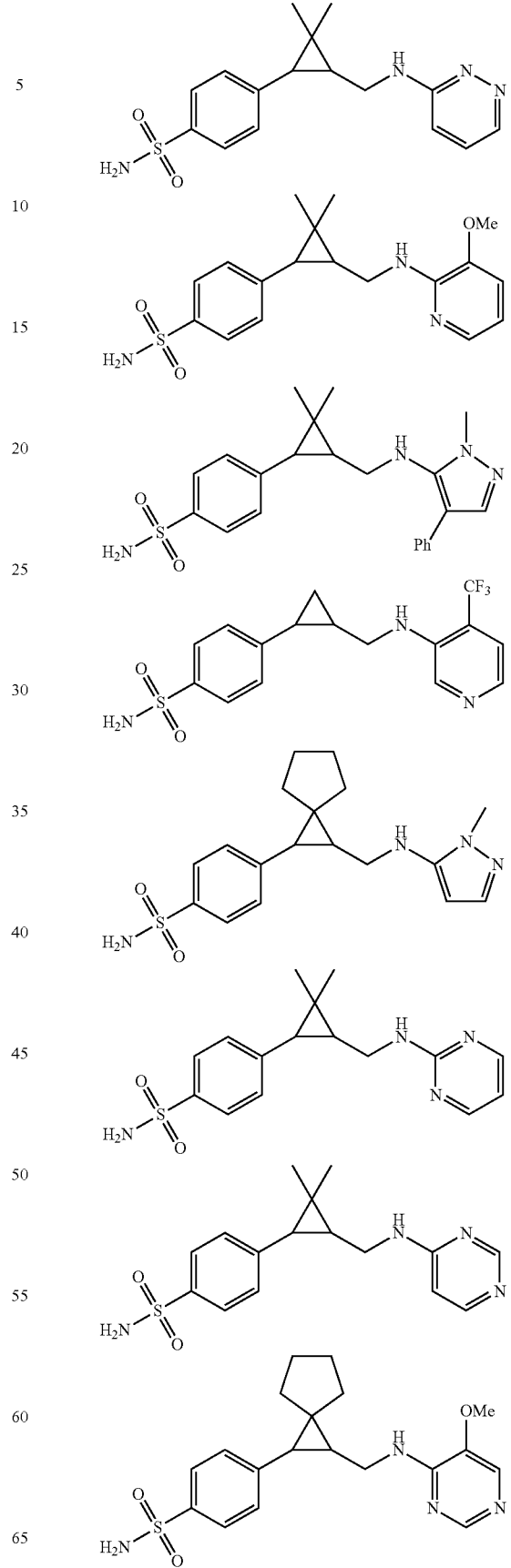

-continued

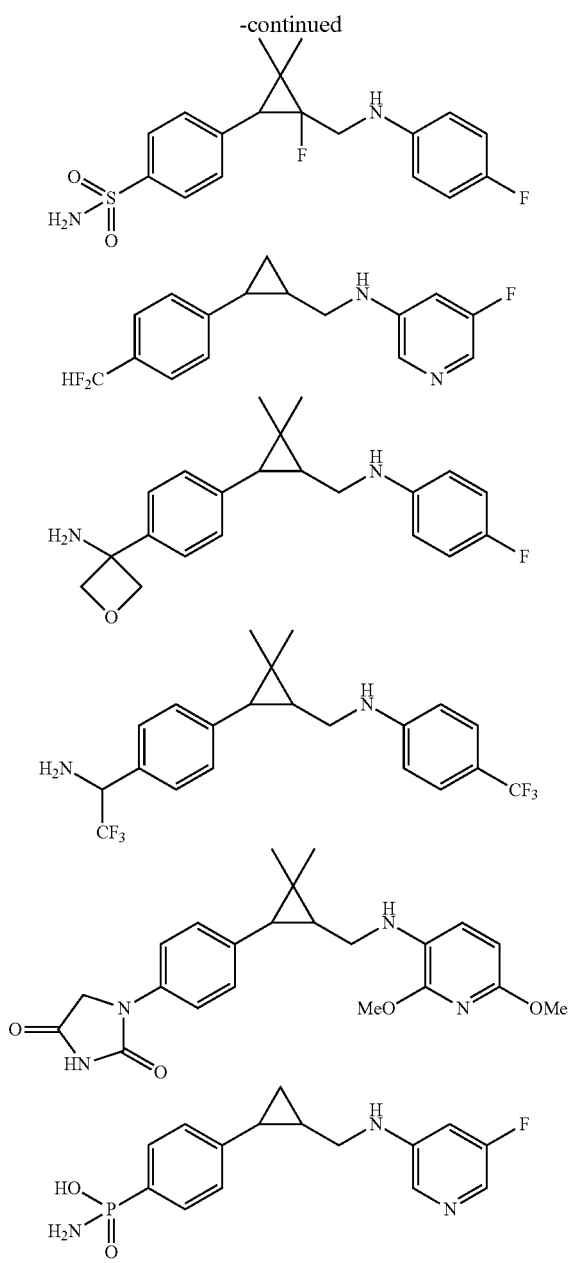

The salts of the compounds of the invention are preferably pharmaceutically acceptable, but it will be appreciated that non-pharmaceutically acceptable salts also fall within the scope of the present invention, since these, are useful as intermediates in the preparation of pharmaceutically acceptable salts.

It will be appreciated that the compounds of the invention, and the salts thereof, can be presented in the form of pharmaceutically acceptable derivatives. The term "pharmaceutically acceptable derivative" includes pharmaceutically acceptable esters, prodrugs, solvates and hydrates of the compounds of the invention, or salts thereof. Pharmaceutically acceptable derivatives may include any pharmaceutically acceptable hydrate or any other compound or prodrug which, upon administration to a subject, is capable of providing (directly or indirectly) a compound of the invention, or an active metabolite or residue thereof.

The pharmaceutically acceptable salts include acid addition salts, base addition salts, and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. The base addition salts include but are not limited to salts such as sodium, potassium, calcium, lithium, magnesium, ammonium and alkylammonlum. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be In crystalline form and/or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters, and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of the invention or of salt thereof.

It will be appreciated that the compounds of the invention have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

It will be appreciated that in respect of the cyclopropyl carbons which connect variables $R_6$ and $R_1$ that these chiral positions give rise to various stereoisomers. In an embodiment the invention contemplates trans-isomers. In another embodiment the invention contemplates cis-isomers. In a further embodiment the invention contemplates an enantiomeric mixture of trans-isomers. In a further embodiment the invention provides a single trans-enantiomer, or an enantiomerically enriched mixture thereof.

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds or pharmaceutically acceptable salts thereof, including pharmaceutically acceptable derivatives thereof, and optionally a pharmaceutically acceptable carrier or diluent.

In another aspect, the present invention provides pharmaceutical compositions for use as a positive allosteric modulator of α7nAChRs, for instance in the treatment or prevention of cognitive deficits associated with neurodegeneration or neuropsychiatric diseases, or in treating inflammation or in treating neuropathic pain, the composition comprising an effective amount of a compound of the invention, or a pharmaceutically acceptable salt thereof, including a pharmaceutically acceptable derivative thereof, and optionally a pharmaceutically acceptable carrier or diluent.

Accordingly these compositions may be thought as either procognitive or antiinflammatory or neuroprotective agents or analgesics.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form companions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base; usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of the compound of the invention to be administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The pharmaceutical preparations of the compounds according to the present invention may be co-administered with one or more other active agents in combination therapy. For example the pharmaceutical preparation of the active compound may be co-administered (for example, separately, concurrently or sequentially), with one or more other agents used to treat cognitive impairment or mood disorders such as acetylcholine esterase inhibitors, antipsychotics, and antidepressants.

It is believed that the compounds of the invention may be beneficial in treating patients with cognitive impairment or aid in increasing cognition. It is believed that this effect may be brought about by positive allosteric modulation of $\alpha 7$ nAChRs. Positive allosteric modulators (PAMs) of nicotinic acetylcholine receptors (nAChRs) can be characterised by two types (type I and type II). Whilst both potentiate peak agonist-induced responses, they have different effects on the rate of agonist-induced receptor desensitization. Type I PAMs have little or no effect on the rapid rate of desensitization that is characteristics of $\alpha 7$ nAChRs, whereas type II PAMs cause dramatic slowing of receptor desensitization.

In one embodiment the compounds of formula (I), (Ia), (Ib) or (Ic) (and subformulae thereof) are characterised as type I.

In one embodiment the compounds of formula (I), (Ia), (Ib) or (Ic) (and subformulae thereof) are characterised as type II.

It is envisaged that the compounds may additionally be useful in the treatment of patients, including a mammal and especially a human, suffering from neuropsychiatric diseases and neurodegenerative diseases involving a dysfunction of the cholinergic system, and further conditions of memory and/or cognitive impairment, including, for example, schizophrenia, Attention Deficit Hyperactivity Disorder, anxiety, mania, depression, manic depression (as examples of neuropsychiatric disorders), Tourette's syndrome, Parkinson's disease, Huntington's disease (as examples of neurodegenerative diseases), and/or cognitive disorders (such as Alzheimer's disease, Lewy Body Dementia, Amyotrophic Lateral Sclerosis, memory Impairment, memory loss, cognition deficit).

Neurodegenerative disorders include, but are not limited to, treatment and/or prophylaxis of Alzheimer's diseases, Pick's disease, diffuse Lewy Body disease, progressive supranuclear palsy (or Steel-Richardson syndrome), multisystem degeneration (or Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy; spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Straussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, the compounds of the invention may be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia.

The invention provides methods of treating subjects suffering from memory impairment due to, for example, Alzheimer's disease, mild cognitive impairment due to aging, schizophrenia, Attention Deficit Hyperactivity Disorder, Parkinson's disease, multiple sclerosis, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases.

For certain of the abovementioned conditions it is clear that the compounds may be used prophylactically as well as for the alleviation of symptoms.

References herein to "treatment" or the like are to be understood to include such prophylactic treatment, as well as therapeutic treatments.

The compounds of the present invention as agents which modulate the α7 nAChR may be particularly useful in the therapeutic or prophylactic treatment of diseases such as schizophrenia, bipolar disorder, anxiety, AD, ADHD, mild cognitive impairment, Parkinson's Disease, Huntington's disease, Tourette's syndrome, brain trauma, jetlag and nicotine addiction.

Accordingly in a further aspect of the invention, there is provided a means for ameliorating the cognitive deficits associated with neurodegenerative and neuropsychiatric diseases and also inflammatory diseases by the application of a positive allosteric modulators of α7 nAChRs selected from a compound of the invention, or salt thereof, including a pharmaceutically acceptable derivative thereof, or a composition comprising the compound of the invention, or salt thereof, or a pharmaceutically acceptable derivative thereof.

In another aspect of the invention a method is provided for preventing or treating cognitive deficits involving dysfunction of the cholinergic system including the step of administrating a compound of the invention, or salt thereof, or a composition comprising the compound or salt thereof.

In another preferred form of the invention there is provided a method for preventing or treating neurodegenerative or neuropsychiatric disorders including the step of administrating a compound of the invention, or a pharmaceutically acceptable salt thereof, including a pharmaceutically acceptable derivative thereof, or a composition comprising the compound or pharmaceutically acceptable salt thereof, or pharmaceutically acceptable derivative thereof.

In a further aspect of the present invention, there is provided the use of a compound of the invention, or salt thereof, in the preparation of a medicament for the treatment (therapeutic or prophylactic) of disease states in which modulation of α7 nAChRs would be beneficial.

In a further aspect of the invention there is provided a process for the production of the compounds of the invention, or salts thereof, including pharmaceutically acceptable derivatives thereof.

Compounds of the invention may be prepared according to the following general schemes:

Scheme A

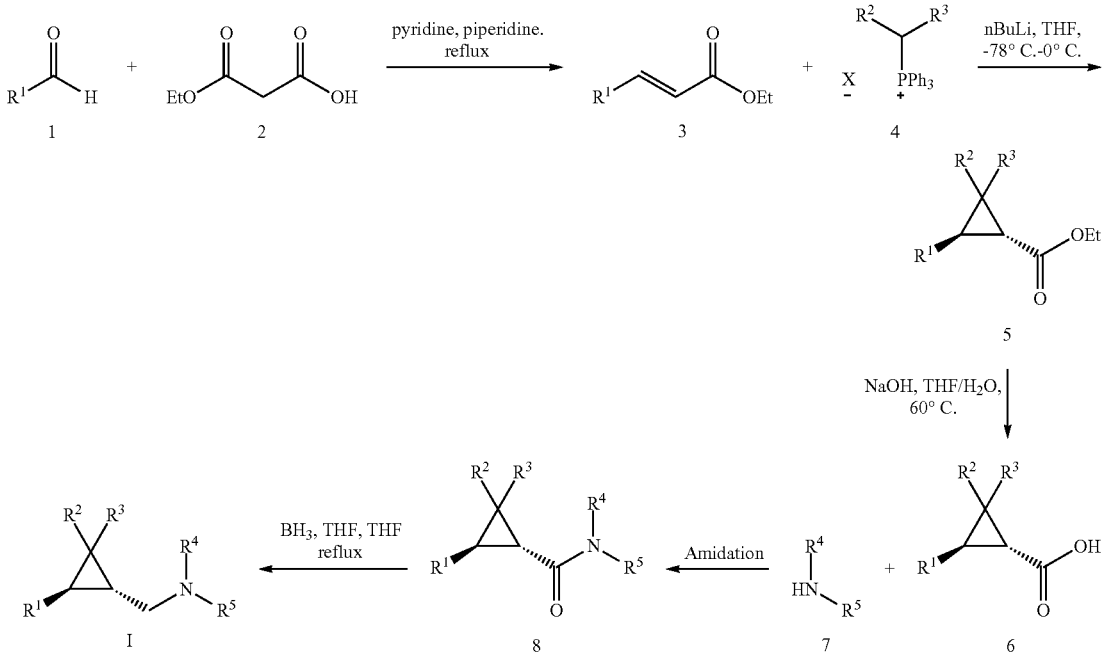

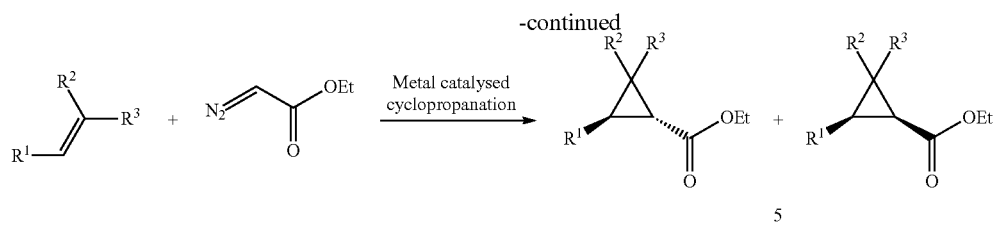

Compounds of the formula (I) can be prepared by synthetic procedures as depicted in Scheme A. Cinnamate esters 1 may be from commercial sources or prepared by Doebner modification of Knoevenagel condensation of an aryl/heteroaryl aldehyde. Typically, an aryl/heteroaryl aldehyde 1 and ester of malonic acid 2 is heated in pyridine/piperidine mixture. Numerous modifications of this procedure as well as alternatives such as Aldol-type condensation or Wittig reaction of aryl or heteroaryl carbonyl compounds with ylides are possible and will be readily apparent to those skilled in the art.

Cyclopropanation of olefin was carried out by reacting cinnamate ester 3 with phosphorus ylides derived from phosphonium salts 4 (where X=Cl, Br, I) as described in *J. Med. Chem.* 2001, 44, 3302. The requisite phosphonium salts can be purchased or prepared by known methods. Those skilled in the art will understand that cyclopropanation of olefins could be achieved by alternative methods, such as Simmons-Smith type reaction of cinnamate ester with Furukawa reagents as described in *Tetrahedron* 1969, 25, 2647 or Michael initiated ring closing reaction of cinnamate ester with sulphur ylides as described in *Synthesis* 2008, 20, 3279. Additionally, treatment of olefins with diazoesters in the presence of metal catalysts can afford access to cyclopropane esters of type 5 with either cis or trans orientation of $R^1$ to the ester moiety favoured depending on catalyst used (*Tetrahedron* 2008, 7041). Ester 5 where $R_2$ and $R_3$ are chloro can be prepared by heating a mixture of cinnamate ester 3 and ethyl trichlorooacetate. Numerous modifications of this procedure such as use of trichloroacetic acid in acetic anhydride as described in *J. Org. Chem.* 1988, 53, 4945 are possible and will be readily apparent to those skilled in the art. Similarly, ester 5 where $R_2$ and $R_3$ are fluoro can be prepared by heating cinnamate 3 with a difluoro carbene generated from suitable reagent such as trimethylsilyl fluorosulfonyldifluoroacetate as described in *J. Fluorine Chem.* 2004, 125, 459. Esters 5 where $R_2$ and $R_3$ together form a cycloalkyl or cycloalkenyl group can be prepared by from corresponding spiro group containing phosphorus ylides. Alternatively, phosphorus ylides where $R^2$ and $R^3$ contains terminal alkene group can be reacted with cinnamate esters, followed by ring-closure metathesis as described in *J. Chem. Res.* 2006, 9, 591 to form ester 5 where $R_2$ and $R_3$ together form cycloalkenyl group, which could be further reduced to form corresponding cycloalkyl group containing ester 5. Ester 5 can be alternatively prepared by the reaction of styrenes with diazoesters giving cyclopropanes in high enantiomeric and diastereomeric excess using chiral ligands and metal catalysts as outlined in *J. Am. Chem. Soc.* 1991, 726.

Ester 5 can be hydrolysed to acid 6 by using known procedures and then reacted with thionyl chloride or oxalyl chloride to offer acid chloride, which can be then reacted with amine 7 to offer amides 8. Numerous alternative amide formation procedures could be used such as direct coupling of acid with amine in presence of dicyclohexyldiimide or other diimides, O-(7-azobenzotriazol-1-yl)-1,1,3,3-tetramethyluronium hexa fluorophosphate) (HATU), propylphosphonlc anhydride (T3P) or conversion of acid to reactive anhydride and then coupling with amine to generate amides 8.

Amides 8 can be reduced by use of borane tetrahydrofuran complex to generate compounds of formula (I). Other reagents such as lithium aluminium hydride or sodium metal in 1-propanol could be used to effect this transformation.

Scheme B

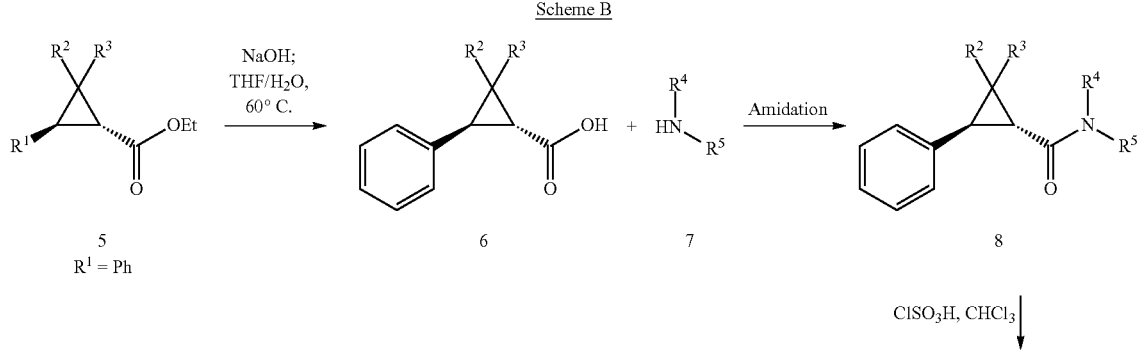

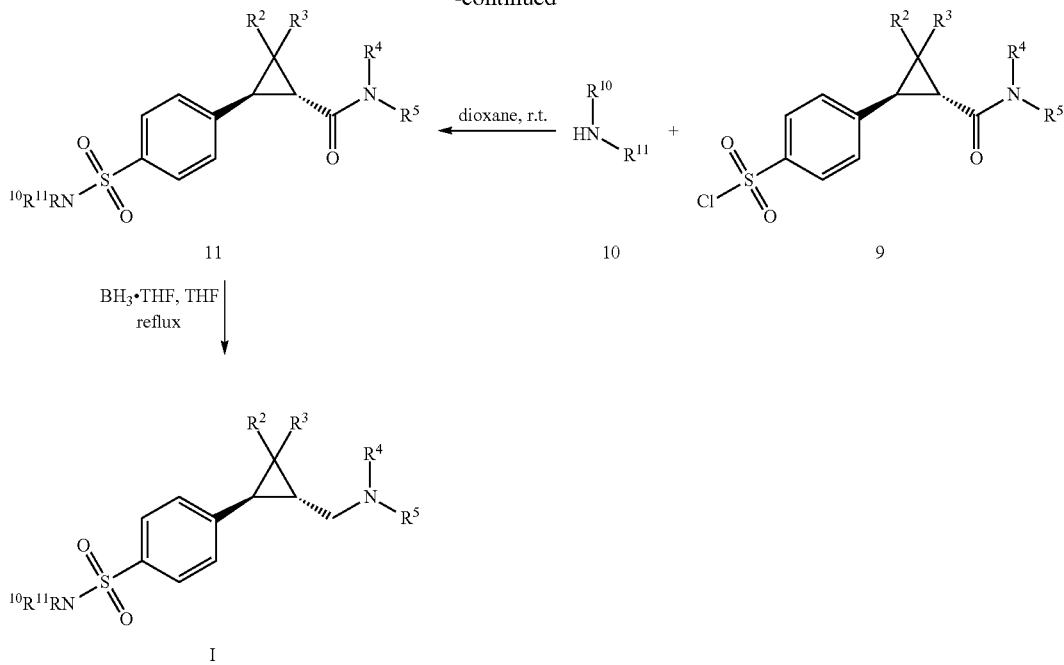

Scheme B outlines the synthesis of compounds of formula (I) from esters 5 (where R¹=Ph). Ester 5 can be hydrolysed to acid 6 by using known procedures and then reacted with amine 7 to offer amides 8 as outlined above. Amide 8 can be converted to sulfonyl chloride through treatment with chlorosulfonic acid and subsequently allowed to react with amine 10 to generate sulfonamides 11. Amides 11 can be reduced by use of borane tetrahydrofuran complex or other aforementioned reagents to provide compounds of formula (I).

Scheme C describes an alternative route to compounds of formula (I). Ester 5 can be reduced to alcohol 12 using standard procedures; alternatively alcohol 12 can be prepared with high enantiomeric excess form from cinnamyl alcohols using Furukawa type chemistry and chiral ligands (*J. Am. Chem. Soc.* 1994, 2651, *Tetrahedron Letters* 1992, 2575). Oxidation of alcohol 12 to give aldehyde 13 can be achieved using standard oxidative methods such as Swern Oxidation, PCC or MnO₂. Reductive amination of aldehyde 13 can be achieved using standard procedures to give amines

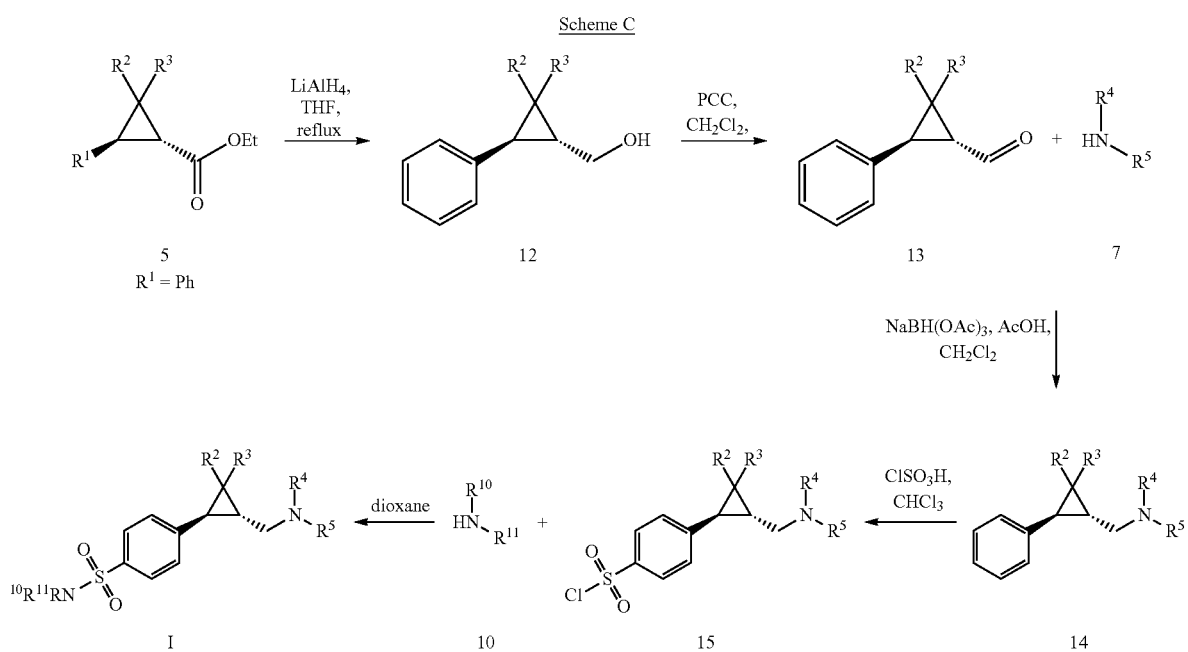

14. Sulfonamidation of amine 14 via sulfonyl chloride to yield compounds of formula (I) can be achieved as described above.

*Chem.* 2008, 5163). Aldehyde 16 can then conceivably be transformed to compounds of formula (I) as described for aldehyde 13 above. Alternatively, acid 6 can be homologated

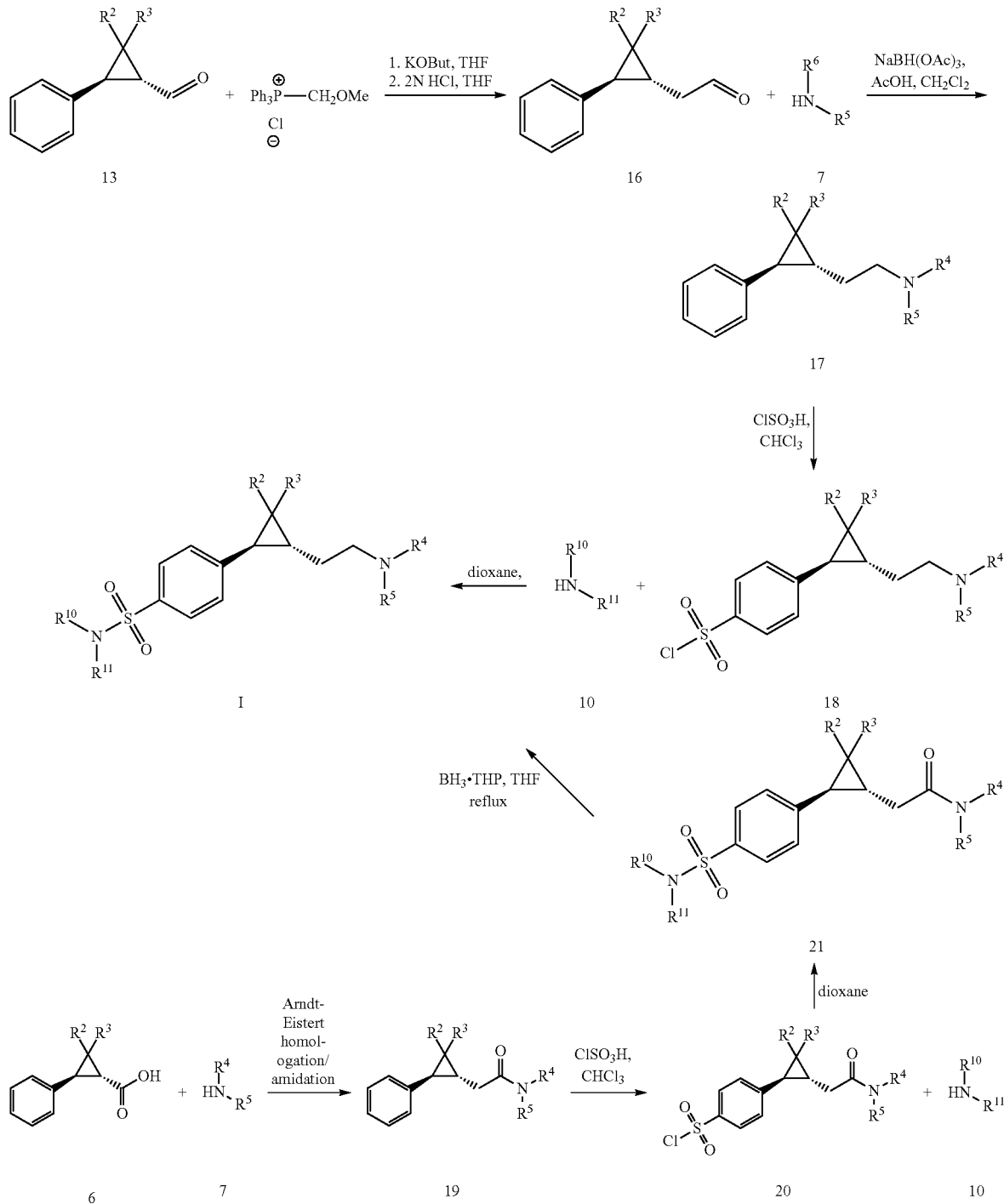

Scheme D

Scheme D describes potential synthesis of compounds of formula (I) where n=2. Aldehyde 13 can be homologated by reaction with methoxymethyl-triphenylphosphonium chloride to form the enol ether followed by acid catalysed deprotection and tautomerisation to aldehyde 16 (*J. Org.* by employing Arndt-Eistert homologation/amidation chemistry (*Org. Biomol. Chem.*, 2006, 323) and the subsequent amide 19 could be transformed into compounds of formula (I) by procedures outlined above for amide 8.

Scheme E

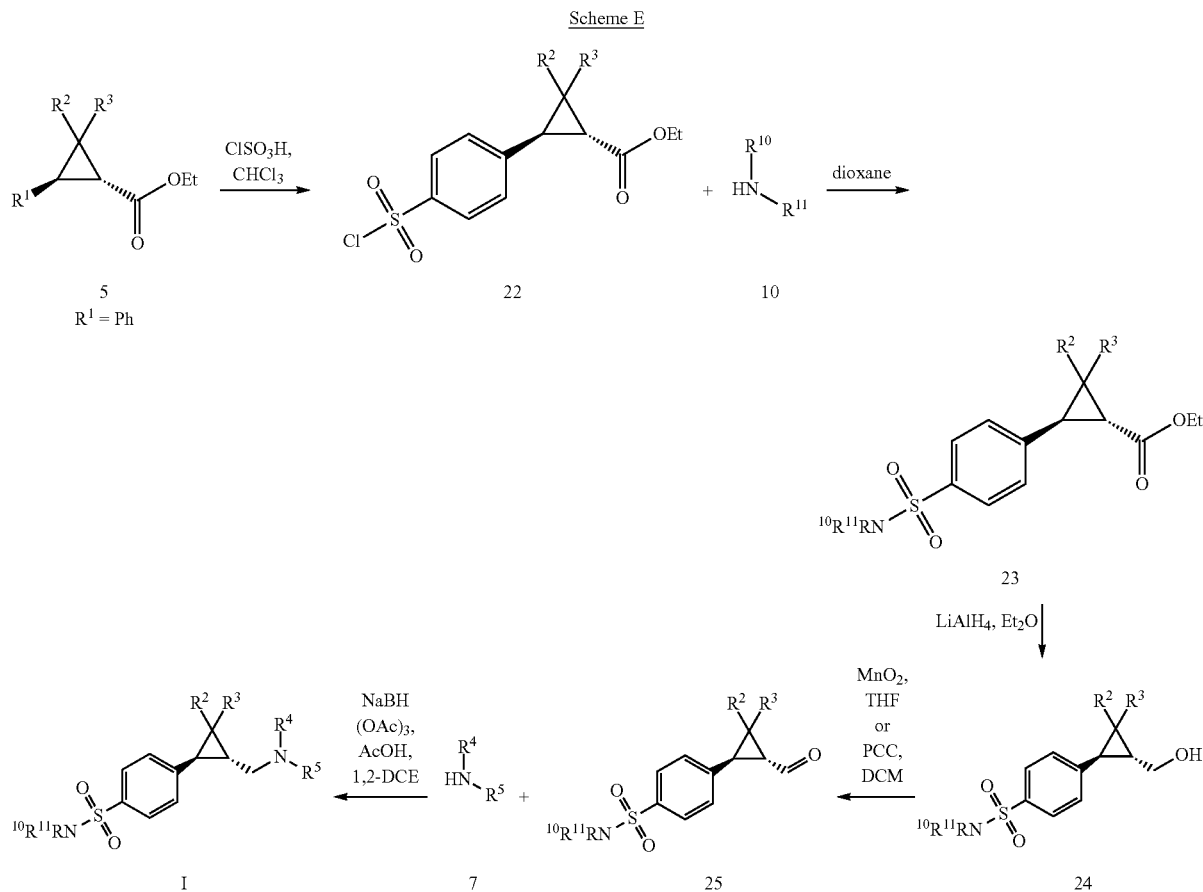

Scheme E outlines another route to the synthesis of compounds of formula (I) from ester 5 (where R¹=Ph). Ester 5 can be converted to sulfonyl chloride 22, through treatment with chlorosulfonic acid, and subsequently allowed to react with amine 10 to generate sulfonamides 23. Ester 23 may be reduced using standard conditions to give alcohol 24, followed by oxidation using standard conditions to give aldehyde 25. Reductive amination with aldehyde 25 and amine 7 can be achieved using standard procedures to provide compounds of formula (I) as indicated above.

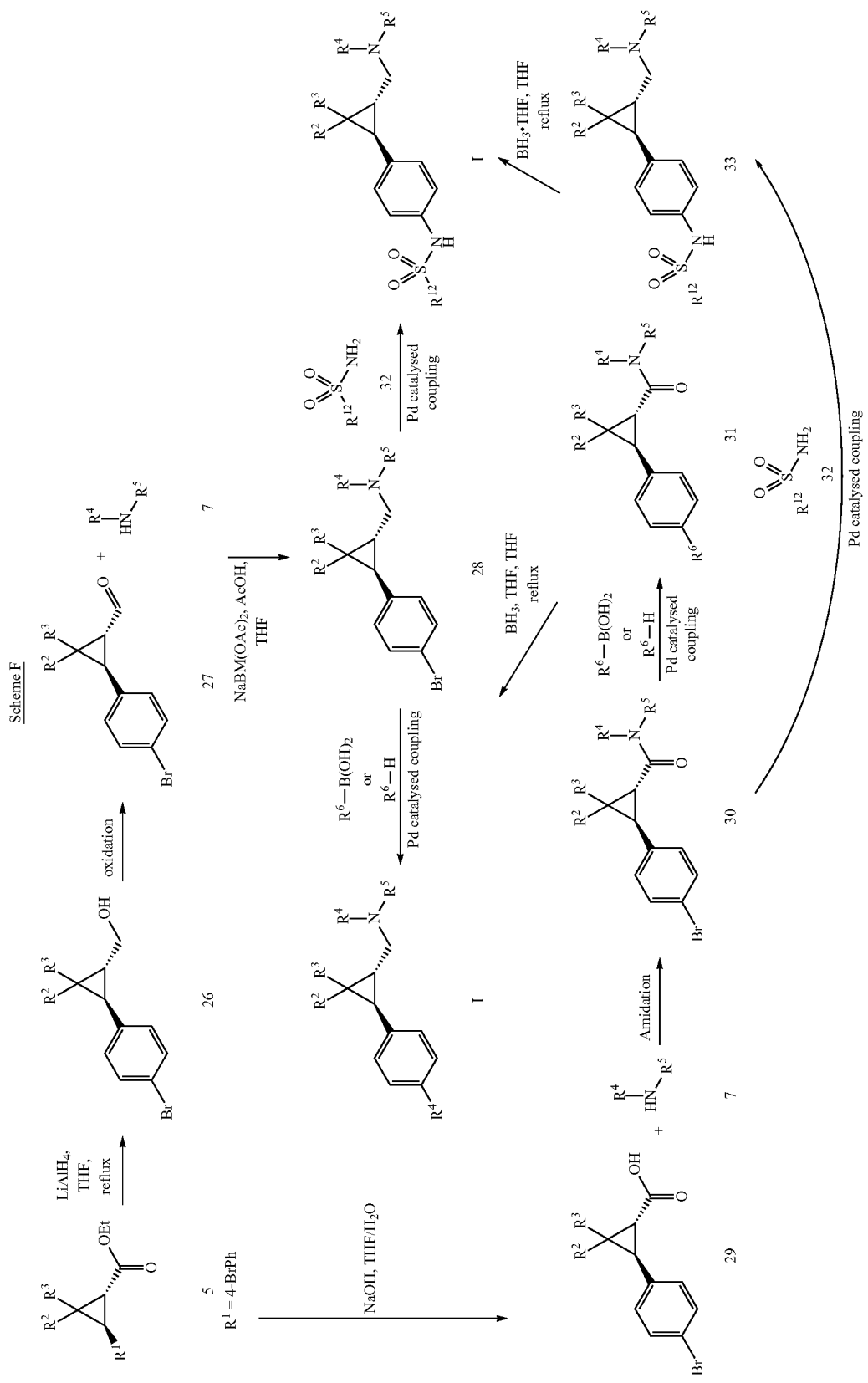

Scheme F outlines another route to the synthesis of compounds of formula (I) from ester 5 (where $R^1$=4-BrPh). Ester 5 can be reduced to alcohol 26 using standard procedures such as $LiAlH_4$ in refluxing THF. Alternatively alcohol 26 can be prepared with high enantiomeric excess form from cinnamyl alcohols using Furukawa type chemistry and chiral ligands (*J. Am. Chem. Soc.* 1994, 2651, *Tetrahedron Letters* 1992, 2575). Oxidation of alcohol 26 to give aldehyde 27 can be achieved using standard oxidative methods such as Swern Oxidation, PCC or $MnO_2$. Reductive amination of aldehyde 27 can be achieved using standard procedures to give amines 28. A variety of conditions for palladium mediated couplings can be used to couple 28 with, for example a boronic acid substrate or amine substrate to give compounds of formula (I). Sulfonamides 32 are also suitable substrates for palladium mediated couplings. To those skilled in the art it will be apparent that a range of metal catalysed couplings can be affected on this substrate to give an extensive range of substituents at $R^6$ and $R^{12}$.

Alternatively, ester 5 can be hydrolysed to acid 29 by using known procedures and then reacted with airline 7 to offer amides 30 using aforementioned reagents and techniques. A variety of conditions for palladium mediated couplings can be used to couple 30 with, for example a boronic acid substrate or amine substrate to give amides 31 or 33 via reaction with sulphonamides 32. Amides 31 and 33 can be reduced by use of borane tetrahydrofuran complex or other aforementioned reagents to provide compounds of formula (I).

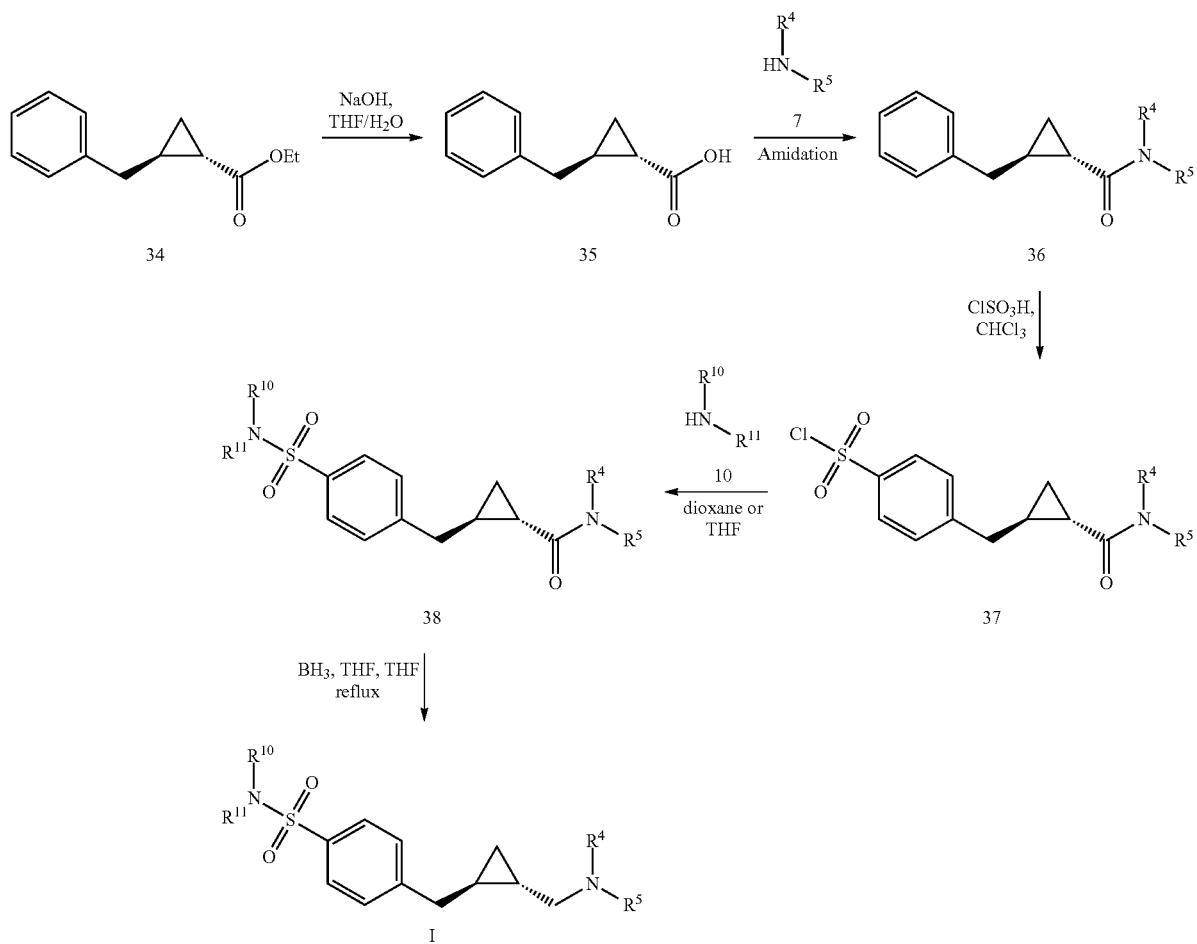

Scheme G

Scheme G outlines another route to the synthesis of compounds of formula (I) from commercially available ester 34. Ester 34 can be hydrolysed to acid 35 by using known procedures and then reacted with amine 7 to offer amides 36 using aforementioned reagents and techniques. Amide 36 can be converted to sulfonyl chloride 37, through treatment with chlorosulfonic acid, and subsequently allowed to react with amine 10 to generate sulfonamides 38. Amides 38 can be reduced by use of borane tetrahydrofuran complex or other afore mentioned reagents to provide compounds of formula (I).

Another variation is to add, remove or modify the substituents of the product to form new derivatives. This could be achieved again by using standard techniques for functional group inter-conversion, well known in the industry such as those described in Comprehensive Organic Transformations: A Guide to Functional Group Preparations by Larock R C, New York, VCH Publishers, Inc. 1989.

Examples of possible functional group inter-conversions are: —C(O)NRR' from —$CO_2CH_3$ by heating with or without catalytic metal cyanide, e.g. NaCN, and HNRR' in CH₃OH; —OC(O)R from —OH with e.g., ClC(O)R' in pyridine; —NR—C(S)NR'R" from —NHR with an alkylisothiocyanate or thiocyanic acid; —NRC(O)OR from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R") SR''' with H₃NR⁺OAc⁻ by heating in alcohol; —C(NR'R") SR from —C(S)NR'R" with R—I in an inert solvent, e.g. acetone; —C(S)NR'R" (where R' or R" is not hydrogen) from —C(S)NH₂ with HNR'R"; —C(=NCN)—NR'R" from —C(=NR'R")—SR with NH₂CN by heating in anhydrous alcohol, alternatively from —C(=NH)—NR'R" by treatment with BrCN and NaOEt in EtOH; —NR—C(=NCN)SR from —NHR' by treatment with (RS)₂C=NCN; —NR"SO₂R from —NHR' by treatment with ClSO₂R by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —NRSO₂CF₃ from —NHR with triflic anhydride and base, —CH(NH₂)CHO from —CH(NH₂)C(O)OR' with Na(Hg) and HCl/EtOH; —CH₂C(O)OH from C(O)OH by treatment with SOCl₂ then CH₂N₂ then H₂O/Ag₂O; —C(O)OH from —CH₂C(O)OCH₃ by treatment with PhMgX/HX then acetic anhydride then CrO₃; R—OC(O)R' from RC(O)R' by R"CO₃H; —CCH₂OH from —C(O)OR' with Na/R'OH; —CHCH₂ from —CH₂CH₂OH by the Chugaev reaction; —NH₂ from —C(O)OH by the Curtius reaction; —NH₂ from —C(O)NHOH with TsCl/base then H₂O; —CHC(O)CHR from —CHCHOHCHR by using the Dess-Martin Periodinane regent or CrO₃/aqH₂SO₄/acetone; —C₆H₅CHO from —C₆H₅CH₃ with CrO₂Cl₂; —CHO from —CN with SnCl₂/HCl; —CN from —C(O)NHR with PCl₅; —CH₂R from —C(O)R with N₂H₄/KOH; —S(O)₂R from —SR with mCPBA.

In order that the present invention may be more readily understood, we provide the following non-limiting examples.

EXAMPLES—SYNTHETIC PROCEDURE

All anhydrous solvents were commercially obtained and stored in Sure-Seal bottles under nitrogen. All other reagents and solvents were purchased as the highest grade available and used without further purification. Thin-layer chromatography (TLC) analysis of reaction mixtures was performed using Merck silica gel 60 F254 TLC plates and visualized using ultraviolet light. Silica gel 60 (40-63 μm, Merck) was used for flash chromatography. Melting points were measured using an Electrothermal 1002 apparatus and were uncorrected. ¹H NMR (300 MHz) and ¹³C NMR (75 MHz) spectra were obtained on a Bruker Advance 300 NMR spectrometer using residual signal of deuterated NMR solvent as internal reference. Mass spectral data and purity of all compounds were acquired on an Agilent LCMS-Ion Trap-1200 Series. Mass spectra were obtained on an Agilent Ion Trap applying electrospray ionization (ESI). Purity of all compounds was obtained using a Nucleodur 3 μm 4.6×150 mm reverse-phase column. The eluent was a linear gradient with a flow rate of 1.3 mL/min from 95% A and 5% B to 5% A and 95% B in 8.5 min (solvent A, H₂O with 0.1% HCO₂H; solvent B, acetonitrile with 0.1% HCO₂H). The compounds were detected at their maximum of absorbance.

In the examples below, in case the structures contain one or more stereogenic centres, the respective structure is depicted in an arbitrary absolute configuration. These structures depict single enantiomers as well as mixtures of enantiomers in all ratios, and/or mixtures of diastereoisomers in all ratios.

General Procedures

General Procedure A: Aldol Condensation to α,β-Unsaturated Esters

A solution of the aldehyde (1.0 equiv.) and monoethyl malonate (1.3 equiv.) in anhydrous pyridine (5 equiv.) containing piperidine (0.1 equiv.) was refluxed for 12 h under an argon atmosphere. The reaction mixture was cooled to room temperature, quenched with 2N HCl, and extracted with ether. The extracts were washed with water, saturated NaHCO₃, and brine. The organic solution was dried over Na₂SO₄ and concentrated in vacuo. The crude mixture was purified by column chromatography (SiO₂, cyclohexane/CH₂Cl₂) to furnish the pure α,β-unsaturated ester.

General Procedure B: Cyclopropanation of α,β-Unsaturated Esters

To a suspension of the alkylphosphonium halide (1.2 equiv.) in anhydrous THF (0.3 M) at −78° C. was added n-BuLi (2.0 M in cyclohexane, 1.1 equiv.) under an argon atmosphere. The resulting mixture was warmed to 0° C. and stirred for 30 min. The reaction mixture was cooled to −78° C. followed by the addition of a solution of the α,β-unsaturated ester (1.0 equiv.) in anhydrous THF (0.5 M). The reaction mixture was stirred for 2 h at 0° C., then slowly warmed to ambient temperature and stirred overnight. The solution was poured onto 1N HCl. The aqueous layer was extracted with ethyl acetate and the combined organic layers were sequentially washed with saturated NaHCO₃, brine, dried over Na₂SO₄, and concentrated in vacuo. The crude cyclopropane was purified by column chromatography (SiO₂, cyclohexane/CH₂Cl₂) to furnish the pure cyclopropyl ester.

General Procedure C: Saponification of Esters

To the ester (1.0 equiv.) in a solution of THF:water (1:4) (0.4 M), was added NaOH (1.1 equiv.). The mixture was stirred overnight at 60° C. followed by removal of the volatiles in vacuo. The remaining aqueous solution was acidified with 1N HCl and then twice extracted with ethyl acetate. The organic extracts were combined and washed with brine, dried over Na₂SO₄ and concentrated in vacuo to furnish the pure carboxylic acid.

General Procedure D: Amide Bond Formation through Acid Chloride (Thionyl Chloride Derived) Intermediates To the carboxylic acid (1.0 equiv.) was added thionyl chloride (10.0 equiv.) at 0° C. and 2 drops of anhydrous DMF under an argon atmosphere. The mixture was stirred for 2 h at room temperature before the mixture was concentrated in vacuo. Co-evaporation with toluene, in vacuo, was used to remove the remaining thionyl chloride. The crude acid chloride was dissolved in anhydrous DCM under an argon atmosphere, cooled to 0° C. and Et₃N (5.0 equiv.) was added followed by the addition of aniline/amine (1.0 equiv.). The mixture was stirred for 16 h at ambient temperature, after this time reaction mixture was concentrated in vacuo and the crude residue directly purified by column chromatography (SiO₂, cyclohexane/ethyl acetate) to furnish the pure amide.

General Procedure E: Formation of Sulfonamides

Chlorosulfonic acid (5-16 equiv.) was added drop-wise at 0° C. to a solution of the arene (1.0 equiv.) in chloroform (0.5 M) under an argon atmosphere. The reaction mixture was stirred at rt until complete conversion to sulfonyl chloride was achieved, then poured into a ice/brine mixture. The phases were separated and the aqueous layer extracted with Et₂O twice. The combined organic extracts were dried over Na₂SO₄, and concentrated in vacuo. The crude sulfonyl chloride was dissolved in a 0.5 M solution of amine in 1,4-dioxane (10.0 equiv.), stirred at ambient temperature for 46 min and evaporated to dryness under vacuum. The crude sulfonamide was purified by column chromatography (SiO₂, cyclohexane/ethyl acetate then EtOAc/MeOH) or triturated with EtOAc/MeOH to give the pure sulfonamide.

General Procedure F: Reduction of Amides to Amines

To the amide (1.0 equiv.), as a solution in anhydrous THF (0.5 M) at 0° C. under an argon atmosphere was added, drop-wise, a 1M solution of BH₃ in THF (3.0-6.0 equiv.). The mixture was stirred for 1 h at room temperature and then 3 h at reflux. The reaction mixture was cooled to 0° C. and HCl 1N (5.0 equiv.) was added carefully. The mixture was then stirred at reflux for 1 h. After cooling to ambient temperature, the mixture was neutralized with NaOH 1N and extracted with ethyl acetate. The combined organic phases were dried (MgSO₄), filtered and concentrated in vacuo. The crude residue was purified by column chromatography (SiO₂, cyclohexane/ethylacetate) to furnish the desired amine.

General Procedure G: Reduction of Esters to Alcohols

The ester (1 equiv.) was suspended in anhydrous Et₂O (0.1 M) under a N₂ atmosphere and was cooled to 0° C. LiAlH₄ (2 equiv.) was added in one portion and the mixture was allowed to stir at 0° C. for 20 minutes before warming to ambient temperature. Once the reaction was deemed to be complete by LCMS analysis the reaction mixture was cooled to 0° C. and potassium sodium tartrate tetrahydrate 1.0 M solution (~30 ml) was added slowly. The mixture was left to stir at ambient temperature for 1 h. before neutralisation with 2 M aq. HCl solution. The mixture was extracted with EtOAc (×4) and the organic extracts were washed with brine (×2) before being dried over MgSO₄ and concentrated in vacuo. The crude residue was purified by column chromatography (SiO₂, cyclohexane/CH₂Cl₂) to furnish the desired alcohol.

General Procedure H: Oxidation of Alcohols to Aldehydes Using PCC

A solution of alcohol (1.0 equiv.) in anhydrous dichloromethane (0.2 M) under an argon atmosphere was rapidly added to a slurry of pyridinium chlorochromate (1.5 equiv.) in anhydrous dichloromethane (0.3 M) and this mixture was stirred at ambient temperature for 2 h. Diethyl ether was added and the mixture was passed through Celite, eluting with diethyl ether. The filtrate was concentrated in vacuo and the crude residue was purified by column chromatography (SiO₂, cyclohexane/CH₂Cl₂) to furnish the desired aldehyde.

General Procedure I: Reductive Amination of Aldehydes

To amine (1.0 equiv.) and aldehyde (1.0 equiv.) in anhydrous dichloromethane (0.12 M) under an argon atmosphere, was added a catalytic amount of acetic acid. The mixture was stirred at ambient temperature for 12 h before addition of NaBH(OAc)₄ (2.0 equiv.). The reaction mixture was stirred at ambient temperature for 2 h, the solution was then concentrated in vacuo and the crude residue was purified by column chromatography (SiO₂, cyclohexane/CH₂Cl₂) to furnish the desired amine.

General Procedure J: Amide Bond Formation through Acid Chloride (Derived from Oxalyl Chloride) Intermediates To a solution of the acid (1 equiv.) in anhydrous dichloromethane (0.4 M) under an atmosphere of N₂ at 0° C., was added DMF (cat.). A solution of oxalyl chloride in anhydrous dichloromethane (1.28 M) was added drop-wise. The reaction mixture was stirred for 1 h at 0° C. before warming to RT and stirring for a further 1 h. The dichloromethane was removed In vacuo or by evaporation under a steady flow of N₂. The crude material was taken up in anhydrous Et₂O (0.4 M), under an atmosphere of N₂, and cooled to 0° C. A solution of amine (1.05 equiv.) and NEt₃ (1 equiv.) in anhydrous Et₂O (0.47 M amine) was added drop-wise. Upon completion of the reaction as determined by LCMS analysis (30 min.-1 h) the reaction was quenched by addition of H₂O and the product was extracted into EtOAc (3×), dried (MgSO₄ or Na₂SO₄) and concentrated in vacuo. The crude residue could be used as is or purified by column chromatography (SiO₂, EtOAc/hexane) to give the desired amide Intermediate A: ±trans N-(5-chloro-2-methoxyphenyl)-2-phenylcyclopropanecarboxamide

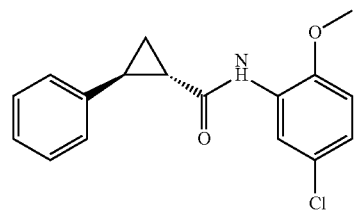 [SMILES: COc1ccc(Cl)cc1NC(=O)[C@H]1C[C@@H]1c1ccccc1]

2-phenylcyclopropanecarboxylic acid (200 mg, 1.23 mmol) and 5-chloro-2-methoxyaniline (194 mg, 1.23 mmol) were reacted as described under General Procedure D to furnish the title compound (328 mg, 88%) as a white solid. ESIMS m/z [M+H]⁺ 302.3.

Intermediate B: ±trans N-(5-chloro-2-methoxyphenyl)-2-(4-sulfamoylphenyl)cyclopropanecarboxamide

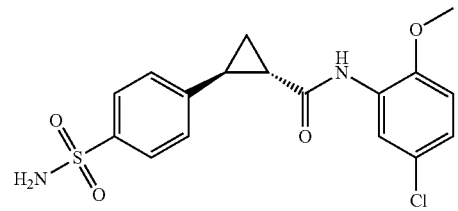 [SMILES: COc1ccc(Cl)cc1NC(=O)[C@H]1C[C@@H]1c1ccc(S(N)(=O)=O)cc1]

Intermediate A (323 mg, 1.09 mmol) and ammonia (excess) were, reacted as described under General Procedure E to furnish the title compound (244 mg, 60%) as a white solid. ESIMS m/z [M+H]⁺ 381.0.

Intermediate C: ±trans N-(4-fluorophenyl)-2-phenylcyclopropanecarboxamide

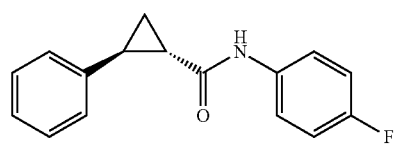 [SMILES: O=C(Nc1ccc(F)cc1)[C@H]1C[C@@H]1c1ccccc1]

2-phenylcyclopropanecarboxylic acid (200 mg, 1.23 mmol) and 4-fluoroaniline (144 mg, 1.30 mmol) were reacted as described under General Procedure D to furnish the title compound (297 mg, 94%) as a white solid. ESIMS m/z [M+H]+ 256.2.

Intermediate D: ±trans N-(4-fluorophenyl)-2-(4-sulfamoylphenyl)cyclopropanecarboxamide

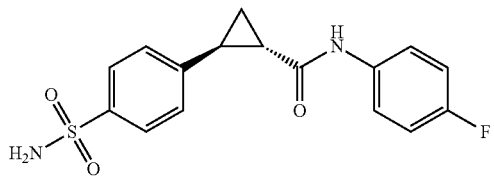 [SMILES: NS(=O)(=O)c1ccc([C@H]2C[C@@H]2C(=O)Nc2ccc(F)cc2)cc1]

Intermediate C (281 mg, 1.10 mmol) and ammonia (excess) were reacted as described under General Procedure E to furnish the title compound which was used crude in subsequent synthetic steps. ESIMS m/z [M+H]+ 335.2.

Intermediate E: ±trans N-(3,4-difluorophenyl)-2-phenylcyclopropanecarboxamide

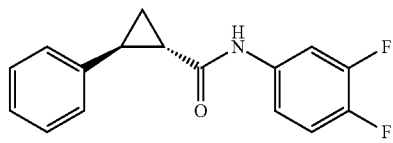 [SMILES: O=C(Nc1ccc(F)c(F)c1)[C@H]1C[C@@H]1c1ccccc1]

2-phenylcyclopropanecarboxylic acid (200 mg, 1.23 mmol) and 3,4-difluoroaniline (167 mg, 1.30 mmol) were reacted as described under General Procedure D to furnish the title compound (291 mg, 86%) as a white solid. ESIMS m/z [M+H]+ 274.2.

Intermediate F: ±trans N-(3,4-difluorophenyl)-2-(4-sulfamoylphenyl)cyclopropanecarboxamide

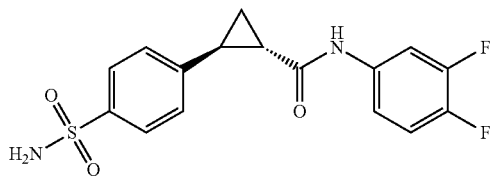 [SMILES: NS(=O)(=O)c1ccc([C@H]2C[C@@H]2C(=O)Nc2ccc(F)c(F)c2)cc1]

Intermediate E (279 mg, 1.02 mmol) and ammonia (excess) were reacted as described under General Procedure E to furnish the title compound which was used crude in subsequent synthetic steps. ESIMS m/z [M+H]+ 353.0.

Intermediate G: ±trans ethyl 2,2-dimethyl-3-phenylcyclopropanecarboxylate

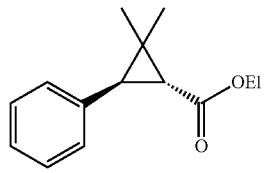

Isopropyltriphenylphosphonium iodide (21.6 g, 50 mmol) and ethyl cinnamate (8.81 g, 50 mmol) were reacted as described under General Procedure B to furnish the title compound (6.58 g, 60%) as a colorless oil. ESIMS m/z [M+H]+ 219.3.

Intermediate H: ±trans 2,2-dimethyl-3-phenylcyclopropanecarboxylic acid

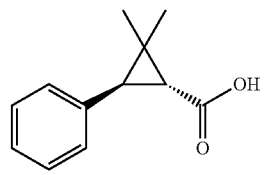

Intermediate G (6.58 g, 30.1 mmol) was reacted as described under General Procedure C to furnish the title compound (5.15 g, 90%) as a white solid ESIMS m/z [M−H]− 189.2.

Intermediate I: ±trans N-(5-chloro-2-methoxyphenyl)-2,2-dimethyl-3-phenylcyclopropanecarboxamide

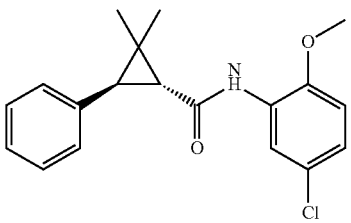 [SMILES: COc1ccc(Cl)cc1NC(=O)[C@@H]1[C@@H](c2ccccc2)C1(C)C]

Intermediate H (1.00 g, 5.3 mmol) and 5-chloro-2-methoxyaniline (1.00 g, 6.3 mmol) were reacted as described under General Procedure D to furnish the title compound (1.02 g, 59%) as a white solid. Mp 155-157° C. ESIMS m/z [M+H]+ 330.1.

Intermediate J: ±trans N-(5-chloro-2-methoxyphenyl)-2,2-dimethyl-3-(4-sulfamoylphenyl)cyclopropanecarboxamide

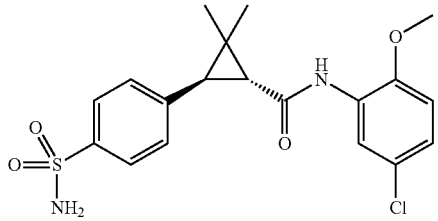 [SMILES: COc1ccc(Cl)cc1NC(=O)[C@@H]1[C@@H](c2ccc(S(N)(=O)=O)cc2)C1(C)C]

Intermediate I (430 mg, 1.30 mmol) was reacted as described under General Procedure E to give the title compound (357 mg, 67%) as a white solid. Mp 129-133° C. ESIMS m/z [M+H]$^+$ 409.1.

Intermediate K: ±trans 2,2-dimethyl-N,3-diphenylcyclopropanecarboxamide

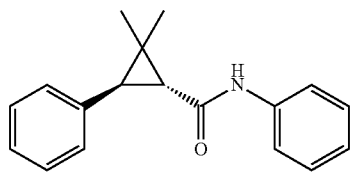 [SMILES: CC1(C)[C@H](C(=O)Nc2ccccc2)[C@H]1c1ccccc1]

Intermediate H (500 mg, 2.6 mmol) and aniline (294 mg, 3.2 mmol) were reacted as described under General Procedure D to give the title compound (655 mg, 94%) as a white solid. Mp 143-145° C. ESIMS m/z [M+H]$^+$ 266.2.

Intermediate L: ±trans 2,2-dimethyl-N-phenyl-3-(4-sulfamoylphenyl)cyclopropanecarboxamide

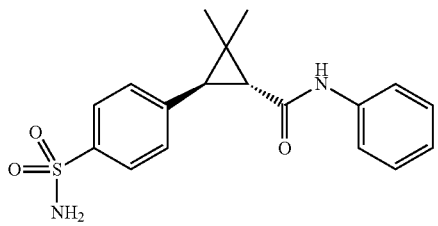 [SMILES: CC1(C)[C@H](C(=O)Nc2ccccc2)[C@H]1c1ccc(S(N)(=O)=O)cc1]

Intermediate K (655 mg, 2.5 mmol) was reacted as described under General Procedure E to give the title compound (270 mg, 32%) as a white solid. ESIMS m/z [M+H]$^+$ 345.2.

Intermediate M: ±trans N,2,2-trimethyl-N,3-diphenylcyclopropanecarboxamide

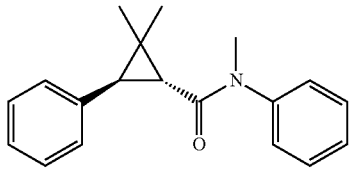 [SMILES: CN(C(=O)[C@@H]1[C@@H](c2ccccc2)C1(C)C)c1ccccc1]

Intermediate H (500 mg, 2.6 mmol) and N-methyl aniline (338 mg, 3.2 mmol) were reacted as described under General Procedure D to give the title compound (712 mg, 97%) as a yellow solid. Mp 59-61° C. ESIMS m/z [M+H]$^+$ 280.2.

Intermediate N: ±trans N,2,2-trimethyl-N-phenyl-3-(4-sulfamoylphenyl)cyclopropanecarboxamide

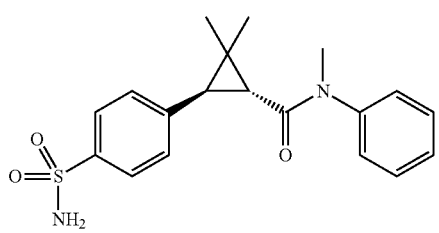 [SMILES: CN(C(=O)[C@@H]1[C@@H](c2ccc(S(N)(=O)=O)cc2)C1(C)C)c1ccccc1]

Intermediate M (700 mg, 2.5 mmol) reacted as described under General Procedure E to give the title compound (400 mg, 44%) as a white solid. ESIMS m/z [M+H]$^+$ 359.2.

Intermediate O: ±trans N-(5-chloro-2-methoxyphenyl)-N,2,2-trimethyl-3-phenylcyclopropanecarboxamide

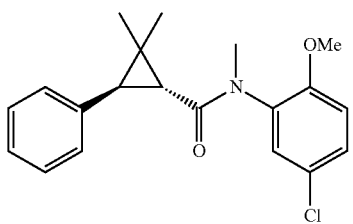 [SMILES: COc1ccc(Cl)cc1N(C)C(=O)[C@@H]1[C@@H](c2ccccc2)C1(C)C]

To a stirred suspension of sodium hydride (60% suspension in mineral oil, 175 mg, 4.4 mmol) in dry DMF (10 ml) at 0° C., under an argon atmosphere was added Intermediate I (960 mg, 2.9 mmol). The solution was then stirred at ambient temperature for 20 minutes at which point iodomethane (0.72 ml, 11.6 mmol) was slowly added at 0° C. and the reaction mixture stirred at ambient temperature for 12 h. Solvent was then removed in vacuo and the crude oil was purified by column chromatography (SiO$_2$, cyclohexane/AcOEt 100:0→80:20) to give the title compound (964 mg, 96%) as a yellow oil. Compound appears as rotational isomers in a 1:1 ratio, ESIMS m/z [M+H]$^+$ 344.2.

Intermediate P: ±trans N-(5-chloro-2-methoxyphenyl)-N,2,2-trimethyl-3-(4-sulfamoylphenyl)cyclopropanecarboxamide

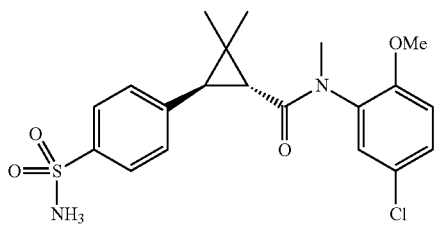 [SMILES: COc1ccc(Cl)cc1N(C)C(=O)[C@@H]1[C@@H](c2ccc(S(N)(=O)=O)cc2)C1(C)C]

Intermediate O (749 mg, 2.2 mmol) reacted as described under General Procedure E to give the title compound (230 mg, 25%) as a white solid. ESIMS m/z [M+H]$^+$ 423.2.

Intermediate Q: ±trans ethyl 2-phenylspiro[2.4]heptane-1-carboxylate

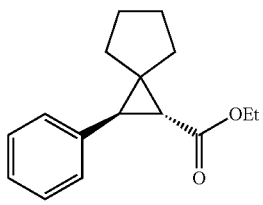 [SMILES: CCOC(=O)[C@@H]1[C@@H](c2ccccc2)C12CCCC2]

Cyclopentyltriphenylphosphonium bromide (10.3 g, 25 mmol) and ethyl cinnamate (4.40 g, 25 mmol) were reacted as described under General Procedure B to furnish the title compound (3.72 g, 61%) as a colorless oil. $^1$H NMR (300 MHz, CDCl$_3$) δ 7.32-7.11 (m, 5H), 4.22-4.13 (m, 2H), 2.77 (d, 1H), 2.15 (d, 1H), 1.91-1.85 (m, 2H), 1.72-1.27 (m, 9H).

Intermediate R: ±trans 2-phenylspiro[2.4]heptane-1-carboxylic acid

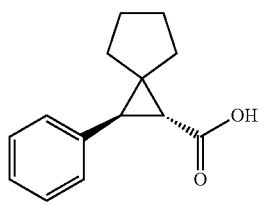 [SMILES: O=C(O)[C@@H]1[C@@H](c2ccccc2)C12CCCC2]

Intermediate Q (3.72 g, 16.2 mmol) was reacted as described under General Procedure C to furnish the title compound (3.19 g, 96%) as a white solid. $^1$H NMR (300 MHz, CDCl$_3$) δ 7.33-7.11 (m, 5H), 2.83 (d, 1H), 2.17 (d, 1H), 1.97-1.32 (m, 8H).

Intermediate S: ±trans N-(5-chloro-2-methoxyphenyl)-2-phenylspiro[2.4]heptane-1-carboxamide

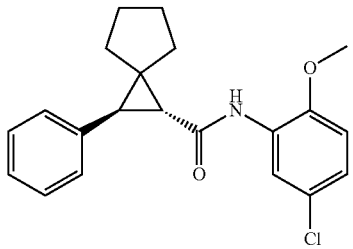 [SMILES: COc1ccc(Cl)cc1NC(=O)[C@@H]1[C@@H](c2ccccc2)C12CCCC2]

Intermediate R (400 mg, 1.85 mmol) and 5-chloro-2-methoxyaniline (291 mg, 1.85 mmol) were reacted as described under General Procedure D to furnish the title compound (580 mg, 85%) as a beige solid. Mp 133-135° C. ESIMS m/z [M+H]$^+$ 356.2.

Intermediate T: ±trans N-(5-chloro-2-methoxyphenyl)-2-(4-sulfamoylphenyl)spiro[2.4]heptane-1-carboxamide

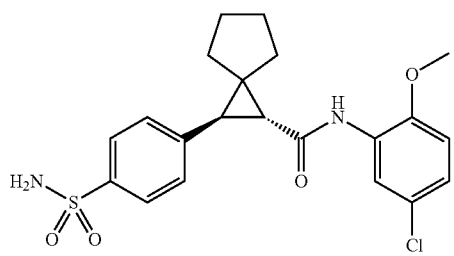 [SMILES: COc1ccc(Cl)cc1NC(=O)[C@@H]1[C@@H](c2ccc(S(N)(=O)=O)cc2)C12CCCC2]

Intermediate S (200 mg, 0.56 mmol) was reacted as described under General Procedure E to give the title compound (140 mg, 58%) as a white solid. Mp 210-212° C. ESIMS m/z [M+H]$^+$ 435.2.

Intermediate U: ±trans N-(2,6-dimethoxypyridin-3-yl)-2-phenylspiro[2.4]heptane-1-carboxamide

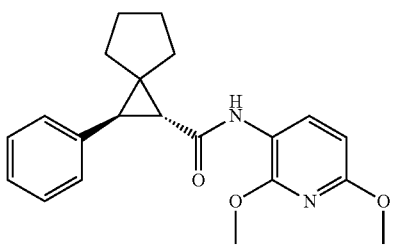 [SMILES: COc1ccc(NC(=O)[C@@H]2[C@@H](c3ccccc3)C23CCCC3)c(OC)n1]

Intermediate Q (300 mg, 1.39 mmol) and 2,6-dimethoxypyridin-3-ylamine (214 mg, 1.39 mmol) were reacted as described under General Procedure D to furnish the title compound (260 mg, 52%) as a purple solid. Mp 131-133° C. ESIMS m/z [M+H]$^+$ 353.2.

Intermediate V: ±trans N-(2,6-dimethoxypyridin-3-yl)-2-(4-sulfamoylphenyl)spiro[2.4]heptane-1-carboxamide

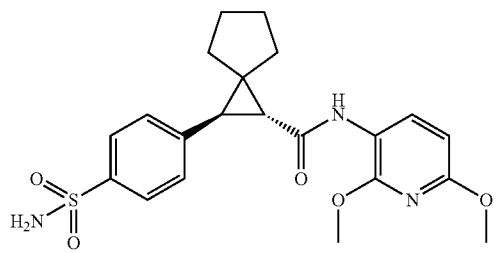 [SMILES: COc1ccc(NC(=O)[C@@H]2[C@@H](c3ccc(S(N)(=O)=O)cc3)C23CCCC3)c(OC)n1]

Intermediate U (170 mg, 0.47 mmol) was reacted as described under General Procedure E to give the title compound (105 mg, 63%) as a white solid. Mp 112-115° C. ESIMS m/z [M+H]$^+$ 432.3.

Intermediate W: ±trans (2,2-dimethyl-3-phenylcyclopropyl)methanol

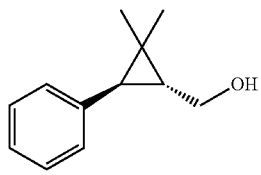

Intermediate G (2.18 g, 10 mmol) was reacted as described under General Procedure G to furnish the title compound (1.56 g, 88%) as a colourless oil. $^1$H NMR (300 MHz, CDCl$_3$) δ 7.30-7.24 (m, 3H), 7.20-7.15 (m, 2H), 3.90 (dd, 1H), 3.71 (dd, 1H), 1.76 (d, 1H), 1.44 (td, 1H), 1.39 (s, 1H), 1.30 (s, 3H), 0.86 (s, 3H).

Intermediate X: ±trans 2,2-dimethyl-3-phenylcyclopropanecarbaldehyde

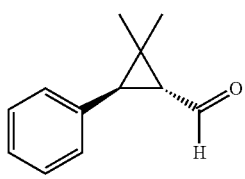

Intermediate W (1.0 g, 5.7 mmol) was reacted as described under General Procedure H to furnish the title compound (765 mg, 76%) as a colourless oil. $^1$H NMR (300 MHz, CDCl$_3$) δ 9.58 (d, 1H) 7.33-7.22 (m, 3H), 7.19-7.13 (m, 2H), 2.95 (d, 1H), 2.18 (t, 1H), 1.45 (s, 3H), 0.98 (s, 3H).

Intermediate Y: ±trans N-(5-fluoropyridin-3-yl)-2,2-dimethyl-3-phenylcyclopropanecarboxamide

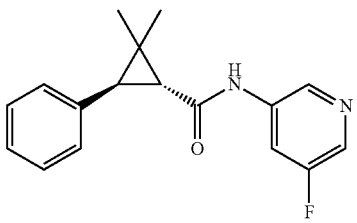 [SMILES: CC1(C)[C@H](C(=O)Nc2cncc(F)c2)[C@H]1c1ccccc1]

Intermediate H (0.200 g, 1.05 mmol) and 3-amino-5-fluoropyridine (0.124 g, 1.10 mmol) were reacted as described under General Procedure J to furnish the title compound (287 mg, 96%) which was used crude in the next step. ESIMS m/z [M+H]$^+$ 285.2.

Intermediate Z: ±trans N-(5-fluoropyridin-3-yl)-2,2-dimethyl-3-(4-sulfamoylphenyl)cyclopropanecarboxamide

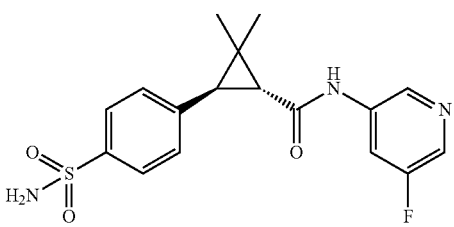 [SMILES: CC1(C)[C@H](C(=O)Nc2cncc(F)c2)[C@H]1c1ccc(S(N)(=O)=O)cc1]

Intermediate Y (285 mg) was reacted as described under General Procedure E to furnish the title compound (385 mg) which was used crude in the next step. ESIMS m/z [M+H]$^+$ 364.0.

Intermediate AA: ±trans 2,2-dimethyl-3-phenyl-N-[2-(trifluoromethyl)pyridin-4-yl]cyclopropanecarboxamide

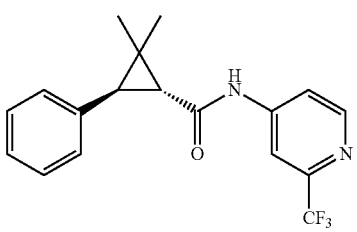 [SMILES: CC1(C)[C@H](C(=O)Nc2ccnc(C(F)(F)F)c2)[C@H]1c1ccccc1]

Intermediate H (203 mg, 1.07 mmol) and 4-amino-2-(trifluoromethyl)pyridine (182 mg, 1.12 mmol) were reacted as described under General Procedure J to furnish the title compound (375 mg) which was used crude in the next step. ESIMS m/z [M+H]$^+$ 335.2.

Intermediate AB: ±trans 2,2-dimethyl-3-(4-sulfamoylphenyl)-N-[2-(trifluoromethyl)pyridin-4-yl]cyclopropanecarboxamide

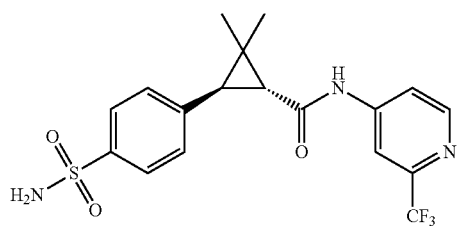 [SMILES: CC1(C)[C@H](C(=O)Nc2ccnc(C(F)(F)F)c2)[C@H]1c1ccc(S(N)(=O)=O)cc1]

Intermediate AA (375 mg) was reacted as described under General Procedure E to furnish the title compound (423 mg) which was used crude in the next step. ESIMS m/z [M+H]$^+$ 414.0.

Intermediate AC: ±trans 2-phenyl-N-[5-(trifluoromethyl)pyridin-2-yl]cyclopropanecarboxamide

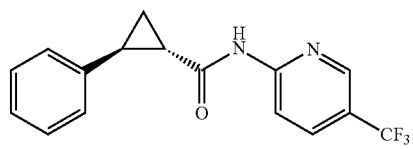 [SMILES: O=C(Nc1ccc(C(F)(F)F)cn1)[C@H]1C[C@@H]1c1ccccc1]

2-Phenylcyclopropanecarboxylic acid (48 mg, 0.30 mmol) and 2-amino-5-(trifluoromethyl)pyridine (51 mg, 0.31 mmol) were reacted as described under General Procedure J to furnish the title compound (48 mg, with a major impurity still present) after purification by pTLC (50% DCM/hexane). Compound was used crude in the next step. ESIMS m/z [M+H]$^+$ 307.3.

Intermediate AD: ±trans 2-(4-sulfamoylphenyl)-N-[5-(trifluoromethyl)pyridin-2-yl]cyclopropanecarboxamide

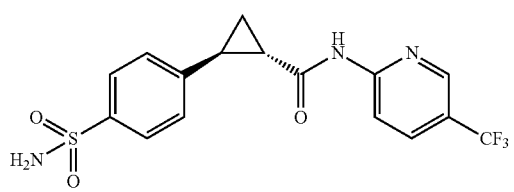 [SMILES: NS(=O)(=O)c1ccc([C@H]2C[C@@H]2C(=O)Nc2ccc(C(F)(F)F)cn2)cc1]

Intermediate AC (48 mg, 0.16 mmol) was reacted as described under General Procedure E to furnish the title compound (51 mg) which was used crude in the next step. ESIMS m/z [M+H]$^+$ 386.0.

Intermediate AE: ±trans N-(4-fluorophenyl)-2,2-dimethyl-3-phenylcyclopropanecarboxamide

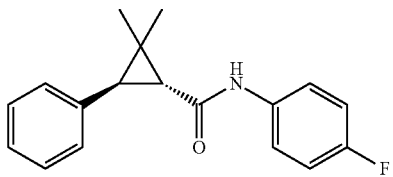 [SMILES: CC1(C)[C@H](C(=O)Nc2ccc(F)cc2)[C@H]1c1ccccc1]

Intermediate H (201 mg, 1.06 mmol) and 4-fluoroaniline (123 mg, 1.11 mmol) were reacted as described under General Procedure J to furnish the title compound (265 mg) which was used crude in the next step. ESIMS m/z [M+H]$^+$ 284.2.

Intermediate AF: ±trans N-(4-fluorophenyl)-2,2-dimethyl-3-(4-sulfamoylphenyl)cyclopropanecarboxamide

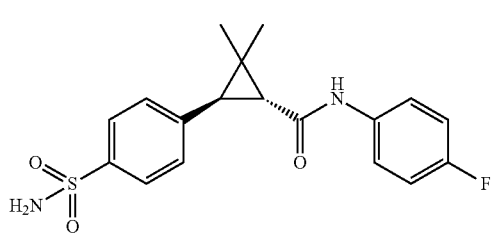 [SMILES: CC1(C)[C@H](C(=O)Nc2ccc(F)cc2)[C@H]1c1ccc(S(N)(=O)=O)cc1]

Intermediate AE (265 mg) was reacted as described under General Procedure E to furnish the title compound which was used crude in the next step. ESIMS m/z [M+H]$^+$ 363.3.

Intermediate AG: ±trans N-(3,4-difluorophenyl)-2,2-dimethyl-3-phenylcyclopropanecarboxamide

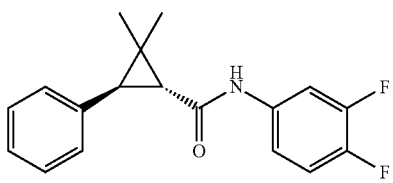 [SMILES: CC1(C)[C@H](C(=O)Nc2ccc(F)c(F)c2)[C@H]1c1ccccc1]

Intermediate H (201 mg, 1.06 mmol) and 3,4-difluoroaniline (143 mg, 1.11 mmol) were reacted as described under General Procedure J to furnish the title compound (270 mg) which was used crude in the next step. ESIMS m/z [M+H]$^+$ 302.3.

Intermediate AH: ±trans N-(3,4-difluorophenyl)-2,2-dimethyl-3-(4-sulfamoylphenyl)cyclopropanecarboxamide

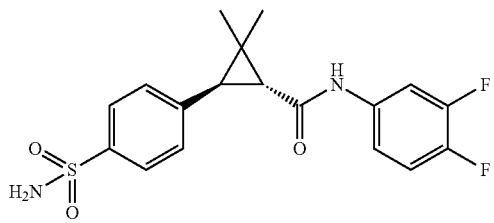 [SMILES: CC1(C)[C@H](C(=O)Nc2ccc(F)c(F)c2)[C@H]1c1ccc(S(N)(=O)=O)cc1]

Intermediate AG (270 mg) was reacted as described under General Procedure E to furnish the title compound which was used crude in the next step. ESIMS m/z [M+H]+ 381.0.

Intermediate AI and Intermediate AJ: (4S)-4-benzyl-3-{[(1S,2S)-2-phenylcyclopropyl]carbonyl)-1,3-oxazolidin-2-one and (4S)-4-benzyl-3-{[(1R,2R)-2-phenylcyclopropyl]carbonyl}-1,3-oxazolidin-2-one

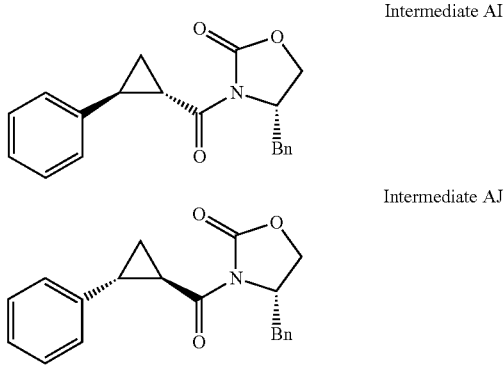

A solution of 2-phenylcyclopropanecarboxylic acid (3.80 g, 23.4 mmol) in anhydrous DCM (40 ml), under an atmosphere of $N_2$, was cooled to 0° C. and DMF (cat.) added. A solution of oxalylchloride (8.92 g, 70.3 mmol) in anhydrous DCM (36 ml) was added drop-wise via a cannula. The solution was stirred at 0° C. for 45 minutes before warming to ambient temperature and stirring for 1 h. The solution was concentrated in vacuo and then taken up in anhydrous THF (35 ml).

Meanwhile, a solution of (S)-4-benzyl-2-oxazolidinone (4.29 g, 23.4 mmol) in anhydrous THF (35 ml), under $N_2$, was cooled to −78° C. A solution of nBuLi in cyclohexane (1.9 M, 12.3 ml, 23.4 mmol) was added drop-wise and stirred for 30 minutes at −78° C. A solution of the crude acid chloride, prepared above, in anhydrous THF, was added via a cannula and the reaction mixture allowed to slowly attain ambient temperature overnight. The following morning the reaction was quenched by addition of $NH_4Cl$ (sat. aq.) and further diluted with $H_2O$. The product was then extracted with EtOAc (2×) and dichloromethane (2×). The pooled organic extracts were dried ($MgSO_4$), filtered and concentrated in vacuo. The isomers were separated via a combination of column chromatography (40% EtOAc/petroleum ether) and fractional crystallisation (first eluting isomer—40% EtOAc/hexane, second eluting isomer—dichloromethane/heptane), yielding Intermediate AI as a white crystalline solid (1.9 g, 50%) and Intermediate AJ as a white crystalline solid (1.4 g, 37%).

Intermediate AI (first eluting): $^1$H NMR (300 MHz, $CDCl_3$) δ 7.38-7.15 (m, 10H), 4.70 (dq, 1H), 4.24-4.16 (m, 2H), 3.60-3.54 (m, 1H), 3.32 (dd,), 2.80 (dd, 1H), 2.73-2.66 (m, 1H), 1.81 (dq, 1H), 1.53-1.47 (m, 1H). ESIMS m/z [M+H]+ 322.3.

Intermediate AJ (second eluting): $^1$H NMR (300 MHz, $CDCl_3$) δ 7.35-7.19 (m, 10H), 4.76-4.68 (m, 1H), 4.26-4.15 (m, 2H), 3.61-3.55 (m, 1H), 3.30 (dd, J=13.5 Hz, 3.3 Hz, 1H), 2.80 (dd, J=13.5, 9.6 Hz, 1H), 2.75-2.70 (m, 1H), 1.77 (dq,), 1.55-1.42 (m, 1H). ESIMS m/z [M+H]+ 322.3.

Note: stereochemistry was assigned to each isomer retrospectively following comparison of optical rotation of Intermediates AK and AL to literature values.

Intermediate AK: (1S,2S)-2-phenylcyclopropanecarboxylic acid

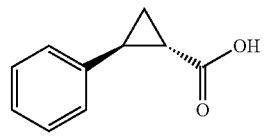 [SMILES: O=C(O)[C@H]1C[C@@H]1c1ccccc1]

A THF:$H_2O$ mixture (3:1 v/v, 40 ml) was added to Intermediate AI (1.88 g, 5.85 mmol) and the mixture allowed to stir for a few minutes to allow almost complete dissolution, before cooling to 0° C. Hydrogen peroxide (35%, 4.5 ml, 46.8 mmol) was added, followed by lithium hydroxide (0.56 g, 23.4 mmol). The reaction mixture was stirred at 0° C. for 30 minutes before warming to ambient temperature and stirring for 1.5 h. The reaction mixture was then cooled to 0° C. and 1.5 M sodium sulphite solution (46.8 mmol) was added and the reaction mixture stirred at 0° C. for 15 minutes before warming to ambient temperature and stirring for another 15 minutes. The aqueous phase was extracted with $Et_2O$ (3×) and then acidified to pH 1 with conc. HCl. The solution was then extracted with $Et_2O$ (4×), and the combined organic extracts dried ($MgSO_4$), filtered and concentrated in vacuo to give Intermediate AK (900 mg, 95%) as a clear viscous oil. $^1$HNMR (300 MHz, $CDCl_3$) δ 7.35-7.09 (m, 5H), 2.61 (ddd, 1H), 1.91 (dq, J=4.8, 3.9, 1H), 1.67 (q, 1H), 1.42 (dq, 1H). ESIMS m/z [M−H]+ 161.2. $[α]_D^{24.5}$ +249.261 (c 0.102, MeOH). Absolute stereochemistry assigned by comparison with literature (JMC 2000, p 3923; JMC 2011, p 957).

Intermediate AL: (1R,2R)-2-phenylcyclopropanecarboxylic acid

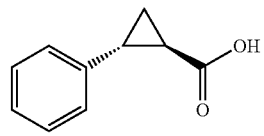 [SMILES: O=C(O)[C@@H]1C[C@H]1c1ccccc1]

Intermediate AJ (1.40 g, 4.37 mmol) was reacted according to the procedure described for Intermediate AK, to yield the title compound with a minor impurity (837 mg) which was used without further purification. $^1$HNMR (300 MHz, CDCl$_3$) δ $^1$HNMR (300 MHz, CDCl$_3$) δ 7.35-7.09 (m, 5H), 2.61 (ddd, 1H), 1.91 (dq, 1H), 1.67 (q, 1H), 1.42 (dq, 1H). ESIMS m/z [M−H]$^+$ 161.2. [α]$_D^{24.4}$ −259.546 (c 0.119, MeOH). Absolute stereochemistry assigned by comparison with literature (JMC 2000, p 3923; JMC 2011, p 957).

Intermediate AM and intermediate AN: (4S)-4-benzyl-3-{[(1R,3R)-2,2-dimethyl-3-phenylcyclopropyl]carbonyl}-1,3-oxazolidin-2-one and (4S)-4-benzyl-3-{[(1S,3S)-2,2-dimethyl-3-phenylcyclopropyl]carbonyl}-1,3-oxazolidin-2-one

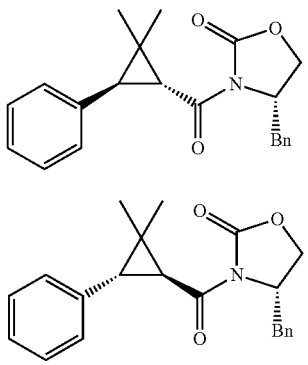

Intermediate AM

Intermediate AN

Intermediate H (1.167 g, 6.13 mmol) was reacted according to the procedure described for Intermediates AI and AJ. The isomes were separated via a combination of column chromatography (1:2:7, Et$_2$O/Hexane/Toluene) and fractional crystallisation of the first eluting isomer only (heptane) (71% overall yield):

Intermediate AM (first eluting): $^1$H NMR (300 MHz, CDCl$_3$) δ 7.38-7.19 (m, 10H), 4.68-4.76 (m, 1H), 4.26-4.16 (m, 2H), 3.38-3.32 (m, 2H), 2.95 (d 1H), 2.77 (dd, 1H), 1.39 (s, 3H), 1.06 (s, 3H). ESIMS m/z [M−H]$^+$ 350.3. Analysis of this isomer by x-ray crystallography enabled absolute stereochemical assignment of Intermediates AM and AN.

Intermediate AN (second eluting): $^1$H NMR (300 MHz, CDCl$_3$) δ 7.37-7.17 (m, 10H), 4.81-4.73 (m, 1H), 4.27-4.17 (m, 2H), 3.42 (d, 1H), 3.34 (dd, 1H), 2.95 (d, 1H), 2.83 (dd, 1H), 1.35 (s, 3H), 1.02 (s, 3H). ESIMS m/z [M−H]$^+$ 350.3.

Intermediate AO: (R,R)-2,2-dimethyl-3-phenylcyclopropanecarboxylic acid

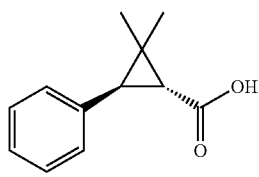

Intermediate AM (1.44 g, 4.11 mmol) was reacted according to the procedure described for Intermediate AK, to yield the title compound (707 mg), which was used without further purification. ESIMS m/z [M−H]$^−$ 189.2.

Intermediate AP: (S,S)-2,2-dimethyl-3-phenylcyclopropanecarboxylic acid

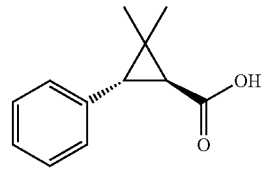

Intermediate AN (450 mg, 1.29 mmol) was reacted according to the procedure described for Intermediate AK, to yield the title compound (187 mg), which was used without further purification. ESIMS m/z [M−H]$^−$ 189.2.

Alternatively, Intermediate H was separated into constituent enantiomers (Intermediate AO and AP) using SFC (Lux C4, CO$_2$/Methanol 17:3, 3 mLmin-1, 35° C., 100 bar), Intermediate AO was the first eluting isomer Rt=2.36 min, 100% ee, [α]$_D^{25.0}$ +27.725° (MeOH, c=1.020), and Intermediate AP the second eluting isomer, Rt=3.01 min, 98.17% ee, [α]$_D^{26.1}$ −27.800° (MeOH, c=1.000). Stereochemistry was confirmed by reacting the second eluting acid (Rt=3.01 min), according to the procedure outlined for Intermediates AI and AJ, to give Intermediate AN which was matched by $^1$H NMR.

Intermediate AQ: (1R,3R)—N-[4-fluoro-2-(trifluoromethyl)phenyl]-2,2-dimethyl-3-phenylcyclopropanecarboxamide

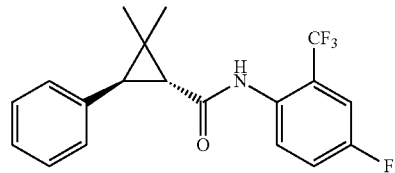 [SMILES: CC1(C)[C@H](C(=O)Nc2ccc(F)cc2C(F)(F)F)[C@H]1c1ccccc1]

Intermediate AO (259 mg, 1.36 mmol) and 2-amino-5-fluorobenzotrifluoride (264 mg, 1.43 mmol) was reacted as described under General Procedure J to furnish the title compound (423 mg) as an off white solid which was used without further purification in the next step. ESIMS m/z [M+H]$^+$ 352.3.

Intermediate AR: (1R,3R)—N-[4-fluoro-2-(trifluoromethyl)phenyl]-2,2-dimethyl-3-(4-sulfamoylphenyl)cyclopropanecarboxamide

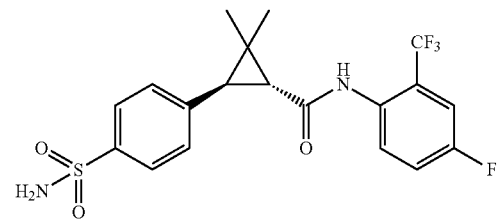 [SMILES: CC1(C)[C@H](C(=O)Nc2ccc(F)cc2C(F)(F)F)[C@H]1c1ccc(S(N)(=O)=O)cc1]

Intermediate AQ (413 mg, 1.18 mmol) was reacted as described under General Procedure E to furnish the title compound (382 mg) which was used without further purification in the next step. ESIMS m/z [M+H]⁺ 431.0.

Intermediate AS: (1R,3R)—N-[5-fluoro-2-(2,2,2-trifluoroethoxy)phenyl]-2,2-dimethyl-3-phenylcyclopropanecarboxamide

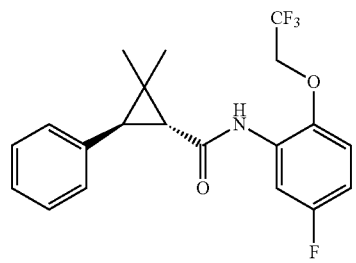 [SMILES: CC1(C)[C@H](C(=O)Nc2cc(F)ccc2OCC(F)(F)F)[C@H]1c1ccccc1]

Intermediate AO (237 mg, 1.25 mmol) and 5-fluoro-2-(2,2,2-trifluoroethoxy)aniline.HCl (321 mg, 1.3 mmol) were reacted as described under General Procedure J (except 2 equiv. of NEt₃ were used) to furnish the title compound (437 mg) of a pale brown oil, which was used without further purification in the next step. ESIMS m/z [M+H]⁺ 382.0.

Intermediate AT: (1R,3R)—N-[5-fluoro-2-(2,2,2-trifluoroethoxy)phenyl]-2,2-dimethyl-3-(4-sulfamoylphenyl)cyclopropanecarboxamide

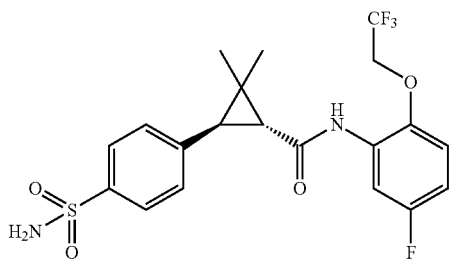 [SMILES: CC1(C)[C@H](C(=O)Nc2cc(F)ccc2OCC(F)(F)F)[C@H]1c1ccc(S(N)(=O)=O)cc1]

Intermediate AS (427 mg, 1.12 mmol) was reacted as described under General Procedure E to furnish the title compound (435 mg) which was used without further purification in the next step. ESIMS m/z [M−H]⁻ 459.2.

Intermediate AU: (1S,3S)—N-[4-fluoro-2-(trifluoromethyl)phenyl]-2,2-dimethyl-3-phenylcyclopropanecarboxamide

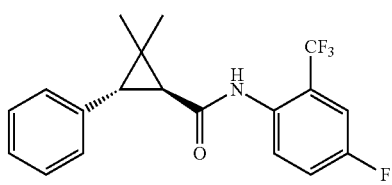 [SMILES: CC1(C)[C@@H](C(=O)Nc2ccc(F)cc2C(F)(F)F)[C@@H]1c1ccccc1]

Intermediate AP (184 mg, 0.969 mmol) and 2-amino-5-fluorobenzotrifluoride (182 mg, 1.02 mmol) were reacted as described under General Procedure J to furnish the title compound (336 mg) as a pale yellow gum which was used without further purification in the next step. ESIMS m/z [M+H]⁺ 352.3.

Intermediate AV: (1S,3S)—N-[4-fluoro-2-(trifluoromethyl)phenyl]-2,2-dimethyl-3-(4-sulfamoylphenyl)cyclopropanecarboxamide

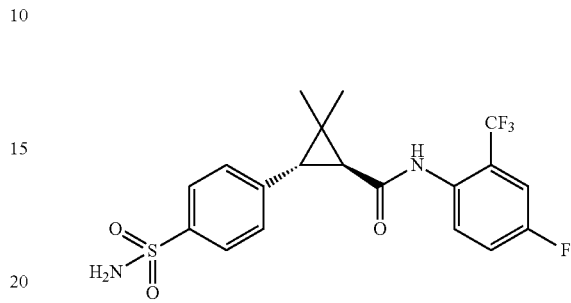

Intermediate AU (331 mg, 0.942 mmol) was reacted as described under General Procedure E to furnish the title compound (308 mg) as a white crystalline solid, which was used without further purification in the next step. ESIMS m/z [M+H]⁺ 431.0.

Intermediate AW: (1R,2R)—N-(4-fluorophenyl)-2-phenylcyclopropanecarboxamide

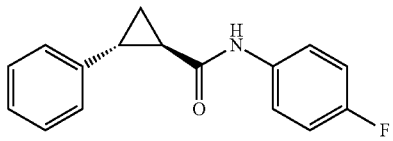 [SMILES: O=C(Nc1ccc(F)cc1)[C@@H]1C[C@H]1c1ccccc1]

Intermediate AL (200 mg, 1.23 mmol) and 4-fluoroaniline (144 mg, 1.30 mmol) were reacted as described under General Procedure J to furnish the title compound which was used without further purification in the next step. ESIMS m/z [M+H]⁺ 256.2.

Intermediate AX: (1R,2R)—N-(4-fluorophenyl)-2-(4-sulfamoylphenyl)cyclopropanecarboxamide

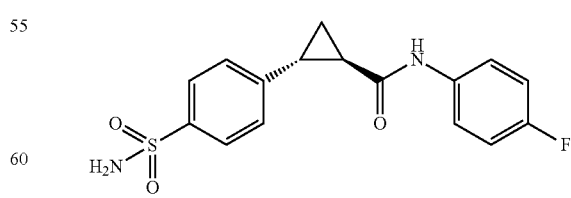

Intermediate AW (300 mg, 1.18 mmol) was reacted as described under General Procedure E to furnish the title compound which was used without further purification in the next step. ESIMS m/z [M−H]⁻ 333.3.

Intermediate AY: (1R,2R)-2-phenyl-N-[5-(trifluoromethyl)pyridin-2-yl]cyclopropanecarboxamide

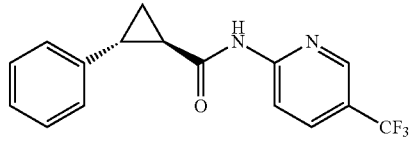 [SMILES: O=C(Nc1ccc(C(F)(F)F)cn1)[C@@H]1C[C@H]1c1ccccc1]

Intermediate AL (250 mg, 1.54 mmol) and 2-amino-5-(trifluoromethyl)pyridine (262 mg, 1.62 mmol) were reacted as described under General Procedure J to furnish the title compound (145 mg, 31%) after purification by column chromatography (15-20% EtOAc/hexane, 3 columns). ESIMS m/z [M−H]⁻ 307.3.

Intermediate AZ: (1R,2R)-2-(4-sulfamoylphenyl)-N-[5-(trifluoromethyl)pyridin-2-yl]cyclopropanecarboxamide

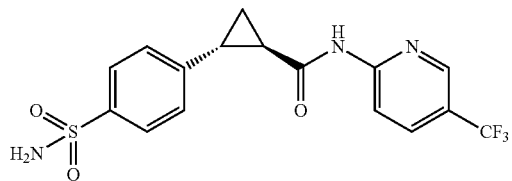 [SMILES: NS(=O)(=O)c1ccc([C@@H]2C[C@H]2C(=O)Nc2ccc(C(F)(F)F)cn2)cc1]

Intermediate AY (140 mg, 0.45 mmol) was reacted as described under General Procedure E to furnish the title compound which was used without further purification in the next step. ESIMS m/z [M−H]⁻ 386.0.

Intermediate BA: (1R,3R)—N-(6-chloro-2-methoxyphenyl)-2,2-dimethyl-3-phenylcyclopropenecarboxamide

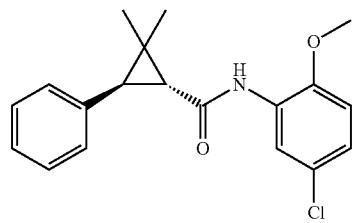 [SMILES: COc1ccc(Cl)cc1NC(=O)[C@@H]1[C@@H](c2ccccc2)C1(C)C]

Intermediate AO (275 mg, 1.45 mmol) and 5-chloro-2-methoxyaniline (239 mg, 1.52 mmol) were reacted as described under General Procedure J to furnish the crude title compound (466 mg) as a colourless oil, which was used without further purification. ESIMS m/z [M+H]⁺ 330.1.

Intermediate BB: (1R,3R)—N-(5-chloro-2-methoxyphenyl)-2,2-dimethyl-3-(4-sulfamoylphenyl)cyclopropanecarboxamide

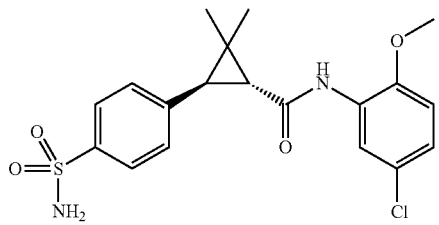 [SMILES: COc1ccc(Cl)cc1NC(=O)[C@@H]1[C@@H](c2ccc(S(N)(=O)=O)cc2)C1(C)C]

Intermediate BA (466 mg) was reacted as described under General Procedure E to give the crude title compound (540 mg) as a white crystalline solid which was used without further purification. ESIMS m/z [M+H]⁺ 409.1.

Intermediate BC: (1S,3S)—N-(5-chloro-2-methoxyphenyl)-2,2-dimethyl-3-phenylcyclopropanecarboxamide

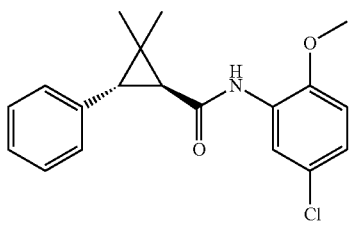 [SMILES: COc1ccc(Cl)cc1NC(=O)[C@H]1[C@H](c2ccccc2)C1(C)C]

Intermediate AP (200 mg, 1.05 mmol) and 5-chloro-2-methoxyaniline (174 mg, 1.1 mmol) were reacted as described under General Procedure J to furnish the crude title compound (347 mg) as an off white crystalline solid, which was used without further purification. ESIMS m/z [M+H]⁺ 330.1.

Intermediate BD: (1R,3R)—N-(5-chloro-2-methoxyphenyl)-2,2-dimethyl-3-(4-sulfamoylphenyl)cyclopropanecarboxamide

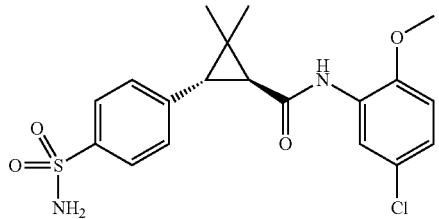 [SMILES: COc1ccc(Cl)cc1NC(=O)[C@H]1[C@H](c2ccc(S(N)(=O)=O)cc2)C1(C)C]

Intermediate BC (347 mg) was reacted as described under General Procedure E to give the title compound (349 mg) as white crystalline solid which was used without further purification. ESIMS m/z [M+H]⁺ 409.1.

Intermediate BE: ±trans N-(5-chloro-2-methylphenyl)-2,2-dimethyl-3-phenylcyclopropanecarboxamide

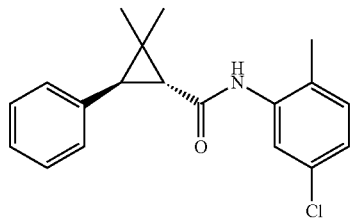

Intermediate H (400 mg, 2.10 mmol) and 5-chloro-2-methylaniline (357 mg, 2.50 mmol) were reacted as described under General Procedure D to furnish the title compound which was purified by column chromatography (cyclohexane→60% DCM/cyclohexane) to give the title compound as a white solid (486 mg, 73%). $^1$H NMR (300 MHz, CDCl$_3$) δ 8.01 (br s, 1H), 7.32-7.03 (m, 8H), 2.85 (d, 1H), 2.28 (s, 3H), 1.86-1.85 (m, 1H), 1.43 (s, 3H), 0.98 (s, 3H).

Intermediate BF: ±trans N-(5-chloro-2-methylphenyl)-2,2-dimethyl-3-(4-sulfamoylphenyl)cyclopropanecarboxamide

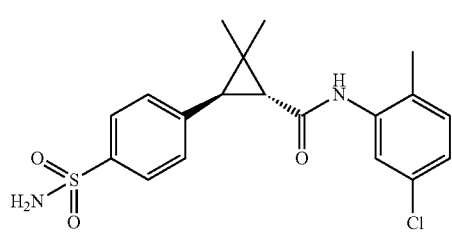

Intermediate BE (486 mg, 1.5 mmol) was reacted as described under General Procedure E to furnish the title compound which was purified by column chromatography (230 mg, 49%) as a white solid. ESIMS m/z [M+H]$^+$ 393.2.

Intermediate BG: ±trans N-(5-fluoro-2-methoxyphenyl)-2,2-dimethyl-3-phenylcyclopropanecarboxamide

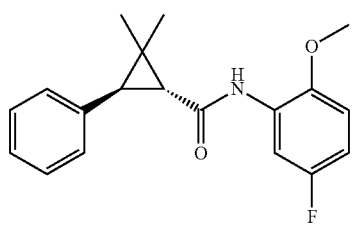 [SMILES: COc1ccc(F)cc1NC(=O)[C@@H]1[C@@H](c2ccccc2)C1(C)C]

Intermediate H (400 mg, 2.10 mmol) and 5-fluoro-2-methoxyaniline (356 mg, 2.50 mmol) were reacted as described under General Procedure D to furnish the title compound which was purified by column chromatography (cyclohexane→60% DCM/cyclohexane) to give the title compound, as a yellow solid (459 mg), which contained an amount of the 3-fluoro-6-methoxyaniline starting material. The compound was used as is in the next step without further purification. ESIMS m/z [M+H]$^+$ 314.2.

Intermediate BH: ±trans N-(5-fluoro-2-methoxyphenyl)-2,2-dimethyl-3-(4-sulfamoylphenyl)cyclopropanecarboxamide

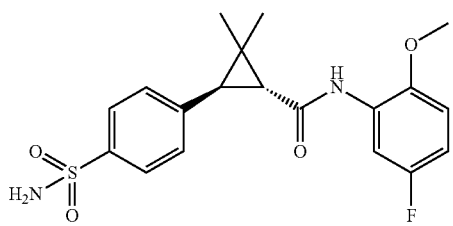 [SMILES: COc1ccc(F)cc1NC(=O)[C@@H]1[C@@H](c2ccc(S(N)(=O)=O)cc2)C1(C)C]

Intermediate BG (459 mg, 1.47 mmol) was reacted as described under General Procedure E to furnish the title compound which was purified by column chromatography (230 mg, 42%) as a white solid. ESIMS m/z [MH]$^-$ 393.2.

Intermediate BI: ±trans N-(3-chlorophenyl)-2,2-dimethyl-3-phenylcyclopropanecarboxamide

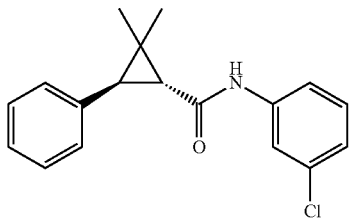 [SMILES: CC1(C)[C@H](C(=O)Nc2cccc(Cl)c2)[C@H]1c1ccccc1]

Intermediate H (375 mg, 1.97 mmol) and 3-chloroaniline (503 mg, 3.94 mmol) were reacted as described under General Procedure D to furnish the title compound which was purified by column chromatography (440 mg, 74%) as a white solid. $^1$H NMR (300 MHz, CDCl$_3$) δ 7.69 (br s, 1H), 7.46 (br s, 1H), 7.40-7.33 (m, 1H), 7.32-7.17 (m, 6H), 7.11-7.04 (m, 1H), 2.84 (d, 1H), 1.83 (d, 1H), 1.41 (s, 3H), 0.97 (s, 3H).

Intermediate BJ: ±trans N-(3-chlorophenyl)-2,2-dimethyl-3-(4-sulfamoylphenyl)cyclopropanecarboxamide

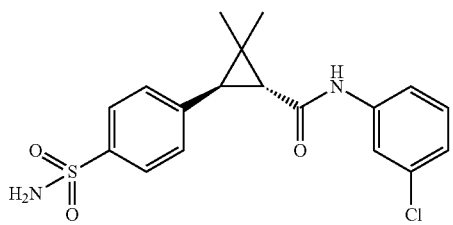 [SMILES: CC1(C)[C@H](C(=O)Nc2cccc(Cl)c2)[C@H]1c1ccc(S(N)(=O)=O)cc1]

Intermediate BI (440 mg, 1.46 mmol) was reacted as described under General Procedure E to furnish the title compound which was purified by column chromatography (350 mg, 71%) as a white solid. ESIMS m/z [M+H]+ 379.2.

Intermediate BK: ±trans 2,2-dimethyl-N-[3-(morpholin-4-yl)phenyl]-3-phenylcyclopropanecarboxamide

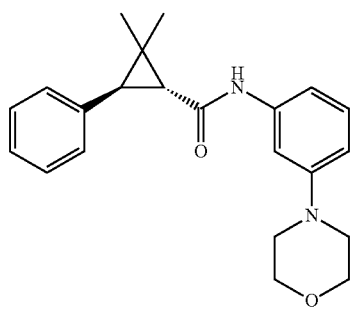 [SMILES: CC1(C)[C@H](C(=O)Nc2cccc(N3CCOCC3)c2)[C@H]1c1ccccc1]

Intermediate H (300 mg, 1.58 mmol) and 3-morpholin-4-ylaniline (338 mg, 1.89 mmol) were reacted as described under General Procedure D. The crude material was purified by column chromatography (cyclohexane→1:1 EtOAc/cyclohexane) to give the title compound (412 mg, 74%). ESIMS m/z [M−H]+ 351.3.

Intermediate BL: ±trans 2,2-dimethyl-N-[3-(morpholin-4-yl)phenyl]-3-(4-sulfamoylphenyl)cyclopropanecarboxamide

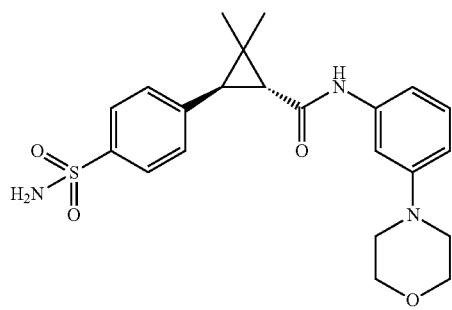 [SMILES: CC1(C)[C@H](C(=O)Nc2cccc(N3CCOCC3)c2)[C@H]1c1ccc(S(N)(=O)=O)cc1]

Intermediate BK (412 mg, 1.18 mmol) was reacted as described under General Procedure E to furnish the title compound which was purified by column chromatography (cyclohexane→20% EtOAc/cyclohexane) to give a white solid (294 mg, 58%). ESIMS m/z [M+H]+ 430.2.

Intermediate BM: ±trans N-(5-chloro-2-ethoxyphenyl)-2,2-dimethyl-3-phenylcyclopropanecarboxamide

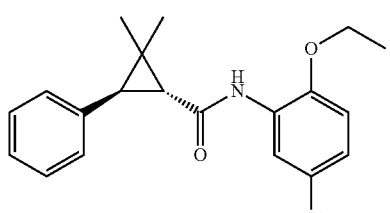

Intermediate H (300 mg, 1.58 mmol) and 5-chloro-2-ethoxyaniline (325 mg, 1.89 mmol) were reacted as described under General Procedure D. The crude material was purified by column chromatography (cyclohexane→40% EtOAc/cyclohexane) to give the title compound (357 mg, 68%) as a yellow solid. $^1$H NMR (300 MHz, CDCl$_3$) δ 8.51 (br s, 1H), 7.97 (br s, 1H), 7.33-7.19 (m, 5H), 6.97 (dd, 1H), 6.78 (d, 1H), 4.13 (q, 2H), 2.84 (d, 1H), 1.85 (d, 1H), 1.50 (t, 3H), 1.43 (s, 3H), 1.00 (s, 3H).

Intermediate BN: ±trans N-(5-chloro-2-ethoxyphenyl)-2,2-dimethyl-3-(4-sulfamoylphenyl)cyclopropanecarboxamide

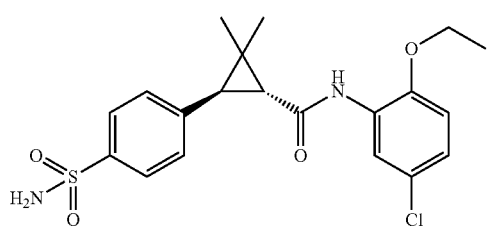 [SMILES: CCOc1ccc(Cl)cc1NC(=O)[C@@H]1[C@@H](c2ccc(S(N)(=O)=O)cc2)C1(C)C]

Intermediate BM (166 mg, 1.36 mmol) was reacted as described under General Procedure E to furnish the title compound which was purified by column chromatography (cyclohexane→50% EtOAc/cyclohexane) to give a white solid (345 mg, 60%). ESIMS m/z [M+H]+ 423.1.

Intermediate BO: ±trans N-[2-methoxy-5-(trifluoromethyl)phenyl]-2,2-dimethyl-3-phenylcyclopropanecarboxamide

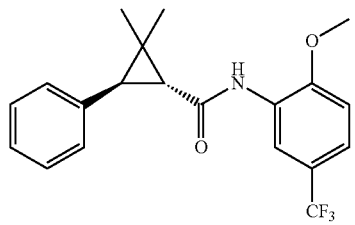 [SMILES: COc1ccc(C(F)(F)F)cc1NC(=O)[C@@H]1[C@@H](c2ccccc2)C1(C)C]

Intermediate H (400 mg, 2.1 mmol) and 2-methoxy-5-(trifluoromethyl)aniline (488 mg, 2.59 mmol) were reacted as described under General Procedure D. The crude material was purified by column chromatography (cyclohexane→60% DCM/cyclohexane) to give the title compound, as a yellow solid (713 mg), contaminated with the excess 2-methoxy-5-trifluoromethylaniline starting material. This compound was used as is in the next step. $^1$H NMR (300 MHz, CDCl$_3$) δ 8.79 (s, 1H), 8.03 (s, 1H), 7.33-7.11 (m, 6H), 6.94 (d, 1H), 3.98 (s, 3H), 2.86 (d, 1H), 1.89 (d, 1H), 1.43 (s, 3H), 1.00 (s, 3H).

Intermediate BP: ±trans N-[2-methoxy-5-(trifluoromethyl)phenyl]-2,2-dimethyl-3-(4-sulfamoylphenyl)cyclopropanecarboxamide

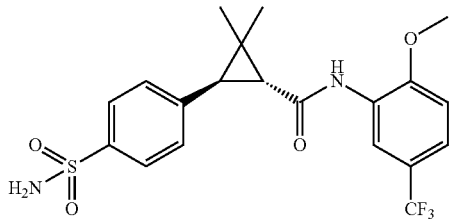 [SMILES: COc1ccc(C(F)(F)F)cc1NC(=O)[C@@H]1[C@@H](c2ccc(S(N)(=O)=O)cc2)C1(C)C]

Intermediate BO (713 mg, 1.9 mmol) was reacted as described under General Procedure E to furnish the title compound which was purified by column chromatography to give a white solid (230 mg, 35%). ESIMS m/z [M+H]$^+$ 443.2.

Intermediate BQ: (1R,3R)—N-(5-fluoro-2-methylphenyl)-2,2-dimethyl-3-phenylcyclopropanecarboxamide

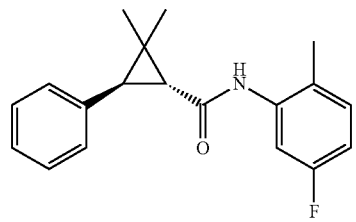 [SMILES: Cc1ccc(F)cc1NC(=O)[C@@H]1[C@@H](c2ccccc2)C1(C)C]

Intermediate AO (150 mg, 0.79 mmol) and 5-fluoro-2-methylaniline (188 mg, 0.94 mmol) were reacted as described under General Procedure D. The crude material was purified by column chromatography to yield the desired product as a white solid (160 mg, 68%). $^1$H NMR (300 MHz, CDCl$_3$) δ 7.84 (br s, 1H), 7.32-7.09 (m, 7H), 6.79-6.71 (m, 1H), 2.85 (d, 1H), 2.27 (s, 3H), 1.87 (d, 1H), 1.42 (s, 3H), 0.98 (s, 3H).

Intermediate BR: (1R,3R)—N-(5-fluoro-2-methylphenyl)-2,2-dimethyl-3-(4-sulfamoylphenyl)cyclopropanecarboxamide

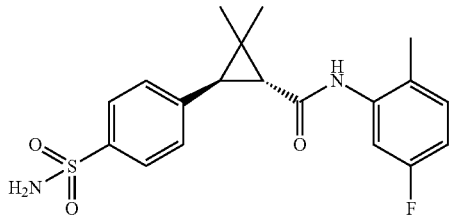 [SMILES: Cc1ccc(F)cc1NC(=O)[C@@H]1[C@@H](c2ccc(S(N)(=O)=O)cc2)C1(C)C]

Intermediate BQ (160 mg, 0.53 mmol) was reacted as described under General Procedure E to furnish the title compound which was purified by column chromatography to give a white solid (130 mg, 66%). ESIMS m/z [M+H]$^+$ 377.2.

Intermediate BS: (1R,3R)—N-(4,5-difluoro-2-methylphenyl)-2,2-dimethyl-3-phenylcyclopropanecarboxamide

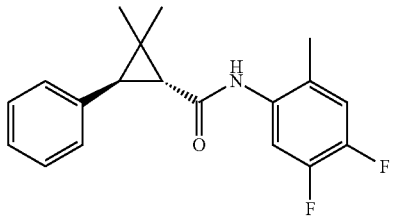 [SMILES: Cc1cc(F)c(F)cc1NC(=O)[C@@H]1[C@@H](c2ccccc2)C1(C)C]

Intermediate AO (150 mg, 0.79 mmol) and 4,5-difluoro-2-methylaniline (115 mg, 0.79 mmol) were reacted as described under General Procedure D. The crude material was purified by column chromatography to yield the desired product as a white solid (230 mg, 93%). $^1$H NMR (300 MHz, CDCl$_3$) δ 7.84-7.78 (m, 1H), 7.32-7.17 (m. 6H), 7.01-6.95 (m, 1H), 2.83 (d, 1H), 2.25 (s, 3H), 1.86 (d, 1H), 1.41 (s, 3H), 0.98 (s, 3H).17

Intermediate BT: (1R,3R)—N-(4,5-difluoro-2-methylphenyl)-2,2-dimethyl-3-(4-sulfamoylphenyl)cyclopropanecarboxamide

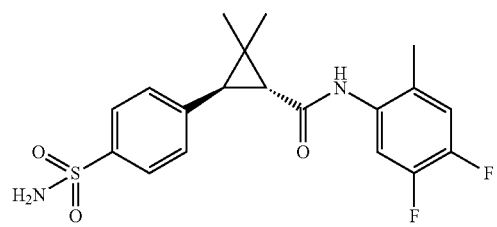 [SMILES: Cc1cc(F)c(F)cc1NC(=O)[C@@H]1[C@@H](c2ccc(S(N)(=O)=O)cc2)C1(C)C]

Intermediate BS (260 mg, 0.82 mmol) was reacted as described under General Procedure E to give the title compound (242 mg, 74%) as a white solid. Mp 209-212° C. ESIMS m/z [m+H]$^+$ 395.2.

Intermediate BU: (1S,3S)—N-(5-fluoro-2-methylphenyl)-2,2-dimethyl-3-phenylcyclopropanecarboxamide

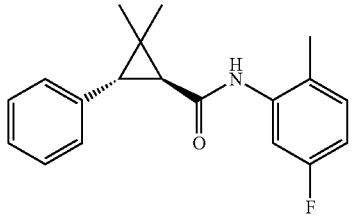 [SMILES: Cc1ccc(F)cc1NC(=O)[C@H]1[C@H](c2ccccc2)C1(C)C]

Intermediate AP (180 mg, 0.94 mmol) and 5-fluoro-2-methylaniline (188 mg, 0.94 mmol) were reacted as described under General Procedure D. The crude material was purified by column chromatography to yield the desired product as a white solid (250 mg, 90%). $^1$H NMR (300 MHz, CDCl$_3$) δ 7.87 (br s, 1H), 7.32-7.10 (m, 7H), 6.80-6.72 (m, 1H), 2.85 (d, 1H), 2.28 (s, 3H), 1.85 (d, 1H), 1.42 (s, 3H), 0.98 (s, 3H).

Intermediate BV: (1S,3S)—N-(5-fluoro-2-methyl-phenyl)-2,2-dimethyl-3-(4-sulfamoylphenyl)cyclo-propanecarboxamide

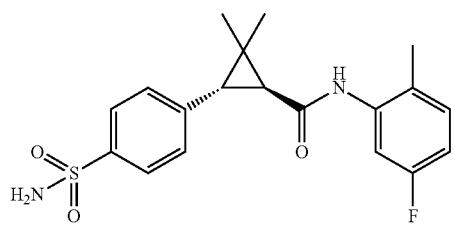 [SMILES: Cc1ccc(F)cc1NC(=O)[C@H]1[C@H](c2ccc(S(N)(=O)=O)cc2)C1(C)C]

Intermediate BU (160 mg, 0.54 mmol) was reacted as described under General Procedure E to furnish the title compound which was purified by column chromatography (cyclohexane→70% EtOAc/cyclohexane) to give a white solid (187 mg, 92%). ESIMS m/z [M+H]$^+$ 377.2.

Intermediate BW: (1S,3S)—N-(4,5-difluoro-2-meth-ylphenyl)-2,2-dimethyl-3-phenylcyclopropanecar-boxamide

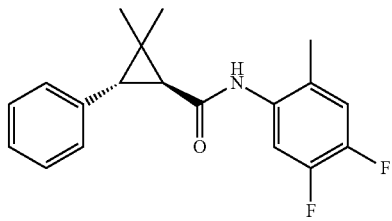 [SMILES: Cc1cc(F)c(F)cc1NC(=O)[C@H]1[C@H](c2ccccc2)C1(C)C]

Intermediate AP (180 mg, 0.94 mmol) and 4,5-difluoro-2-methylaniline (135 mg, 0.94 mmol) were reacted as described under General Procedure D. The crude material was purified by column chromatography to yield the desired product as a white solid (263 mg, 89%). $^1$H NMR (300 MHz, CDCl$_3$) δ 7.84-7.78 (m, 1H), 7.32-7.17 (m, 6H), 7.01-6.95 (m, 1H), 2.83 (d, 1H), 2.25 (s, 3H), 1.86 (d, 1H), 1.41 (s, 3H), 0.98 (s, 3H).

Intermediate BX: (1S,3S)—N-(4,5-difluoro-2-meth-ylphenyl)-2,2-dimethyl-3-(4-sulfamoylphenyl)cyclo-propanecarboxamide

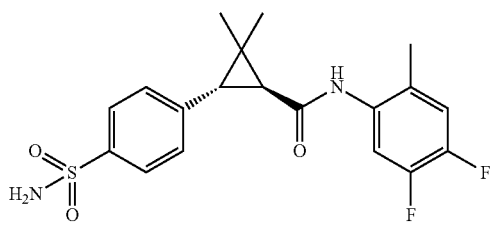 [SMILES: Cc1cc(F)c(F)cc1NC(=O)[C@H]1[C@H](c2ccc(S(N)(=O)=O)cc2)C1(C)C]

Intermediate BW (260 mg, 0.82 mmol) was reacted as described under General Procedure E to furnish the title compound which was purified by column chromatography (cyclohexane→70% EtOAc/cyclohexane) to give a white solid (242 mg, 74%). ESIMS m/z [M+H]$^+$ 395.2.

Intermediate BY: ±trans ethyl-2,2-dimethyl-3-(4-sulfamoylphenyl)cyclopropanecarboxylate

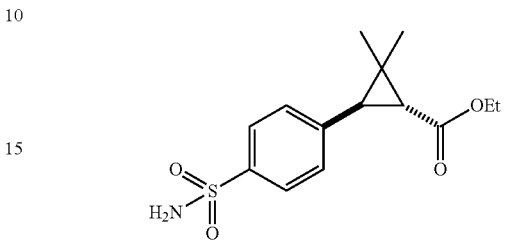

Intermediate G (1.55 g, 7.10 mmol) was reacted as described under General Procedure E to furnish the title compound which was purified by column chromatography (30% EtOAc/hexane→100% EtOAc) to give the title compound as a glassy white solid (1.12 g, 53%). ESIMS m/z [M+NH$_4$]$^+$ 315.2.

Intermediate BZ: ±trans 4-[3-(hydroxymethyl)-2,2-dimethylcyclopropyl]benzenesulfonamide

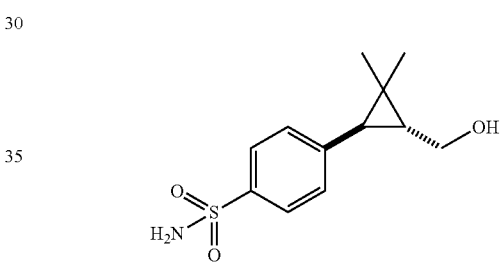

To a cooled (0° C.) solution of Intermediate BY (1.07 g, 3.60 mmol) in Et$_2$O (51 ml) was added LiAlH$_4$ (575 mg, 14.4 mmol) in one portion. The reaction mixture was stirred for 20 min at 0° C. before warming to ambient temperature. After 2.5 h LCMS showed the reaction was complete and the reaction was cooled to 0° C. and quenched by careful addition of posassium sodium tartrate (1.0 M solution). The mixture was stirred at ambient temperature for 1 h before neutralising with HCl (2 M), the product was extracted with EtOAc (4×) and the combined extracts washed with brine (2×), dried (MgSO$_4$) and concentrated in vacuo. The product was purified by column chromatography (80% EtOAc/hexane) to give the title compound as a white solid (742 mg, 81%). ESIMS m/z [M+NH$_4$]$^+$ 273.2.

Intermediate CA: ±trans 2,2-dimethyl-N-(2-methyl-pyridin-3-yl)-3-phenylcyclopropanecarboxamide

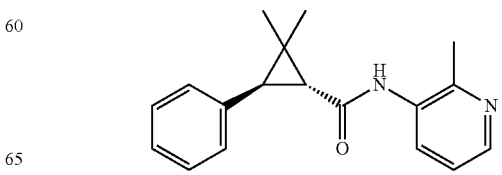

Intermediate H (350 mg, 1.8 mmol) and 3-amino-2-methylpyridine (195 mg, 1.8 mmol) were reacted as described under General Procedure D. The crude material was purified by column chromatography (cyclohexane→10% EtOAc/cyclohexane) to give the title compound (500 mg, 99%) as a white solid. ESIMS m/z [M+H]+ 381.3

Intermediate CB: ±trans 2,2-dimethyl-N-(2-methylpyridin-3-yl)-3-(4-sulfamoylphenyl)cyclopropanecarboxamide

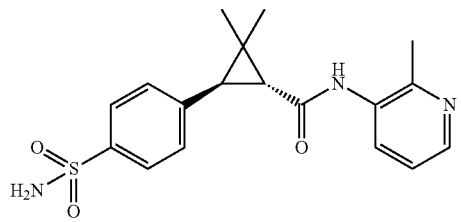 [SMILES: Cc1ncccc1NC(=O)[C@@H]1[C@@H](c2ccc(S(N)(=O)=O)cc2)C1(C)C]

Intermediate CA (500 mg, 1.78 mmol) was reacted as described under General Procedure E to furnish the title compound which was purified by column chromatography (cyclohexane→1:1 EtOAc/cyclohexane) to give the title compound as a white solid (200 mg, 25%). ESIMS m/z [M+H]+ 360.2.

Intermediate CC: ±trans N-(4-fluoro-2-methylphenyl)-2,2-dimethyl-3-phenylcyclopropanecarboxamide

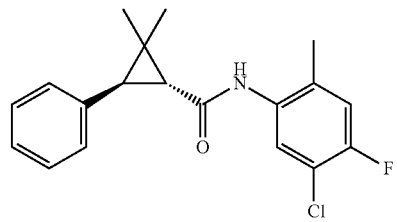 [SMILES: Cc1cc(F)c(Cl)cc1NC(=O)[C@@H]1[C@@H](c2ccccc2)C1(C)C]

Intermediate H (400 mg, 2.10 mmol) and 5-chloro-4-fluoro-2-methylaniline (408 mg, 3.00 mmol) were reacted as described under General Procedure D. The crude material was purified by column chromatography (cyclohexane→DCM) to yield the desired product as a white solid (770 mg, 77%). $^1$H NMR (300 MHz, CDCl$_3$) δ 7.92 (br d, 1H), 7.32-7.15 (m, 6H), 6.98 (br d, 1H), 2.84 (d, J=5.4 Hz, 1H), 2.27 (s, 3H), 1.86 (d, 1H), 1.42 (s, 3H), 0.98 (s, 3H).

Intermediate CD: ±trans N-(4-fluoro-2-methylphenyl)-2,2-dimethyl-3-(4-sulfamoylphenyl)cyclopropanecarboxamide

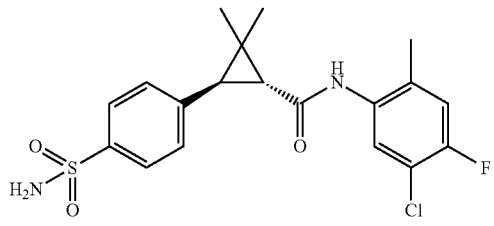 [SMILES: Cc1cc(F)c(Cl)cc1NC(=O)[C@@H]1[C@@H](c2ccc(S(N)(=O)=O)cc2)C1(C)C]

Intermediate CC (0.770 g, 2.3 mmol) was reacted as described under General Procedure E to furnish the title compound which was purified by column chromatography (cyclohexane→1:1 EtOAc/cyclohexane) to give the title compound as a white solid (750 mg, 80%). ESIMS m/z [M+H]+ 411.3.

Intermediate CE: ±trans N-(2-ethyl-5-fluorophenyl)-2,2-dimethyl-3-phenylcyclopropanecarboxamide

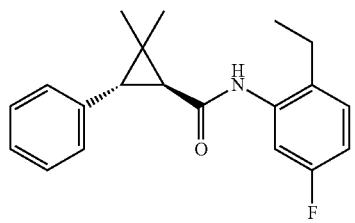 [SMILES: CCc1ccc(F)cc1NC(=O)[C@H]1[C@H](c2ccccc2)C1(C)C]

Intermediate H (300 mg, 1.5 mmol) and 2-ethyl-5-fluoroanilIne (209 mg, 1.5 mmol) were reacted as described under General Procedure D. The crude material was purified by column chromatography (cyclohexane→10% EtOAc/cyclohexane) to yield the desired product as a white solid (400 mg, 86%). ESIMS m/z [M+H]+ 312.5.

Intermediate CF: ±trans N-(2-ethyl-6-fluorophenyl)-2,2-dimethyl-3-(4-sulfamoylphenyl)cyclopropanecarboxamide

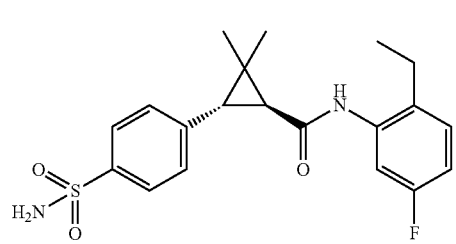 [SMILES: CCc1ccc(F)cc1NC(=O)[C@H]1[C@H](c2ccc(S(N)(=O)=O)cc2)C1(C)C]

Intermediate CE (400 mg, 1.28 mmol) was reacted as described under General Procedure E to furnish the title compound which was purified by column chromatography (cyclohexane→1:1 EtOAc/cyclohexane) to give the title compound as a white solid (500 mg, 100%). ESIMS m/z [M+H]+ 391.6.

Intermediate CG: ±trans N-[2-fluoro-5-(trifluoromethoxy)phenyl]-2,2-dimethyl-3-phenylcyclopropanecarboxamide and Intermediate CH: ±trans N-[5-fluoro-2-(trifluoromethoxy)phenyl]-2,2-dimethyl-3-phenylcyclopropanecarboxamide

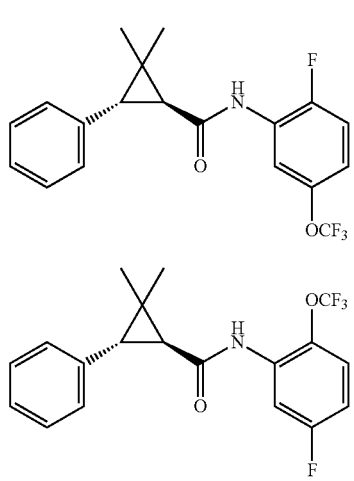

Intermediate H (400 mg, 2.10 mmol) and a mixture of 2-fluoro-5-(trifluoromethoxy)aniline and 5-fluoro-2-(trifluoromethoxy)aniline (ratio 45:55) (410 mg, 2.10 mmol) were reacted as described under General Procedure D. The crude material was purified by column chromatography (cyclohexane→6% EtOAc/cyclohexane) to yield two products, first eluting Intermediate CH (200 mg, 26%) as a white solid and second eluting Intermediate CG (160 mg, 21%) as a white solid.

Intermediate CH: $^1$H NMR (300 MHz, CDCl$_3$) δ 8.43 (br s, 1H), 7.62 (br s, 1H), 7.33-7.08 (m, 6H), 6.92-6.87 (m, 1H), 2.87 (d, 1H), 1.88 (d, 1H), 1.42 (s, 3H), 1.00 (s, 3H).

Intermediate CG: $^1$H NMR (300 MHz, CDCl$_3$) δ 8.30 (br d, 1H), 7.65 (br s, 1H), 7.34-7.15 (m, 6H), 6.82-6.75 (m, 1H), 2.86 (d, 1H), 1.86 (d, 1H), 1.40 (s, 3H), 1.00 (s, 3H).

Intermediate CI: ±trans N-[2-fluoro-5-(trifluoromethoxy)phenyl]-2,2-dimethyl-3-(4-sulfamoylphenyl)cyclopropanecarboxamide

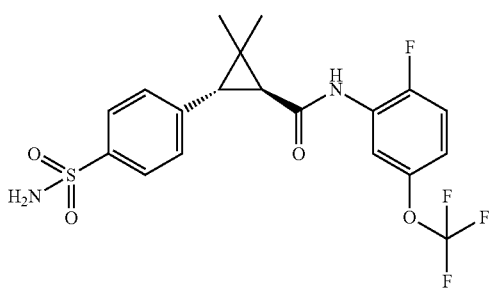 [SMILES: CC1(C)[C@@H](C(=O)Nc2cc(OC(F)(F)F)ccc2F)[C@@H]1c1ccc(S(N)(=O)=O)cc1]

Intermediate CG (200 mg, 0.45 mmol) was reacted as described under General Procedure E to furnish the title compound which was purified by column chromatography (cyclohexane→1:1 EtOAc/cyclohexane) to give the title compound as a white solid (200 mg, 83%). $^1$H NMR (300 MHz, d$_6$-DMSO) δ 10.3 (br s, 1H), 8.21-8.18 (m, 1H), 7.76 (d, 2H), 7.44-7.38 (m, 3H), 7.26 (br s, 2H), 7.14-7.11 (m, 1H), 2.66 (d, 1H), 2.61 (d, 1H), 1.32 (s, 3H), 0.88 (s, 3H).

Intermediate CJ: ±trans N-[5-fluoro-2-(trifluoromethoxy)phenyl]-2,2-dimethyl-3-(4-sulfamoylphenyl)cyclopropanecarboxamide

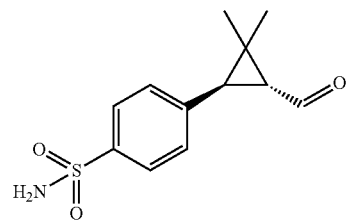 [SMILES: CC1(C)[C@H](C=O)[C@H]1c1ccc(S(N)(=O)=O)cc1]

Intermediate CH (160 mg, 0.44 mmol) was reacted as described under General Procedure E to furnish the title compound which was purified by column chromatography (cyclohexane→1:1 EtOAc/cyclohexane) to give the title compound as a white solid (130 mg, 66%). $^1$H NMR (300 MHz, d$_6$-DMSO) δ 10.1 (br s, 1H), 7.94 (dd, 1H), 7.76 (d, 2H), 7.49-7.44 (m, 1H), 7.38 (d, 2H), 7.29 (br s, 1H), 7.05 (dq, 1H), 5.74 (s, 1H), 2.68-2.61 (m, 2H), 1.30 (s, 3H), 0.88 (s, 3H).

Intermediate CK: ±trans 4-(3-formyl-2,2-dimethylcyclopropyl)benzenesulfonamide

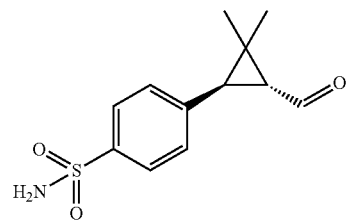 [SMILES: CC1(C)[C@H](C=O)[C@H]1c1ccc(S(N)(=O)=O)cc1]

Intermediate BZ (560 mg, 2.2 mmol) was reacted as described under General Procedure H to give the title compound which was purified by column chromatography (100% cyclohexane→60% EtOAc/cyclohexane) to furnish a colorless oil (409 mg, 73%). $^1$H NMR (300 MHz, CDCl$_3$) δ 9.63 (d, 1H), 7.87-7.84 (m, 2H), 7.33-7.30 (m, 2H), 5.00 (br s, 2H), 2.97 (d, 1H), 2.26 (dd, 1H), 1.44 (s, 3H), 0.98 (s, 3H).

Intermediate CL: ±trans 5-chloro-N-[(2,2-dimethyl-3-phenylcyclopropyl)methyl]-2-methoxyaniline

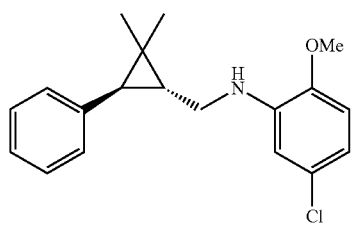 [SMILES: COc1ccc(Cl)cc1NC[C@@H]1[C@@H](c2ccccc2)C1(C)C]

Intermediate X (348 mg, 2.0 mmol) and 5-chloro-2-methoxyaniline (315 mg, 2.0 mmol) were reacted as described under General Procedure I to give the title compound which was purified by column chromatography (100% cyclohexane→70% cyclohexane/DCM) to furnish a colorless oil (417 mg, 66%). ¹H NMR (300 MHz, CDCl₃) δ 7.31-7.12 (m, 5H), 6.68-6.55 (m, 3H), 4.52 (br s, 1H), 3.83 (s, 3H), 3.31 (dd, 1H), 3.21 (dd, 1H), 1.80 (d, 1H), 1.63-1.57 (m, 1H), 1.29 (s, 3H), 0.87 (s, 3H).

Intermediate CM: ±trans ethyl-3-(4-bromophenyl)-2,2-dimethylcyclopropanecarboxylate

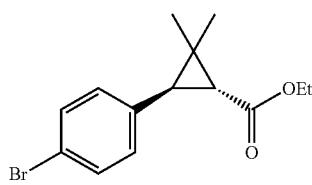 [SMILES: CCOC(=O)[C@@H]1[C@@H](c2ccc(Br)cc2)C1(C)C]

Isopropyltriphenylphosphonium iodide (17.7 g, 41 mmol) and ethyl trans-4-bromocinnamate (8.70 g, 34 mmol) were reacted as described under General Procedure B to furnish the title compound (8.05 g, 79%) as a colorless oil (cyclohexane→cyclohexane/CH₂Cl₂, 1:1). ESIMS m/z [M+H]⁺ 297.0 and 299.3.

Intermediate CN: ±trans 3-(4-bromophenyl)-2,2-dimethylcyclopropanecarboxylic acid

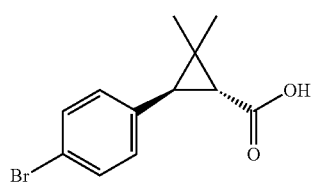

Intermediate CM (8.05 g, 27.1 mmol) was reacted as described under General Procedure C to furnish the title compound as a white solid (7.1 g, 97%). ¹H NMR (300 MHz, CDCl₃) δ 7.43-7.38 (m, 2H), 7.06-7.03 (m, 2H), 6.68 (d, 1H), 1.92 (d, 1H), 1.42 (s, 3H), 0.94 (s, 3H).

Intermediate CO: ±trans 3-(4-bromophenyl)-N-(5-chloro-2-methoxyphenyl)-2,2-dimethylcyclopropanecarboxamide

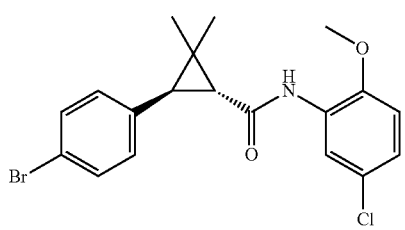 [SMILES: COc1ccc(Cl)cc1NC(=O)[C@@H]1[C@@H](c2ccc(Br)cc2)C1(C)C]

Intermediate CN (4.0 g, 14.9 mmol) and 5-chloro-2-methoxyaniline (2.6 g, 16.3 mmol) were reacted as described under General Procedure D. The crude material was purified by column chromatography (cyclohexane→60% DCM/cyclohexane) to give the title compound (2.75 g, 45%) as a white solid. ¹H NMR (300 MHz, CDCl₃) δ 8.52-8.48 (m, 1H), 7.97 (brs, 1H), 7.42-7.40 (m, 2H), 7.09-7.06 (m, 2H), 6.99 (dd, 1H), 6.79 (d, 1H), 3.91 (s, 3H), 2.77 (d, 1H), 1.83 (d, 1H), 1.39 (s, 3H), 0.97 (s, 3H).

Intermediate CP: ±trans N-(5-chloro-2-methoxyphenyl)-3-(2'-hydroxybiphenyl-4-yl)-2,2-dimethylcyclopropanecarboxamide

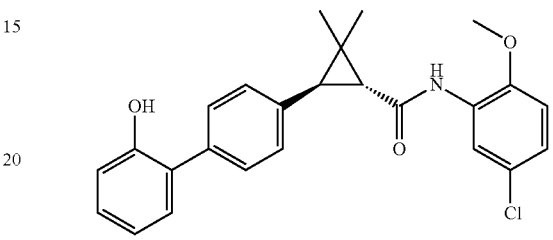

A mixture of Intermediate CO (204 mg, 0.50 mmol), 2-hydroxybenzene boronic acid (138 mg, 1.00 mmol) and cesium fluoride (228 mg, 1.50 mmol) in anhydrous DME (5 ml) and MeOH (26 ml) was degassed with argon for 30 minutes at ambient temperature. Pd(PPh₃)₄ (58 mg, 0.05 mmol) was added and the mixture was degassed with argon for 15 minutes at room temperature before heating to 130° C. in the microwave for 20 minutes. After cooling, the reaction mixture was washed with NaHCO₃ (sat. aq.) and extracted with EtOAc. The organics were dried (MgSO₄) concentrated in vacuo. The crude material was purified by column chromatography (cyclohexane→cyclohexane/EtOAc, 1:1) to give the title compound as a brown solid (138 mg, 65%). ¹H NMR (300 MHz, CDCl₃) δ 8.52 (s, 1H), 8.00 (s, 1H), 7.42-7.23 (m, 8H), 7.02-6.96 (m, 2H), 6.82-6.79 (m, 1H), 3.92 (s, 3H), 2.88 (d, 1H), 1.92 (d, 1H), 1.44 (s, 3H), 1.05 (s, 3H).

Intermediate CQ: ±trans N-[5-chloro-2-(trifluoromethyl)phenyl]-2,2-dimethyl-3-phenylcyclopropanecarboxamide

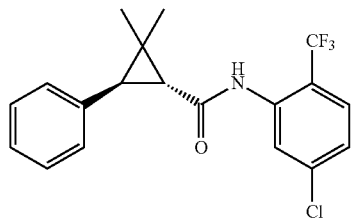 [SMILES: CC1(C)[C@H](C(=O)Nc2cc(Cl)ccc2C(F)(F)F)[C@H]1c1ccccc1]

Intermediate H (500 mg, 2.6 mmol) and 5-chloro-2-(trifluoromethyl)aniline (508 mg, 2.6 mmol) were reacted as described under General Procedure D to furnish the title compound which was used without purification in the next step.

Intermediate CR: ±trans N-[5-chloro-2-(trifluoromethyl)phenyl]-2,2-dimethyl-3-(4-sulfamoylphenyl)cyclopropanecarboxamide

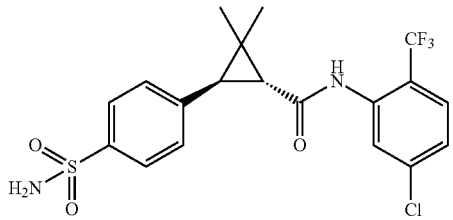 [SMILES: CC1(C)[C@H](C(=O)Nc2cc(Cl)ccc2C(F)(F)F)[C@H]1c1ccc(S(N)(=O)=O)cc1]

Intermediate CQ (400 mg, 1.09 mmol) was reacted as described under General Procedure E to furnish the title compound as a white solid (150 mg, 13% over two steps) after purification by column chromatography. $^1$H NMR (300 MHz, CDCl$_3$) δ 8.33 (br s, 1H), 7.89-7.83 (m, 2H), 7.66 (br s, 1H), 7.55 (d, 1H), 7.32 (t, 2H), 7.23-7.20 (m, 1H), 4.81-4.79 (m, 2H), 2.90 (d, 1H), 1.91 (d, 1H), 1.41 (s, 3H), 0.99 (s, 3H).

Intermediate CS: ±trans N-(6-chloro-2-methoxyphenyl)-2,2-dimethyl-3-(4-[(methylsulfonyl)amino]phenyl)cyclopropanecarboxamide

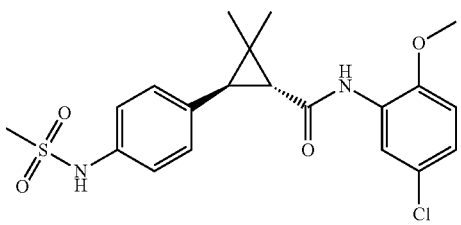

A mixture of potassium phosphate (233 mg, 1.1 mmol), Pd$_2$(dba)$_3$ (10 mg, 0.01 mmol), and t-BuXPhos (13 mg, 0.03 mmol) in anhydrous 1,4-dioxane (4 ml) was degased with argon for 5 minutes at ambient temperature and then heated at 80° C. for 30 minutes. After cooling, Intermediate CO (409 mg, 1.0 mmol) and methanesulfonamide (114 mg, 1.2 mmol) were added and the mixture was stirred under argon at 80° C. for 15 h. After cooling, the reaction medium was taken in ethyl acetate and washed with a solution of 1N HCl. The organic phase was dried over Na$_2$SO$_4$ and concentrated in vacuo. The reaction mixture was directly purified by column chromatography (100% cyclohexane→60% EtOAc/cyclohexane) leading to the expected product as a white solid (251 mg, 59%). $^1$H NMR (300 MHz, CDCl$_3$) δ 8.50 (br s, 1H), 7.98 (br s, 1H), 7.21-7.13 (m, 4H), 6.99 (dd, 1H), 6.80 (d, 1H), 6.38 (br s, 1H), 3.92 (s, 3H), 3.00 (s, 3H), 2.80 (d, 1H), 1.84 (d, 1H), 1.40 (s, 3H), 0.98 (s, 3H). ESIMS m/z [M+H]$^+$ 423.2.

Intermediate CT: ±trans ethyl-2-(4-sulfamoylphenyl)spiro[2.4]heptane-1-carboxylate

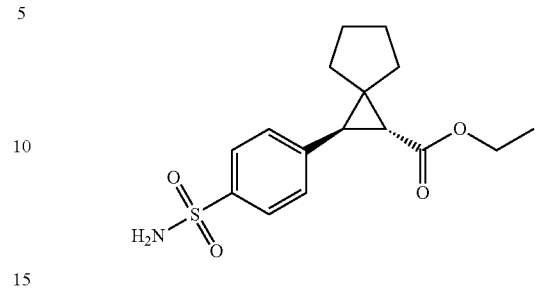

Intermediate Q (3.5 g, 14.3 mmol) was reacted as described under General Procedure E to furnish the title compound as a white solid (1.5 g, 33%) after purification by column chromatography. $^1$H NMR (300 MHz, CDCl$_3$) δ 7.84 (d, 2H), 7.24 (d, 2H), 4.88 (br s, 2H), 4.23-4.13 (m, 2H), 2.79 (d, 1H), 2.20 (d, 1H), 1.91-1.85 (m, 2H), 1.74-1.42 (m, 8H), 1.30 (t, 3H).

Intermediate CU: ±trans 4-[2-(hydroxymethyl)spiro[2.4]hept-1-yl]benzenesulfonamide

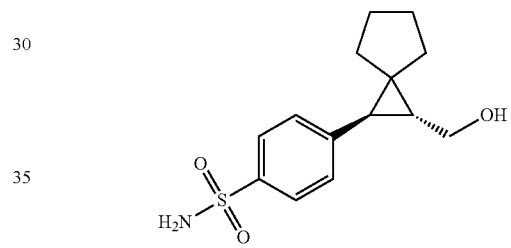

Intermediate CT (1.5 g, 4.6 mmol) was reacted as described under General Procedure G, (except 2.2 eq of LiAlH$_4$ was used) to furnish the title compound as a white solid (1.01 g, 77%) which was used crude in the next step. $^1$H NMR (300 MHz, CDCl$_3$) δ 7.81 (d, 2H), 7.20 (d, 2H), 5.29 (br s, 2H), 3.84 (dd, 1H), 3.72 (dd, 1H), 1.96-1.12 (m, 10H).

Intermediate CV: ±trans 4-[2-formylspiro[2.4]hept-1-yl]benzenesulfonamide

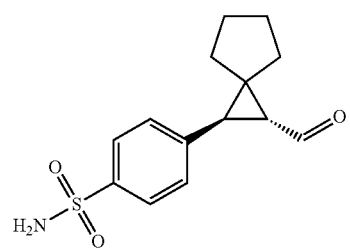 [SMILES: NS(=O)(=O)c1ccc([C@@H]2[C@@H](C=O)C23CCCC3)cc1]

Intermediate CU (900 mg, 3.2 mmol) was reacted as described under General Procedure H to give the title compound which was purified by column chromatography (100% cyclohexane→60% EtOAc/cyclohexane) to furnish a colorless oil (701 mg, 78%). $^1$H NMR (300 MHz, COCl$_3$) δ

9.50 (d, 1H), 7.85 (d, 2H), 7.25 (d, 2H), 5.03 (br s, 2H), 2.98 (d,), 2.45 (dd, 1H), 2.03-1.88 (m, 3H), 1.82-1.47 (m, 4H), 1.40-1.25 (m, 1H).

Intermediate CW: methyl (1S,3S)-2,2-dimethyl-3-phenylcyclopropanecarboxylate

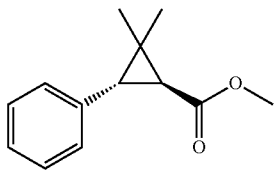

To a solution of Intermediate AP (0.602 g, 3.16 mmol) in methanol (12 ml) was added trimethyl orthoformate (3.4 eq. 1.2 ml) and sulphuric acid (cat., 6 drops). The solution was heated under reflux overnight. The reaction mixture was concentrated in vacuo and EtOAc added. The organics were washed with $H_2O$ (2×), $NaHCO_3$ (sat. aq., 2×) dried ($MgSO_4$) and concentrated in vacuo. The product was used crude in the next step without further purification (606 mg, 94%). ESIMS m/z $[M+H]^+$ 205.2.

Intermediate CX: methyl (1S,3S)-2,2-dimethyl-3-(4-sulfamoylphenyl)cyclopropanecarboxylate

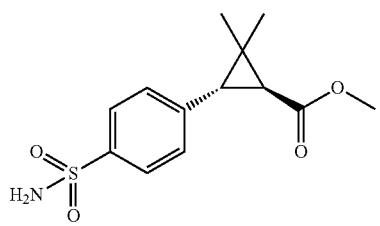 [SMILES: COC(=O)[C@H]1[C@H](c2ccc(S(N)(=O)=O)cc2)C1(C)C]

Intermediate CW (0.596 g, 2.92 mmol) was reacted as described under General Procedure E to furnish the title compound as a clear oil (269 mg, 33%) after purification by column chromatography (35% EtOAc/hexane). ESIMS m/z $[M-H]^-$ 282.3.

Intermediate CY: 4-[(1S,3S)-3-(hydroxymethyl)-2,2-dimethylcyclopropyl]benzenesulfonamide

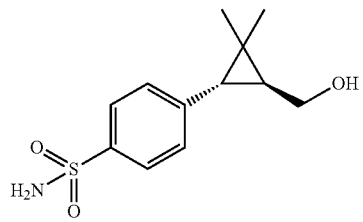 [SMILES: CC1(C)[C@@H](CO)[C@@H]1c1ccc(S(N)(=O)=O)cc1]

Intermediate CX (0.259 g, 0.91 mmol) was reacted as described for Intermediate BZ to furnish the title compound as a white solid (197 mg, 85%) after purification by trituration and column chromatography (60% EtOAc/hexane). ESIMS m/z $[M+NH_4]^+$ 273.2.

Intermediate CZ: methyl (1R,3R)-2,2-dimethyl-3-phenylcyclopropanecarboxylate

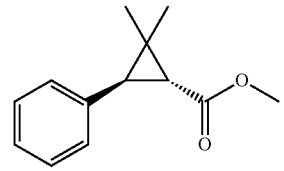

Intermediate AO (0.605 g, 3.18 mmol) was reacted as described for Intermediate CW to furnish the title compound which was used crude in the next step (619 mg, 95%). ESIMS m/z $[M+H]^+$ 205.2.

Intermediate DA: methyl (1R,3R)-2,2-dimethyl-3-(4-sulfamoylphenyl)cyclopropanecarboxylate

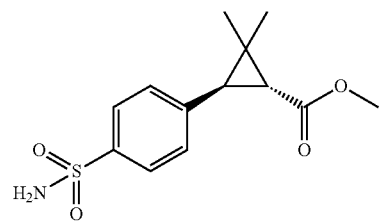 [SMILES: COC(=O)[C@@H]1[C@@H](c2ccc(S(N)(=O)=O)cc2)C1(C)C]

Intermediate CZ (0.609 g, 2.98 mmol) was reacted as described under General Procedure E to furnish the title compound as a clear oil (205 mg, 24%) after purification by column chromatography (35% EtOAc/hexane). ESIMS m/z $[M-H]^-$ 282.3.

Intermediate DB: 4-[(1R,3R)-3-(hydroxymethyl)-2,2-dimethylcyclopropyl]benzenesulfonamide

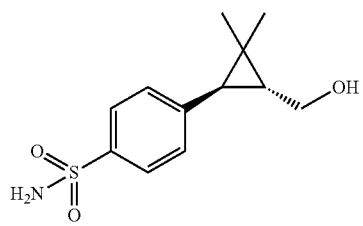 [SMILES: CC1(C)[C@H](CO)[C@H]1c1ccc(S(N)(=O)=O)cc1]

Intermediate DA (0.202 g, 0.71 mmol) was reacted as described for Intermediate BZ to furnish the title compound as a white solid (160 mg, 88%) after purification by trituration and column chromatography (60% EtOAc/hexane). ESIMS m/z $[M+NH_4]^+$ 273.2.

Intermediate DC: (1S,2S)—N-[5-fluoro-2-(trifluoromethoxy)phenyl]-2-phenylcyclopropanecarboxamide

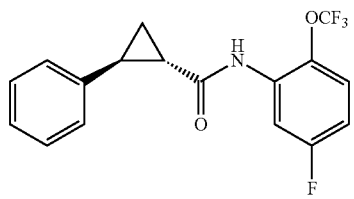 [SMILES: O=C(Nc1cc(F)ccc1OC(F)(F)F)[C@H]1C[C@@H]1c1ccccc1]

Intermediate AK (250 mg, 1.31 mmol) and 5-fluoro-2-(trifluoromethoxy) aniline (255 mg, 1.31 mmol) were reacted as described under General Procedure D to furnish the title compound as a white solid (226 mg, 51%) after purification by column chromatography (100% cyclohexane→EtOAc). $^1$H NMR (300 MHz, CDCl$_3$) δ 8.40 (br s, 1H), 7.60 (br s, 1H), 7.33-7.20 (m, 4H), 7.15-7.06 (m, 2H), 6.92-6.87 (m, 1H), 2.66-2.60 (m, 1H), 1.82-1.73 (m, 2H), 1.48-1.38 (m, 1H).

Intermediate DD: (1S,2S)—N-[5-fluoro-2-(trifluoromethoxy)phenyl]-2-(4-sulfamoylphenyl)cyclopropanecarboxamide

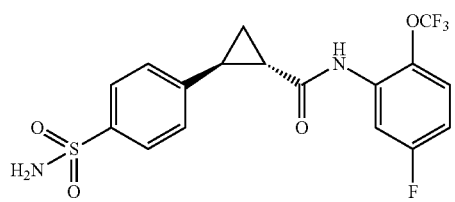 [SMILES: NS(=O)(=O)c1ccc([C@H]2C[C@@H]2C(=O)Nc2cc(F)ccc2OC(F)(F)F)cc1]

Intermediate DC (270 mg, 0.80 mmol) was reacted as described under General Procedure E to furnish the title compound as a white solid (190 mg, 57%) after purification by column chromatography (cyclohexane→50% EtOAc/cyclohexane). $^1$H NMR (300 MHz, d$_6$-DMSO) δ 10.17 (br s, 1H), 7.99 (dd, 1H), 7.72 (d, 2H), 7.47-7.41 (m, 1H), 7.35 (d, 2H), 7.88 (br s, 2H), 7.08-7.04 (m, 1H), 2.57-2.44 (m, 2H), 1.57-1.44 (m, 2H).

Intermediate DE: (1R,2R)—N-[5-fluoro-2-(trifluoromethoxy)phenyl]-2-phenylcyclopropanecarboxamide

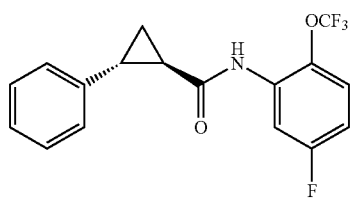 [SMILES: O=C(Nc1cc(F)ccc1OC(F)(F)F)[C@@H]1C[C@H]1c1ccccc1]

Intermediate AL (250 mg, 1.31 mmol) and 5-fluoro-2-(trifluoromethoxy) aniline (255 mg, 1.31 mmol) were reacted as described under General Procedure D to furnish the title compound as a white solid (183 mg, 35%) after purification by column chromatography (100% cyclohexane→EtOAc). $^1$H NMR (300 MHz, CDCl$_3$) δ 8.40 (br s, 1H), 7.60 (br s, 1H), 7.33-7.20 (m. 4H), 7.15-7.06 (m, 2H), 6.92-6.87 (m, 1H), 2.66-2.60 (m, 1H), 1.82-1.73 (m, 2H), 1.48-1.38 (m, 1H).

Intermediate DF: (1R,2R)—N-[5-fluoro-2-(trifluoromethoxy)phenyl]-2-(4-sulfamoylphenyl)cyclopropanecarboxamide

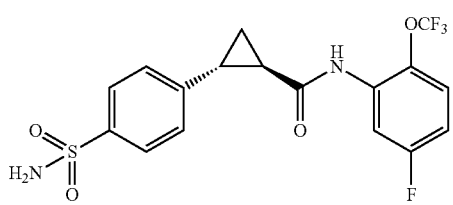 [SMILES: NS(=O)(=O)c1ccc([C@@H]2C[C@H]2C(=O)Nc2cc(F)ccc2OC(F)(F)F)cc1]

Intermediate DE (190 mg, 0.56 mmol) was reacted as described under General Procedure E to furnish the title compound as a white solid (120 mg, 51%) after purification by column chromatography (cyclohexane→50% EtOAc/cyclohexane). $^1$H NMR (300 MHz, d$_6$-DMSO) δ 10.17 (br s, 1H), 7.99 (dd, 1H), 7.72 (d, 2H), 7.47-7.41 (m, 1H), 7.35 (d, 2H), 7.88 (br s, 2H), 7.08-7.04 (m, 1H), 2.57-2.44 (m, 2H), 1.57-1.44 (m, 2H).

Intermediate DG: ±trans 2-benzylcyclopropanecarboxylic acid

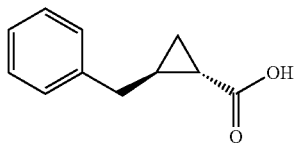

12

2-(Phenylmethyl)cyclopropane carboxylic acid, ethyl ester (1.0 g, 4.9 mmol) was reacted as described under General Procedure C to furnish the title compound (840 mg, 97%) as a yellow oil which was used without purification in the next step. $^1$H NMR (300 MHz, CDCl$_3$) δ 7.29-7.18 (m, 5H), 2.96-2.89 (m, 2H), 1.82 (ddd, 1H), 1.62 (sextet, 1H), 1.26-1.15 (m, 2H).

Intermediate DH: ±trans 2-benzyl-N-(5-chloro-2-methoxyphenyl)cyclopropanecarboxamide

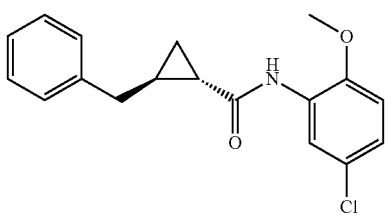 [SMILES: COc1ccc(Cl)cc1NC(=O)[C@H]1C[C@@H]1Cc1ccccc1]

Intermediate DG (0.80 g, 4.5 mmol) and 5-chloro-2-methoxyaniline (1.4 g, 9.0 mmol) were reacted as described under General Procedure D to furnish the title compound as a white solid (1.5 g, 97%) after purification by column chromatography. ESIMS m/z [M+H]+ 316.5.

Intermediate DI: ±trans N-(5-chloro-2-methoxyphenyl)-2-(4-sulfamoylbenzyl)cyclopropanecarboxamide

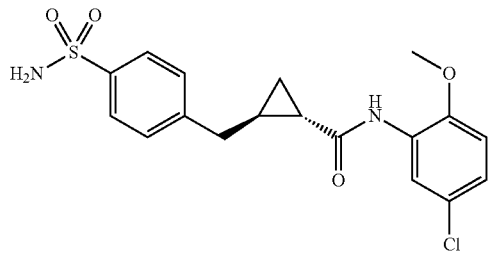 [SMILES: COc1ccc(Cl)cc1NC(=O)[C@H]1C[C@@H]1Cc1ccc(S(N)(=O)=O)cc1]

Intermediate DH (1.5 g, 4.5 mmol) was reacted as described under General Procedure E to furnish the title compound as a white solid (1.1 g, 62%) after purification by column chromatography: ESIMS m/z [M+H]+ 395.2. Mp=182-184° C.

Intermediate DJ: ±trans 4-{3-[(5-chloro-2-methoxyphenyl)carbamoyl]-2,2-dimethylcyclopropyl}benzenesulfonyl chloride

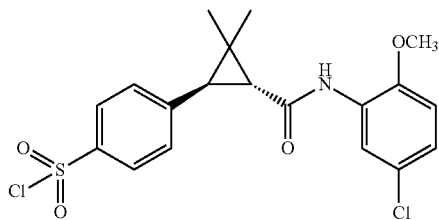 [SMILES: COc1ccc(Cl)cc1NC(=O)[C@@H]1[C@@H](c2ccc(S(=O)(=O)Cl)cc2)C1(C)C]

To a solution of chlorosulfonic acid (7.13 ml) at 0° C. was added Intermediate I (2.95 g, 8.94 mmol) portion-wise. The reaction mixture was allowed to slowly come to ambient temperature and stirred for 1 h. The reaction mixture was then poured onto ice-water with rapid stirring and the resulting precipitate collected by vacuum filtration and dried under vacuum. This material was used without further purification (3.28 g, 86%). ESIMS m/z [M+H]+ 428.0.

Intermediate DK: ±trans N-[5-chloro-2-methoxyphenyl)-3-(4-(hydroxysulfamoyl)phenyl]-2,2-dimethylcyclopropanecarboxamide

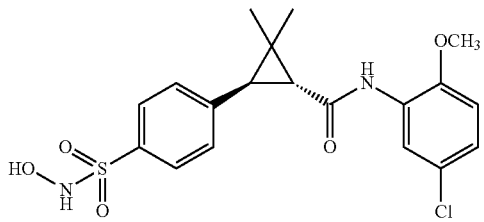 [SMILES: COc1ccc(Cl)cc1NC(=O)[C@@H]1[C@@H](c2ccc(S(=O)(=O)NO)cc2)C1(C)C]

To a solution of hydroxylamine hydrochloride (0.405 g, 5.83 mmol) and K$_2$CO$_3$ (811 mg, 5.86 mmol) in anhydrous THF was added Intermediate DJ, (250 mg, 0.58 mmol) portion-wise and the mixture stirred for 3 h. After this time the reaction was not proceeding so H$_2$O (2 ml) was added to aid in dissolution. After 1 hour the reaction was complete. The water was removed and the organics concentrated in vacuo. The crude residue was purified directly by column chromatography (50-100% EtOAc/hexane, R$_f$=0.45 in 60% EtOAc/hexane) to furnish the title compound (62 mg, 25% yield, 90% pure by LCMS at 254 nm). ESIMS m/z [M+H]+ 425.0.

Intermediate DL: ±trans N-(5-chloro-2-methoxyphenyl)-3-[4-(hydrazinylsulfonyl)phenyl]-2,2-dimethylcyclopropanecarboxamide

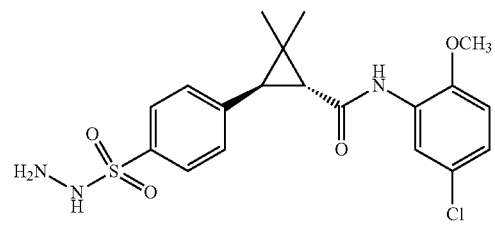 [SMILES: COc1ccc(Cl)cc1NC(=O)[C@@H]1[C@@H](c2ccc(S(=O)(=O)NN)cc2)C1(C)C]

To a solution of hydrazine hydrate (1.032 g, 20.6 mmol) in THF was added Intermediate DJ (250 mg, 0.58 mmol) portion-wise and the mixture stirred for 15 minutes. The precipitated amine hydrochloride was removed by vacuum filtration and the mixture concentrated in vacuo. The crude residue was triturated with EtOAc and then Et$_2$O to get some of the product clean while the residue was purified by column chromatography (80% EtOAc/hexane, R$_f$=0.58) which was combined with the triturated material to give the title compound (212 mg, 86%). ESIMS m/z [M+H]+ 424.0.

Intermediate DM: ±trans [3-(4-bromophenyl)-2,2-dimethylcyclopropyl]methanol

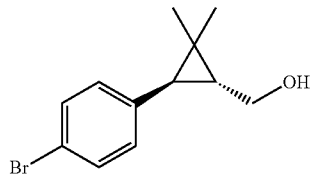

Intermediate CM (4.07 g, 13.7 mmol) was suspended in anhydrous Et$_2$O (120 ml) under an atmosphere of nitrogen and was cooled to 0° C. LiAlH$_4$ (1.09 g, 27.4 mmol) was added in one portion and the mixture stirred at 0° C. for 20 min before warming to room temperature and stirring overnight. The mixture was cooled to 0° C. and potassium sodium tartrate tetrahydrate solution (1 M, 30 ml) was added slowly. The reaction mixture was stirred at RT for 1 h before addition of HCl (2M aq.) was added to neutralise the solution. The product was extracted with Et$_2$O (4×) and the combined extracts washed with brine (2×), dried (MgSO$_4$) and concentrated in vacuo. The product was purified by column chromatography (20% EtOAc/hexane→100% EtOAc) to yield 2.92 g (84%) of the title compound. $^1$H NMR (300 MHz, CDCl$_3$) δ 7.40-7.36 (m, 2H), 7.06-7.01 (m, 2H), 3.89 (dd, 1H), 3.74-3.67 (dd, 1H), 1.70 (d, 1H), 1.43-1.36 (m, 1H), 1.28 (s, 3H), 0.84 (s, 3H).

Intermediate DN: ±trans 3-(4-bromophenyl)-2,2-dimethylcyclopropanecarbaldehyde

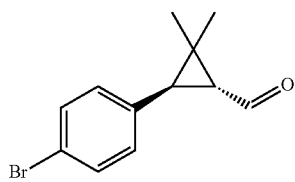

DMSO (0.31 ml, 0.340 g, 4.35 mmol) was added drop-wise to a solution of oxalyl chloride (0.19 ml, 0.274 g, 2.16 mmol) in anhydrous DCM (10 ml) at −78° C. under an atmosphere of nitrogen. The solution was stirred at −78° C. for 30 minutes before addition of a solution of Intermediate DM (0.500 g, 1.96 mmol) in anhydrous DCM (5 ml) drop-wise. The reaction mixture was stirred at −78° C. for 1.5 h before addition of NEt$_3$ (1.4 ml, 0.999 g, 9.88 mmol) drop-wise. The solution was warmed to room temperature and stirred overnight. The reaction was quenched by the addition of H$_2$O and the product extracted with DCM (3×). The combined extracts were washed with brine, dried (MgSO$_4$) and concentrated in vacuo to give the title compound (481 mg, 97%) which was used without purification in the next step.

Intermediate DO: ±trans N-([3-(4-bromophenyl)-2,2-dimethylcyclopropyl]methyl)-6-chloro-2-methoxyaniline

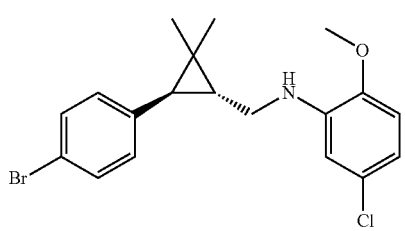 [SMILES: COc1ccc(Cl)cc1NC[C@@H]1[C@@H](c2ccc(Br)cc2)C1(C)C]

Intermediate DN (0.481 g, 1.90 mmol) was dissolved in anhydrous THF (13 ml) under an atmosphere of nitrogen. 5-Chloro-2-methoxyaniline (0.314 g, 2.00 mmol) was added followed by acetic acid (0.33 ml, 0.342 g, 5.70 mmol) and NaBH(OAc)$_3$ (0.805 g, 3.80 mmol) and the reaction mixture was stirred at ambient temperature. After 1 h the reaction was quenched by addition of NaHCO$_3$ (sat. aq.) and the mixture stirred for 15 minutes. The layers were separated and the aqueous phase extracted further with DCM (2×). The combined extracts were washed with brine, dried (MgSO$_4$) and concentrated in vacuo. The product was purified by column chromatography (100% hexane→50% DCM/hexane) to give 188 mg (25%) of the title compound. $^1$H NMR (300 MHz, CDCl$_3$) δ 7.40-7.37 (m, 2H), 7.05-7.02 (m, 2H), 6.67-6.57 (m, 3H), 4.31 (br s, 1H), 3.83 (s, 3H), 3.29 (dd, 1H), 3.19 (dd, 1H), 1.73 (d, 1H), 1.42-1.35 (m, 1H), 1.30 (s, 3H), 0.85 (s, 3H).

Intermediate DP: trans N-(2,2-difluorocyclohexyl)-2,2-dimethyl-3-phenylcyclopropanecarboxamide

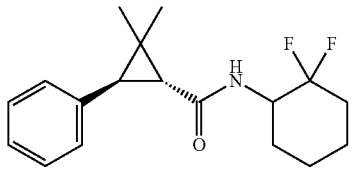 [SMILES: CC1(C)[C@H](C(=O)NC2CCCCC2(F)F)[C@H]1c1ccccc1]

Intermediate H (0.204 g, 1.07 mmol) and 2,2-difluorocyclohexaneamine hydrochloride (0.193 g, 1.13 mmol) were reacted as described under General Procedure J to furnish the title compound (0.352 g), as a diastereomeric pair, which was used crude in subsequent reactions. ESIMS m/z [M+H]$^+$ 308.3.

Intermediate DQ: trans N-(2,2-difluorocyclohexyl)-2,2-dimethyl-3-(4-sulfamoylphenyl)cyclopropanecarboxamide

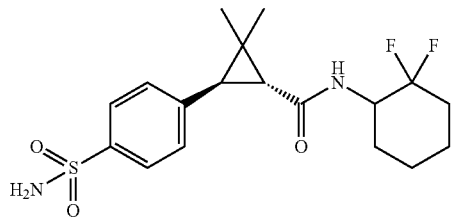 [SMILES: CC1(C)[C@H](C(=O)NC2CCCCC2(F)F)[C@H]1c1ccc(S(N)(=O)=O)cc1]

Intermediate DP (0.352 g) was reacted as described under General Procedure E to furnish the title compound (0.415 g), as a diastereomeric pair, which was used crude in subsequent reactions. ESIMS m/z [M+H]$^+$ 387.0.

Example 1: ±trans 4-(2-{[(5-chloro-2-methoxyphenyl)amino]methyl}cyclopropyl)benzenesulfonamide

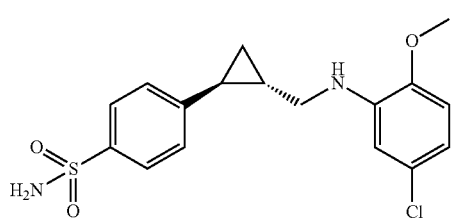 [SMILES: COc1ccc(Cl)cc1NC[C@H]1C[C@@H]1c1ccc(S(N)(=O)=O)cc1]

Intermediate B (180 mg, 0.47 mmol) was reacted as described under General Procedure F to furnish the title compound (88 mg, 51%) as a white solid. $^1$H NMR (300 MHz, CDCl$_3$+1 drop DMSO-d$_6$) δ 7.77-7.72 (m, 2H), 7.11-7.07 (m, 2H), 6.60-6.51 (m, 2H), 6.47 (d, 1H), 5.88 (s, 2H), 4.43-4.26 (m, 1H), 3.76 (s, 3H), 3.10 (t, 2H), 1.86-1.82 (m, 1H), 1.47-1.41 (m, 1H), 1.04-0.99 (m, 2H). ESIMS m/z [M+H]$^+$ 367.0.

Example 2: ±trans 4-(2-{[(3,4-difluorophenyl)amino]methyl}cyclopropyl)benzenesulfonamide

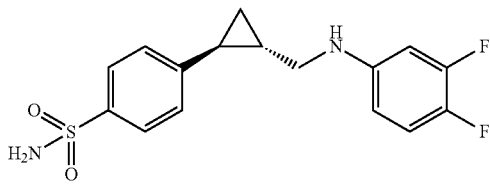 [SMILES: NS(=O)(=O)c1ccc([C@H]2C[C@@H]2CNc2ccc(F)c(F)c2)cc1]

Intermediate F (293 mg, 0.83 mmol) was reacted as described under General Procedure F to furnish the title compound (138 mg, 49%) as a white solid. $^1$H NMR (300 MHz, CDCl$_3$) δ 7.84-7.80 (m, 2H), 7.19-7.15 (m, 2H), 7.01-6.91 (m, 1H), 6.43-6.36 (m, 1H), 8.30-6.24 (m, 1H), 4.74 (s, 2H), 3.78 (brs, 1H), 3.12 (d, 2H), 1.91 (ddd, 1H), 1.55-1.44 (m, 1H), 1.11-1.06 (m, 2H). ESIMS m/z [M+H]$^+$ 339.0.

Example 3: ±trans 4-(2-{[(4-fluorophenyl)amino]methyl}cyclopropyl)benzenesulfonamide

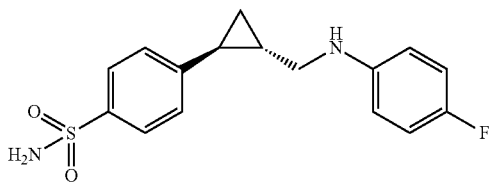 [SMILES: NS(=O)(=O)c1ccc([C@H]2C[C@@H]2CNc2ccc(F)cc2)cc1]

Intermediate D (271 mg, 0.81 mmol) was reacted as described under General Procedure F to furnish the title compound, recrystalisation from ethylacetate/dichloromethane gave (56 mg, 22%) as a white solid. $^1$H NMR (300 MHz, CDCl$_3$+1 drop DMSO-d$_6$) δ 7.67-7.72 (m, 2H), 7.11-7.06 (m, 2H), 6.87-6.79 (m, 2H), 6.55-6.46 (m, 2H), 5.84 (s, 2H), 3.77 (brs, 1H), 3.14-3.02 (m, 2H), 1.84 (ddd, 1H), 1.49-1.39 (m, 1H), 1.04-0.97 (m, 2H). ESIMS m/z [M+H]$^+$ 321.2.

Example 4: ±trans 4-(3-{[(5-chloro-2-methoxyphenyl)amino]methyl}-2,2-dimethylcyclopropyl)benzenesulfonamide

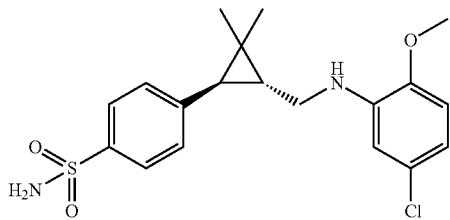 [SMILES: COc1ccc(Cl)cc1NC[C@@H]1[C@@H](c2ccc(S(N)(=O)=O)cc2)C1(C)C]

Intermediate J (200 mg, 0.49 mmol) was reacted as described under General Procedure F to give the title compound (90 mg, 47%) as a white solid.
Alternatively Intermediate CL (415 mg, 1.3 mmol) was reacted as described under General Procedure E to give the title compound (141 mg, 27%) as a white solid. $^1$H NMR (300 MHz, d$_6$-DMSO) δ 7.68 (d, 2H), 7.31 (d, 2H), 7.26 (s, 2H), 6.76 (d, 1H), 6.57 (d, 1H), 6.51 (dd,), 5.07-5.03 (m, 1H), 3.75 (s, 3H), 3.26-3.14 (m, 2H), 1.86 (d, 1H), 1.62-1.50 (m, 1H), 1.25 (s, 3H), 0.77 (s, 3H). mp 186-188° C. ESIMS m/z [M+H]$^+$ 395.0.

Example 5: ±trans 4-{2,2-dimethyl-3-[(phenylamino)methyl]cyclopropyl}benzenesulfonamide

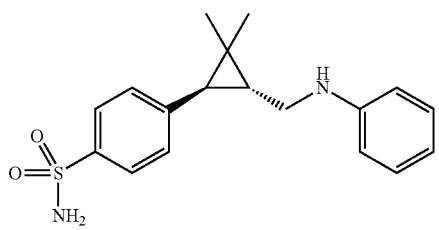 [SMILES: CC1(C)[C@H](CNc2ccccc2)[C@H]1c1ccc(S(N)(=O)=O)cc1]

Intermediate L (170 mg, 0.5 mmol) was reacted as described under General Procedure F to give the title compound (90 mg, 55%) as a white solid. $^1$H NMR (300 MHz, CD$_3$OD) δ 7.77 (dd, 2H), 7.30 (d, 2H), 7.14-7.08 (m, 2H), 6.73-6.60 (m, 3H), 3.29-3.25 (m, 2H), 1.88 (d, 1H), 1.56-1.53 (m, 1H), 1.32 (s, 3H), 0.83 (s, 3H). ESIMS m/z [M+H]$^+$ 331.1.

Example 6: ±trans 4-(2,2-dimethyl-{[methyl(phenyl)amino]methyl}cyclopropyl)benzenesulfonamide

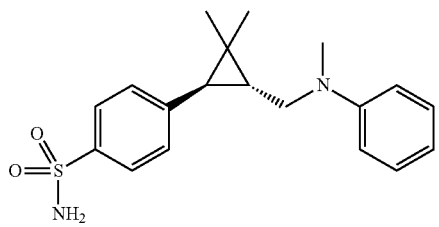 [SMILES: CN(C[C@@H]1[C@@H](c2ccc(S(N)(=O)=O)cc2)C1(C)C)c1ccccc1]

Intermediate N (250 mg, 0.7 mmol) was reacted as described under General Procedure F to give the title compound (90 mg, 37%) as a colourless oil. $^1$H NMR (300 MHz, CD$_3$OD) δ 7.75-7.72 (m, 2H), 7.23-7.16 (m, 4H), 6.88-6.85 (m, 2H), 6.71-6.66 (m, 1H), 3.63 (dd, 1H), 3.44 (dd, 1H), 2.94 (s, 3H), 1.87 (d, 1H), 1.41-1.34 (m, 1H), 1.30 (s, 3H), 0.79 (s, 3H). ESIMS m/z [M+H]$^+$ 345.2.

Example 7: ±trans 4-(3-{[(5-chloro-2-methoxyphenyl)(methyl)amino]methyl}-2,2-dimethylcyclopropyl)benzenesulfonamide

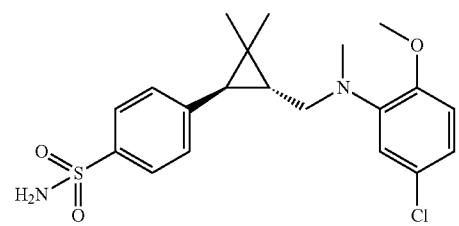 [SMILES: COc1ccc(Cl)cc1N(C)C[C@@H]1[C@@H](c2ccc(S(N)(=O)=O)cc2)C1(C)C]

Intermediate P (160 mg, 0.37 mmol) was reacted as described under General Procedure F to give the title compound (133 mg, 88%) as a white solid. $^1$H NMR (300 MHz, d$_6$-DMSO) δ 7.67 (d, 2H), 7.26-7.23 (m, 4H), 6.88-6.83 (m, 3H), 3.76 (s, 3H), 3.30-3.16 (m, 2H), 2.75 (s, 3H), 1.70 (d, 1H), 1.38-1.33 (m, 1H), 1.07 (s, 3H), 0.70 (s, 3H). ESIMS m/z [M+H]$^+$ 409.1.

Example 8: ±trans 4-(2-{[(5-chloro-2-methoxyphenyl)amino]methyl}spiro[2.4]hept-1-yl)benzenesulfonamide

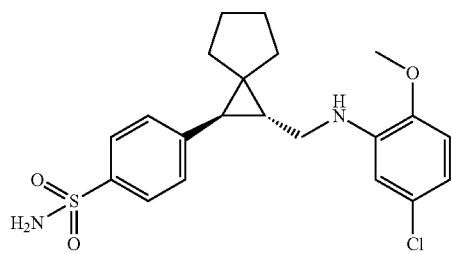 [SMILES: COc1ccc(Cl)cc1NC[C@@H]1[C@@H](c2ccc(S(N)(=O)=O)cc2)C12CCCC2]

Intermediate T (50 mg, 0.1 mmol) was reacted as described under General Procedure F to give the title compound (9 mg, 36%) as a white solid. $^1$H NMR (300 MHz, CD$_3$OD) δ 7.78 (d, 2H), 7.26 (d, 2H), 6.73 (d, 1H), 6.60-6.53 (m, 2H), 3.80 (s, 3H), 3.24 (m, 2H), 2.00 (d, J=5.6 Hz, 1H), 1.93-1.86 (m, 1H), 1.80-1.39 (m, 7H), 1.29-1.18 (m, 1H). ESIMS m/z [M+H]$^+$ 421.1.

Example 9: ±trans 4-(2-{[(2,6-dimethoxypyridin-3-yl)amino]methyl}spiro[2.4]hept-1-yl)benzenesulfonamide

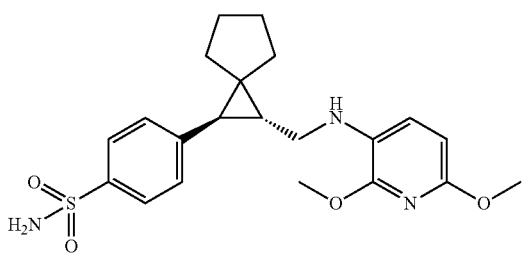 [SMILES: COc1ccc(NC[C@@H]2[C@@H](c3ccc(S(N)(=O)=O)cc3)C23CCCC3)c(OC)n1]

Intermediate V (20 mg, 0.05 mmol) was reacted as described under General Procedure F to give the title compound (15.5 mg, 79%) as a white solid. $^1$H NMR (300 MHz, DMSO-d$_6$) δ 7.70-7.66 (m, 2H), 7.26-7.19 (m, 4H), 6.96-6.93 (m, 1H), 6.12-6.09 (m, 1H), 4.33-4.27 (m, 1H), 3.85 (s, 3H), 3.72 (s, 3H), 3.15-3.11 (m, 1H), 1.95 (d, 1H), 1.82-1.38 (m, 8H), 1.12-1.06 (m, 1H). ESIMS m/z [M+H]$^+$ 418.2. Mp=56-58° C.

Example 10: ±trans 4-[3-{[(5-fluoropyridin-3-yl)amino]methyl}-2,2-dimethylcyclopropyl]benzenesulfonamide

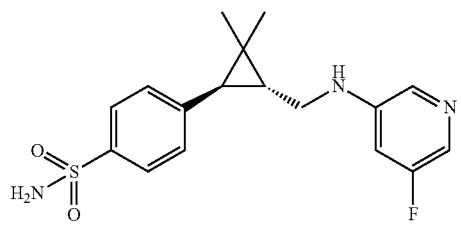 [SMILES: CC1(C)[C@H](CNc2cncc(F)c2)[C@H]1c1ccc(S(N)(=O)=O)cc1]

Intermediate Z (385 mg) was reacted as described under General Procedure F to give the title compound (4.5 mg, 1.2% yield) pure after two pTLC purifications (50% EtOAc/CHCl$_3$). $^1$H NMR (300 MHz, CDCl$_3$) δ 7.95-7.78 (m, 4H), 7.28 (d, 2H), 6.63 (d, 1H), 4.90 (br s, 2H), 3.98 (br s, 1H), 3.35-3.23 (m, 2H), 1.86 (d, 1H), 1.50 (apt q, 1H), 1.33 (s, 3H), 0.87 (s, 3H). ESIMS m/z [M+H]$^+$ 350.3

Example 11: ±trans 4-[2,2-dimethyl-3-({[2-(trifluoromethyl)pyridin-4-yl]amino}methyl)cyclopropyl]benzenesulfonamide

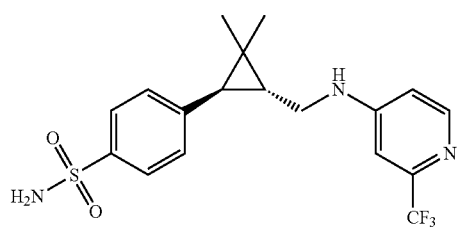 [SMILES: CC1(C)[C@H](CNc2ccnc(C(F)(F)F)c2)[C@H]1c1ccc(S(N)(=O)=O)cc1]

Intermediate AB (423 mg) was reacted as described under General Procedure F to give the title compound (10.8 mg, 2.7%) pure after two pTLC purifications (60% EtOAc/hexane then 50% EtOAc/hexane). $^1$H NMR (300 MHz, CDCl$_3$+2 drops of d$_6$-DMSO) δ 8.19 (d, 1H), 7.78-7.75 (m, 2H), 7.25-7.18 (m, 2H), 6.82 (d, 1H), 6.53 (dd, 1H), 5.97 (s, 2H), 5.33 (br t, 1H), 3.29-3.24 (m, 2H), 1.79 (d, 1H), 1.44-1.37 (m, 1H), 1.25 (s, 3H), 0.80 (m, 3H). ESIMS m/z [M+H]$^+$ 400.0.

Example 12: ±trans 4-[2-({[5-(trifluoromethyl)pyridin-2-yl]amino}methyl)cyclopropyl]benzenesulfonamide

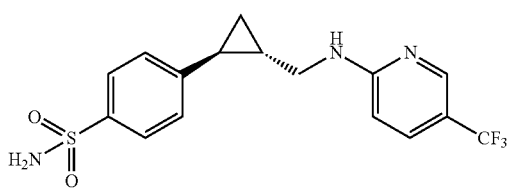 [SMILES: NS(=O)(=O)c1ccc([C@H]2C[C@@H]2CNc2ccc(C(F)(F)F)cn2)cc1]

Intermediate AD (51 mg) was reacted as described under General Procedure F to give the title compound (9 mg, 17%) purified by pTLC (80% EtOAc/CHCl$_3$). $^1$H NMR (300

MHz, d₆-DMSO) δ 8.28 (br s, 1H), 7.72-7.48 (m, 4H), 7.34-7.18 (m, 4H), 6.59 (d, 1H), 3.50-3.20 (m, 2H), 2.10-1.86 (m, 1H), 1.55-1.40 (m, 1H), 1.32-1.25 (m, 1H), 1.10-0.88 (m, 1H). ESIMS m/z [M+H]⁺ 372.0.

Example 13: ±trans 4-[3-{[(4-fluorophenyl)amino]methyl}-2,2-dimethylcyclopropyl]benzenesulfonamide

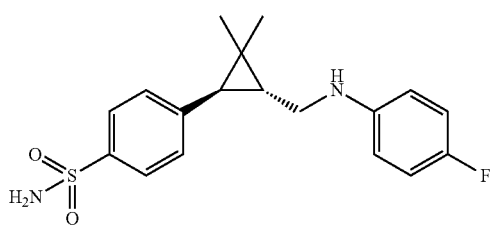 [SMILES: CC1(C)[C@H](CNc2ccc(F)cc2)[C@H]1c1ccc(S(N)(=O)=O)cc1]

Intermediate AF was reacted as described under General Procedure F to give the title compound as a white solid (71 mg, 19% over 3 steps) after column chromatography (33% EtOAc/hexane) and pTLC (20% EtOAc/CHCl₃). ¹H NMR (300 MHz, CDCl₃) δ 7.83-7.81 (m, 2H), 7.29-7.26 (m, 3H), 6.93-6.88 (m, 2H), 6.61-6.57 (m, 2H), 4.86 (br s, 2H), 3.32-3.19 (m, 2H), 1.83 (d, 1H), 1.49 (q, 1H), 1.31 (s, 3H), 0.86 (s, 3H). ESIMS m/z [M+H]⁺ 349.2.

Example 14: ±trans 4-[3-{[(3,4-difluorophenyl)amino]methyl}-2,2-dimethylcyclopropyl]benzenesulfonamide

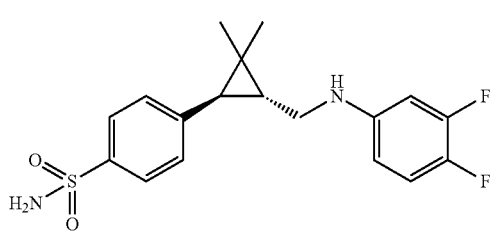 [SMILES: CC1(C)[C@H](CNc2ccc(F)c(F)c2)[C@H]1c1ccc(S(N)(=O)=O)cc1]

Intermediate AH was reacted as described under General Procedure F to give the title compound as a white solid (163 mg, 42% over 3 steps) after column chromatography (5% EtOAc/DCM then 10% EtOAc/DCM) followed by recrystallization from CHCl₃/pentane. ¹H NMR (300 MHz, CDCl₃) δ 7.85-7.81 (m, 2H), 7.29-7.26 (m, 2H), 6.96 (dt, 1H), 6.46-6.39 (m, 1H), 6.33-6.27 (m, 1H), 4.84 (br s, 2H), 3.67 (br s, 1H), 3.30-3.16 (m, 2H), 1.83 (d,), 1.48 (q, 1H), 1.31 (s, 3H), 0.86 (s, 3H). ESIMS m/z [M+H]⁺ 367.3.

Example 15: 4-[(1R,3R)-3-({[4-fluoro-2-(trifluoromethyl)phenyl]amino}methyl)-2,2-dimethylcyclopropyl]benzenesulfonamide

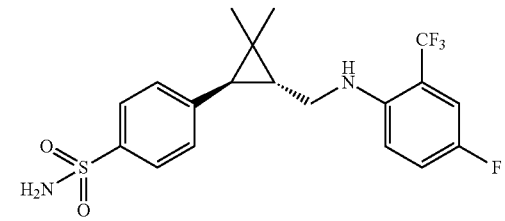

Intermediate AR (382 mg) was reacted as described under General Procedure F to give the title compound (113 mg, 23%, over 2 steps) as a white crystalline solid after purification by pTLC (40% EtOAc/hexane). ¹H NMR (300 MHz, CDCl₃) δ 7.86-7.82 (m, 2H), 7.30-7.27 (m, 2H), 7.19 (dd, 1H), 7.12 (dt, 1H), 6.71 (dd, 1H), 4.89-4.87 (m, 2H), 4.25 (brs, 1H), 3.42 (dd, 1H), 3.21 (dd, 1H), 1.87 (d, 1H), 1.52 (ddd, 1H), 1.32 (s, 3H), 0.87 (s, 3H). ESIMS m/z [M+H]⁺ 417.0.

Example 16: 4-[(1R,3R)-3-({[5-fluoro-2-(2,2,2-trifluoroethoxy)phenyl]amino}methyl)-2,2-dimethylcyclopropyl]benzenesulfonamide

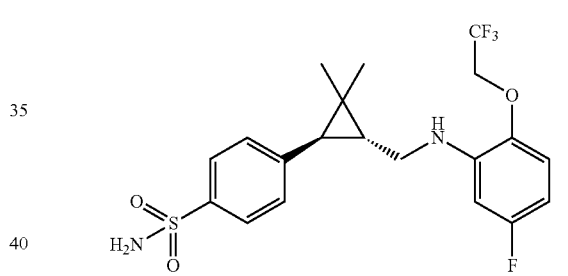

Intermediate AT (435 mg) was reacted as described under General Procedure F to give the title compound (156 mg, 31%, over 2 steps) as a pale pink gum after purification by pTLC (40% EtOAc/hexane). ¹H NMR (300 MHz, CDCl₃) δ 7.85-7.81 (m, 2H), 7.30-7.26 (m, 2H), 6.71 (dd, 1H), 6.38 (dd, 1H), 6.31 (dt, 1H), 4.95 (brs, 2H), 4.40-4.10 (m, 3H), 3.35 (dd, 1H), 3.19 (dd, 1H), 1.86 (d, 1H), 1.51 (dt, 1H), 1.32 (s, 3H), 0.87 (s, 3H). ESIMS m/z [M+H]⁺ 447.3.

Example 17: 4-[(1S,3S)-3-({[4-fluoro-2-(trifluoromethyl)phenyl]amino}methyl)-2,2-dimethylcyclopropyl]benzenesulfonamide

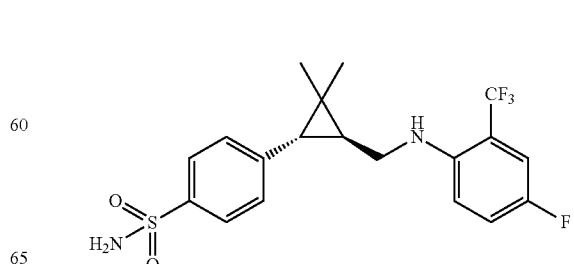

Intermediate AV (299 mg) was reacted as described under General Procedure F to give the title compound (143 mg, 49%) as a white crystalline solid after purification by pTLC (40% EtOAc/hexane). $^1$H NMR (300 MHz, CDCl$_3$) δ 7.86-7.82 (m, 2H), 7.30-7.27 (m, 2H), 7.19 (dd, 1H), 7.12 (dt, 1H), 6.71 (dd, J=1H), 4.76 (brs, 2H), 4.25 (brs, 1H), 3.42 (dd, 1H), 3.21 (dd, 1H), 1.87 (d, 1H), 1.56-1.49 (m, 1H), 1.32 (s, 3H), 0.87 (s, 3H). ESIMS m/z [M+H]$^+$ 417.0.

Example 18: 4-[(1R,2R)-2-{[(4-fluorophenyl)amino]methyl}cyclopropyl]benzenesulfonamide

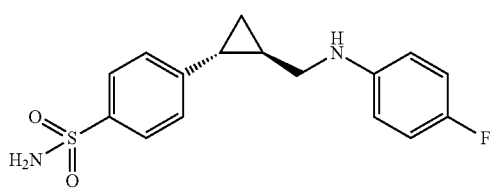 [SMILES: NS(=O)(=O)c1ccc([C@@H]2C[C@H]2CNc2ccc(F)cc2)cc1]

Intermediate AX was reacted as described under General Procedure F to give the title compound (80 mg, 21%) as a crystalline powder after purification by column chromatography (40%→60% EtOAc/hexane). $^1$H NMR (300 MHz, CDCl$_3$+1 drop DMSO-d$_6$) δ 7.67-7.72 (m, 2H), 7.11-7.06 (m, 2H), 6.87-6.79 (m, 2H), 6.55-6.46 (m, 2H), 5.84 (s, 2H), 3.77 (brs, 1H), 3.14-3.02 (m, 2H), 1.84 (ddd, 1H), 1.49-1.39 (m, 1H), 1.04-0.97 (m, 2H). ESIMS m/z [M+H]$^+$ 321.2.

Example 19: 4-[(1R,2R)-2-({[5-(trifluoromethyl)pyridin-2-yl]amino}methyl)cyclopropyl]benzenesulfonamide

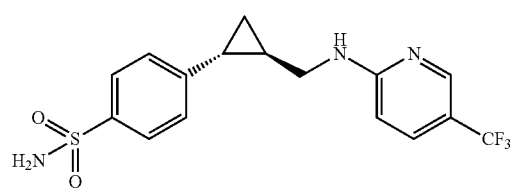 [SMILES: NS(=O)(=O)c1ccc([C@@H]2C[C@H]2CNc2ccc(C(F)(F)F)cn2)cc1]

Intermediate AZ was reacted as described under General Procedure F to give the title compound (6 mg, 3.5%, with a 10% impurity) after two columns (50% EtOAc/DCM and 60% EtOAc/hexane) and one pTLC (40% EtOAc/CHCl$_3$). R$_f$=0.40 in 60% EtOAc/hexane. $^1$H NMR (300 MHz, d$_3$-MeOD) δ 8.21 (br s, 1H), 7.77-7.73 (m, 2H), 7.59-7.55 (m, 1H), 7.26-7.20 (m, 2H), 6.60 (d, 1H), 3.43 (d, 2H), 2.03-1.96 (m, 1H), 1.60-1.49 (m, 1H), 1.22-1.03 (m, 2H). ESIMS m/z [M+H]$^+$ 372.0.

Example 20: 4-[(1R,3R)-3-{[(5-chloro-2-methoxyphenyl)amino]methyl}-2,2-dimethylcyclopropyl]benzenesulfonamide

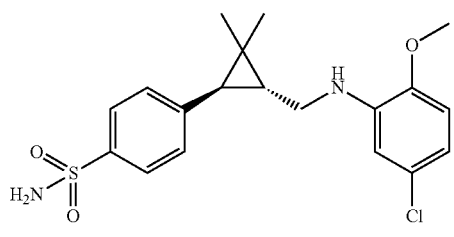 [SMILES: COc1ccc(Cl)cc1NC[C@@H]1[C@@H](c2ccc(S(N)(=O)=O)cc2)C1(C)C]

Intermediate BB (526 mg) was reacted as described under General Procedure F to give the title compound (239 mg, 47%) as a white crystalline solid after purification by column chromatography (30% EtOAc/hexane). $^1$H NMR (300 MHz, d$_6$-DMSO) δ 7.73-7.65 (m, 2H), 7.31 (d, 2H), 7.23 (s, 2H), 6.76 (d, 1H), 6.58-6.50 (m, 2H), 5.04-5.00 (m, 1H), 3.75 (s, 3H), 3.22 (dt, 2H), 1.86 (d, 1H), 1.56 (q, 1H), 1.26 (s, 3H), 0.78 (s, 3H). ESIMS m/z [M+H]$^+$ 395.1.

Example 21: 4-[(1S,3S)-3-{[(5-chloro-2-methoxyphenyl)amino]methyl}-2,2-dimethylcyclopropyl]benzenesulfonamide

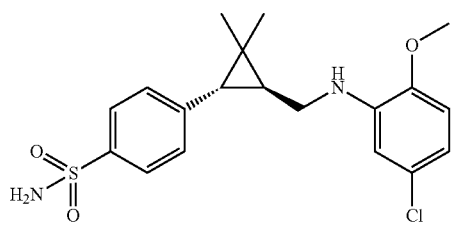 [SMILES: COc1ccc(Cl)cc1NC[C@H]1[C@H](c2ccc(S(N)(=O)=O)cc2)C1(C)C]

Intermediate BD (342 mg) was reacted as described under General Procedure F to give the title compound (149 mg, 45%) as a white crystalline solid after purification by column chromatography (33% EtOAc/hexane). $^1$H NMR (300 MHz, d$_6$-DMSO) δ 7.73-7.65 (m, 2H), 7.31 (d, 2H), 7.22 (s, 2H), 6.76 (d, 1H), 6.58-6.50 (m, 2H); 5.04-5.00 (m, 1H), 3.75 (s, 3H), 3.22 (dt, 2H), 1.86 (d, 1H), 1.56 (q, 1H), 1.26 (s, 3H), 0.78 (s, 3H). ESIMS m/z [M+H]$^+$ 395.1.

Example 22: ±trans 4-[3-{[(5-chloro-2-methylphenyl)amino]methyl}-2,2-dimethylcyclopropyl]benzenesulfonamide

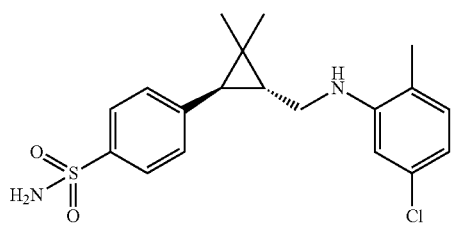 [SMILES: Cc1ccc(Cl)cc1NC[C@@H]1[C@@H](c2ccc(S(N)(=O)=O)cc2)C1(C)C]

Intermediate BF (150 mg, 0.48 mmol) was reacted as described under General Procedure F to give the title compound (90 mg, 56%) as a white solid after column chromatography. $^1$H NMR (300 MHz, $d_6$-DMSO) δ 7.68 (d, 2H), 7.30 (d, 2H), 7.21 (s, 2H), 6.93 (d, 1H), 6.58 (d, 1H), 6.48 (dd, 1H), 5.05 (t, 1H), 3.30-3.13 (m, 2H), 2.05 (s, 3H), 1.87 (d, 1H), 1.54 (q, 1H), 1.27 (s, 3H), 0.78 (s, 3H). ESIMS m/z [M+H]$^+$ 379.1. Mp=60-62° C.

Example 23: ±trans 4-[3-{[(5-fluoro-2-methoxyphenyl)amino]methyl}-2,2-dimethylcyclopropyl]benzenesulfonamide

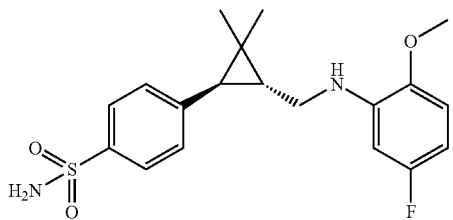 [SMILES: COc1ccc(F)cc1NC[C@@H]1[C@@H](c2ccc(S(N)(=O)=O)cc2)C1(C)C]

Intermediate BH (150 mg, 0.38 mmol) was reacted as described under General Procedure F to give the title compound (70 mg, 49%) as a white solid after column chromatography. $^1$H NMR (300 MHz, $d_6$-DMSO) δ 7.68 (d, 2H), 7.31 (d, 2H), 7.22 (s, 2H), 6.73 (dd, 1H), 6.42 (dd, 1H): 6.25 (dt, 1H), 5.03 (m, 1H), 3.73 (s, 3H), 3.22 (m, 2H), 1.87 (d, 1H), 1.56 (q, 1H), 1.26 (s, 3H), 0.77 (s, 3H). ESIMS m/z [M+H]$^+$ 379.1. Mp=164-166° C.

Example 24: ±trans 4-[3-{[(3-chlorophenyl)amino]methyl}-2,2-dimethylcyclopropyl]benzenesulfonamide

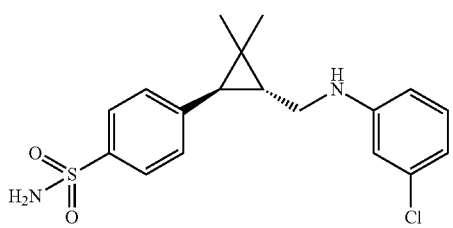 [SMILES: CC1(C)[C@H](CNc2cccc(Cl)c2)[C@H]1c1ccc(S(N)(=O)=O)cc1]

Intermediate BJ (100 mg, 0.22 mmol) was reacted as described under General Procedure F to give the title compound (35 mg, 36%) as a white foam after purification by column chromatography and semi-preparative HPLC. $^1$H NMR (300 MHz, $d_6$-DMSO) δ 7.69 (d, 2H), 7.33 (d, 2H), 7.22 (s, 2H), 7.05 (t, 1H), 6.63-6.62 (m, 1H), 6.56 (dd, 1H), 6.50 (dd, 1H), 5.94 (t, 1H), 3.23-3.11 (m, 2H), 1.85 (d, 1H), 1.46 (q, 1H), 1.25 (s, 3H), 0.79 (s, 3H). ESIMS m/z [M+H]$^+$ 365:1. Mp=120-122° C.

Example 25: ±trans 4-[3-{[(2-methoxyphenyl)amino]methyl}-2,2-dimethylcyclopropyl]benzenesulfonamide

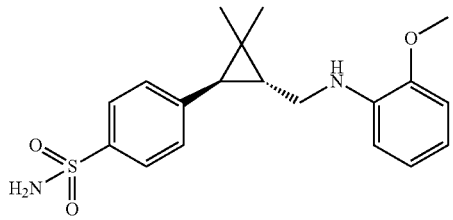 [SMILES: COc1ccccc1NC[C@@H]1[C@@H](c2ccc(S(N)(=O)=O)cc2)C1(C)C]

Example 4 (180 mg, 0.45 mmol) and Pd/C (10%, 18 mg) were suspended in EtOH (10 ml) and THF (5 ml) and stirred under an atmosphere of $H_2$ for 16 h. The mixture was filtered through Celite and purified by column chromatography (cyclohexane→1:1 EtOAc:cyclohexane) to give the described product as a yellow oil (70 mg, 43%). $^1$H NMR (300 MHz, $d_6$-DMSO) δ 7.68 (d, 2H), 7.30 (d, 2H), 7.22 (s, 2H), 6.80-6.74 (m, 2H), 6.63-6.51 (m, 2H), 4.66 (t, 1H), 3.75 (s, 3H), 3.23 (td, 2H), 1.87 (d, 1H), 1.57 (q, 1H); 1.28 (s, 3H), 0.78 (s, 3H). ESIMS m/z [M+F]$^+$ 361.2. Mp=115-117° C.

Example 26: ±trans 4-[2,2-dimethyl-3-({[3-(morpholin-4-yl)phenyl]amino}methyl)cyclopropyl]benzenesulfonamide

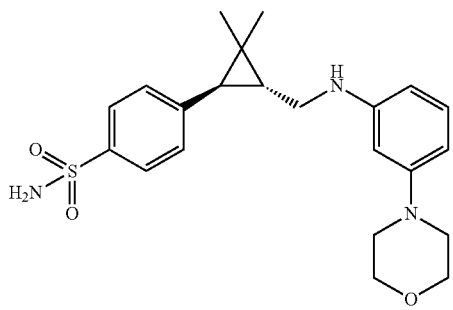 [SMILES: CC1(C)[C@H](CNc2cccc(N3CCOCC3)c2)[C@H]1c1ccc(S(N)(=O)=O)cc1]

Intermediate BL (200 mg, 0.46 mmol) was reacted as described under General Procedure F to give the title compound (156 mg, 80%) as a white solid after purification by column chromatography (cyclohexane→80% EtOAc/cyclohexane). $^1$H NMR (300 MHz, $d_6$-DMSO) δ 7.87-7.78 (m, 2H), 7.29-7.26 (m, 3H), 6.38 (t, 1H), 6.38-6.26 (m, 3H), 4.87 (br s, 2H), 3.82 (dd, 4H), 3.30 (d, 2H), 3.11 (dd, 4H), 1.83 (d, 1H), 1.51 (q, 1H), 1.30 (s, 3H), 0.86 (s, 3H). ESIMS m/z [M+H]$^+$ 416.2.

Example 27: ±trans 4-[3-{[(5-chloro-2-ethoxyphenyl)amino]methyl}-2,2-dimethylcyclopropyl]benzenesulfonamide

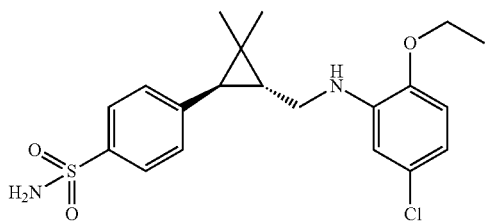 [SMILES: CCOc1ccc(Cl)cc1NC[C@@H]1[C@@H](c2ccc(S(N)(=O)=O)cc2)C1(C)C]

Intermediate BN (310 mg, 0.73 mmol) was reacted as described under General Procedure F to give the title compound (218 mg, 72%) as a white solid after purification by column chromatography (cyclohexane→60% EtOAc/cyclohexane). $^1$H NMR (300 MHz, CDCl$_3$) δ 7.82-7.80 (m 2H), 7.31-7.26 (m 2H), 6.66-6.57 (m, 3H), 5.29 (br s, 2H), 4.38 (br s, 1H), 4.03 (q, 2H), 3.35-3.21 (m, 2H), 1.85 (d, 1H), 1.54-1.32 (m, 7H), 0.87 (s, 3H). ESIMS m/z [M+H]$^+$ 409.1. Mp=122-124° C.

Example 28: ±trans 4-[3-({[2-methoxy-5-(trifluoromethyl)phenyl]amino}methyl)-2,2-dimethylcyclopropyl]benzenesulfonamide

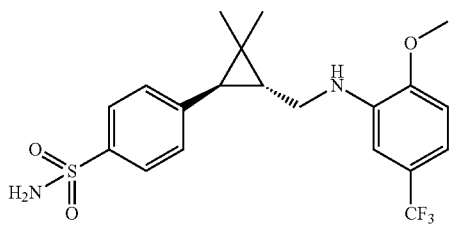 [SMILES: COc1ccc(C(F)(F)F)cc1NC[C@@H]1[C@@H](c2ccc(S(N)(=O)=O)cc2)C1(C)C]

Intermediate BP (220 mg, 0.49 mmol) was reacted as described under General Procedure F to give the title compound (60 mg, 29%) as a white solid after purification by column chromatography. $^1$H NMR (300 MHz, d$_6$-DMSO) δ 7.68 (d, 2H), 7.30 (d, 2H), 7.22 (s, 2H), 6.95-6.86 (m, 2H), 6.78 (s, 1H), 5.18 (br s, 1H); 3.84 (s, 3H), 3.29 (br s, 2H), 1.88 (d, 1H), 1.55 (q, 1H), 1.27 (s, 3H), 0.78 (s, 3H). ESIMS m/z [M+H]$^+$ 429.1. Mp=68-70° C.

Example 29: 4-[(1R,3R)-3-{[(5-fluoro-2-methylphenyl)amino]methyl}-2,2-dimethylcyclopropyl]benzenesulfonamide

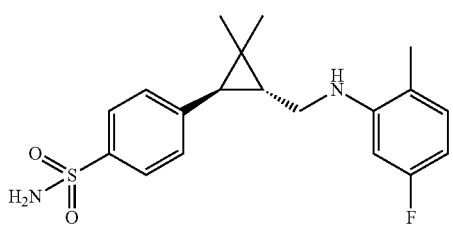 [SMILES: Cc1ccc(F)cc1NC[C@@H]1[C@@H](c2ccc(S(N)(=O)=O)cc2)C1(C)C]

Intermediate BR (180 mg, 0.48 mmol) was reacted as described under General Procedure F to give the title compound (95 mg, 54%) as a white foam. $^1$H NMR (300 MHz, CDCl$_3$) δ 7.82 (d, 2H), 7.29 (d, 2H), 6.99 (t, 1H), 6.43-6.36 (m, 2H), 4.87 (s, 2H), 3.40-3.21 (m, 2H). 2.11 (s, 3H), 1.86 (d, 1H). 1.58-1.50 (m, 2H), 1.31 (s, 3H), 0.87 (s, 3H). ESIMS m/z [M+H]$^+$ 363.1.

Example 30: 4-[(1R,3R)-3-{[(4,5-difluoro-2-methylphenyl)amino]methyl}-2,2-dimethylcyclopropyl]benzenesulfonamide

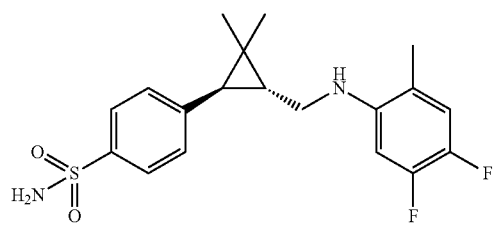 [SMILES: Cc1cc(F)c(F)cc1NC[C@@H]1[C@@H](c2ccc(S(N)(=O)=O)cc2)C1(C)C]

Intermediate BT (240 mg, 0.61 mmol) was reacted as described under General Procedure F to give the title compound (65 mg, 28%) as a white foam. $^1$H NMR (300 MHz, CDCl$_3$) δ 7.82 (d, 2H), 7.28 (d, 2H), 6.93-6.86 (m, 1H), 6.53 (br s, 1H), 4.86 (s, 1H), 3.36-3.18 (m, 2H), 2.24 (s, 3H), 1.86 (d, 1H), 1.60-1.49 (m, 2H), 1.29 (s, 3H), 0.86 (s, 3H). ESIMS m/z [M+H]$^+$ 381.1. Mp=210-212° C.

Example 31: 4-[(1S,3S)-3-{[(5-fluoro-2-methylphenyl)amino]methyl}-2,2-dimethylcyclopropyl]benzenesulfonamide

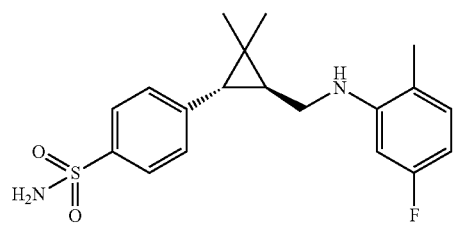 [SMILES: Cc1ccc(F)cc1NC[C@H]1[C@H](c2ccc(S(N)(=O)=O)cc2)C1(C)C]

Intermediate BV (180 mg, 0.48 mmol) was reacted as described under General Procedure F to give the title compound (95 mg, 54%) as a white solid after purification by column chromatography (cyclohexane→1:1 EtOAc/cyclohexane). $^1$H NMR (300 MHz, CDCl$_3$) δ 7.84-7.81 (m, 2H), 7.30-7.26 (m, 2H), 6.99 (t, 1H), 6.43-6.38 (m, 2H), 4.88 (br s, 2H), 3.40-3.22 (m, 2H), 2.11 (s, 3H), 1.86 (d, 1H), 1.60-53 (m, 2H), 1.31 (s, 3H), 0.87 (s, 3H). ESIMS m/z [M+H]$^+$ 363.1.

Example 32: 4-[(1S,3S)-3-{[(4,5-difluoro-2-methyl-phenyl)amino]methyl}-2,2-dimethylcyclopropyl]benzenesulfonamide

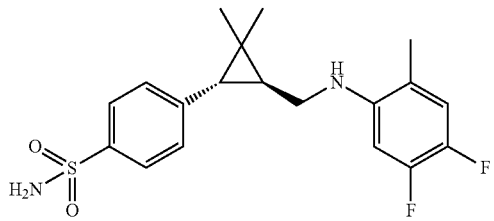 [SMILES: Cc1cc(F)c(F)cc1NC[C@H]1[C@H](c2ccc(S(N)(=O)=O)cc2)C1(C)C]

Intermediate BX (176 mg, 0.43 mmol) was reacted as described under General Procedure F to give the title compound (100 mg, 61%) as a white solid after purification by column chromatography (cyclohexane→1:1 EtOAc/cyclohexane). $^1$H NMR (300 MHz, CDCl$_3$) δ 7.83 (d, 2H), 7.28 (d, 2H), 6.88 (m, 1H), 6.52-6.40 (m, 1H), 4.87 (br s, 2H), 3.34-3.18 (m, 2H), 2.11 (s, 3H), 1.86 (d, 1H), 1.56-1.53 (m, 2H), 1.31 (s, 3H), 0.87 (s, 3H). ESIMS m/z [M+H]$^+$ 381.1.

Example 33: ±trans 4-[3-({[4-fluoro-3-(trifluoromethyl)phenyl]amino}methyl)-2,2-dimethylcyclopropyl]benzenesulfonamide

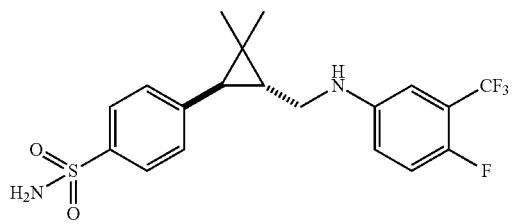

Intermediate BZ (128 mg, 0.50 mmol) was dissolved in anhydrous THF (16 ml) and the solution was degassed with N$_2$. MnO$_2$ (7 g, 80.5 mmol) was added in one portion and the mixture allowed to stir for 3.5 h at ambient temperature. The reaction mixture was filtered through Celite directly onto 5-amino-2-fluorobenzotrifluoride (94 mg, 0.53 mmol) and rinsed through with anhydrous THF. The solution was stirred at ambient temperature for 25 min after which time the mixture was concentrated in vacuo and the residue taken up in 1,2-DCE (3 ml). NaBH(OAc)$_3$ (212 mg, 1.00 mmol) was added followed by acetic acid (90 μl, 1.5 mmol) and the reaction mixture stirred at room temperature for 1.5 h, the reaction was then quenched with NaHCO$_3$ (sat. aq.) and the phases separated. The aqueous phase was extracted with DCM (2×) and the combined organic extracts washed with brine, dried (MgSO$_4$) and concentrated in vacuo. The product was purified by pTLC to give the title compound as a white solid (95 mg, 46%). $^1$H NMR (300 MHz, CDCl$_3$) δ 7.86-7.81 (m, 2H), 7.30-7.27 (m, 2H), 7.02 (t, 1H), 6.80-6.71 (m, 2H), 4.82 (s, 2H), 3.55 (br, 1H), 3.34-3.20 (m, 2H), 1.85 (d, 1H), 1.60-1.44 (m, 1H), 1.28 (s, 3H), 0.87 (s, 3H). ESIMS m/z [M−H]$^−$ 415.3.

Example 34: ±trans 4-[3-({[2-(difluoromethoxy)-4-fluorophenyl]amino}methyl)-2,2-dimethylcyclopropyl]benzenesulfonamide

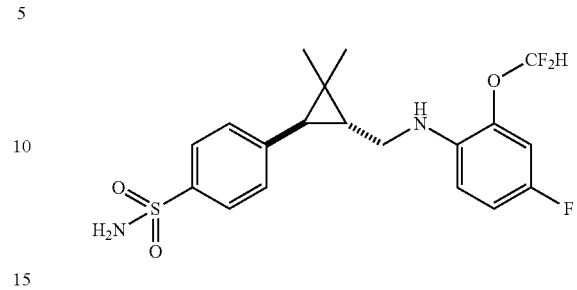

Intermediate BZ (122 mg, 0.478 mmol) and 2-(difluoromethoxy)-4-fluoroaniline (89 mg, 0.502 mmol) were reacted as described under Example 33 to give the title compound after recrystallization from EtOAc/pentane (21 mg, 11%). $^1$H NMR (300 MHz, d$_3$-MeOD) δ 7.80-7.77 (m, 2H), 7.32-7.30 (m, 2H), 6.90-6.80 (m, 3H), 6.67 (t, 1H), 3.36-3.30 (m, 2H), 1.92 (d, 1H), 1.60-1.53 (m, 1H), 1.33 (s, 3H), 0.84 (s, 3H). ESIMS m/z [M+H]$^+$ 415.0.

Example 35: ±trans 4-(3-{[(5-tert-butyl-1,2-oxazol-3-yl)amino]methyl)}2,2-dimethylcyclopropyl)benzenesulfonamide

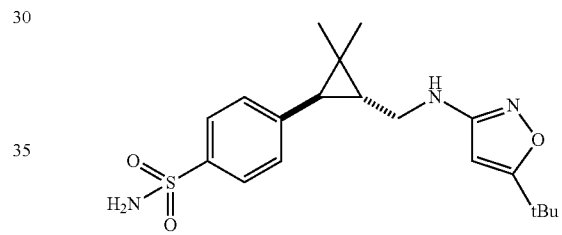

Intermediate BZ (116 mg, 0.454 mmol) and 3-amino-5-tert-butylisoxazole (67 mg, 0.477 mmol) were reacted as described under Example 33. The product was purified by two pTLC plates (40% EtOAc/CHCl$_3$) one column (80% Et$_2$O/hexane) and then triturating with iPrOH, to remove the residual 3-amino-5-tbutylisozazole that was contaminating the product, to give the title compound (26 mg, 15%) as a solid. $^1$H NMR (300 MHz, CDCl$_3$) δ 7.82 (d, 2H), 7.29 (d, 2H), 5.47 (s, 1H), 4.72 (s, 2H), 3.83 (br t, 1H), 3.41-3.35 (m, 2H), 1.82 (d, 1H), 1.57-1.50 (m, 1H), 1.31 (s, 3H), 1.30 (s, 9H), 0.84 (s, 3H). ESIMS m/z [M−H]$^−$ 376.3.

Example 36: ±trans 4-[2,2-dimethyl-3-{[(2-methyl-pyridin-3-yl)amino]methyl}cyclopropyl]benzenesulfonamide

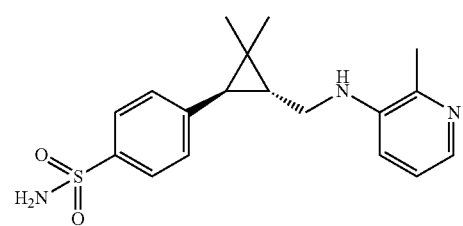 [SMILES: Cc1ncccc1NC[C@@H]1[C@@H](c2ccc(S(N)(=O)=O)cc2)C1(C)C]

Intermediate CB (160 mg, 0.44 mmol) was reacted as described under General Procedure F to give the title compound (70 mg, 46%) as a white solid after purification by column chromatography (cyclohexane→1:1 EtOAc/cyclohexane). $^1$H NMR (300 MHz, d$_6$-DMSO) δ 7.68-7.64 (m, 3H), 7.30-7.25 (m, 4H), 7.00-6.90 (m, 2H), 5.12-5.08 (m, 1H), 3.32-3.21 (m, 2H), 2.29 (s, 3H), 1.87 (d, 1H), 1.54 (q, 1H), 1.27 (s, 3H), 0.77 (s, 3H). ESIMS m/z [M+H]$^+$ 346.2. Mp=174-176° C.

Example 37: ±trans 4-[3-{[(3-chloro-4-fluoro-2-methylphenyl)amino]methyl}-2,2-dimethylcyclopropyl]benzenesulfonamide

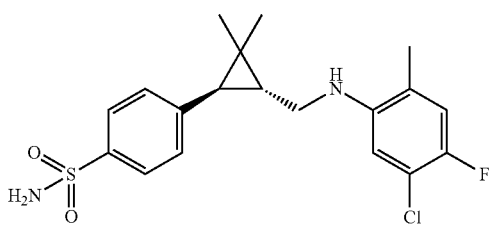 [SMILES: Cc1cc(F)c(Cl)cc1NC[C@@H]1[C@@H](c2ccc(S(N)(=O)=O)cc2)C1(C)C]

Intermediate CD (700 mg, 1.76 mmol) was reacted as described under General Procedure F to give the title compound (410 mg, 59%) as a white solid after purification by column chromatography (cyclohexane→1:1 EtOAc/cyclohexane). $^1$H NMR (300 MHz, d$_6$-DMSO) δ 7.68 (d, 2H), 7.30 (d, 2H), 7.26 (s, 2H), 7.04 (d, 1H), 6.63 (d, 1H), 4.96 (t, 1H), 3.29-3.12 (m, 2H), 2.07 (s, 3H), 1.86 (d, 1H), 1.52 (q, 1H), 1.26 (s, 3H), 0.77 (s, 3H). ESIMS m/z [M+H]$^+$ 397.1. Mp=164-166° C.

Example 38: ±trans 4-[-3-{[(4-fluoro-2-methylphenyl)amino]methyl}-2,2-dimethylcyclopropyl]benzenesulfonamide

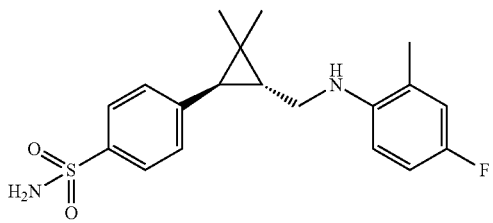 [SMILES: Cc1cc(F)ccc1NC[C@@H]1[C@@H](c2ccc(S(N)(=O)=O)cc2)C1(C)C]

Example 37 (320 mg, 0.8 mmol) was reacted as described under Example 25 to give the title compound (200 mg, 69%) as a white foam after purification by column chromatography (cyclohexane→1:1 EtOAc/cyclohexane). $^1$H NMR (300 MHz, d$_6$-DMSO) δ 7.68 (d, 2H), 7.29 (d, 2H), 7.24 (s, 2H), 6.88-6.72 (m, 2H), 6.70-6.62 (m, 1H), 4.60 (br s, 1H), 3.21-3.11 (m, 2H), 2.08 (s, 3H), 1.86 (d, 1H), 1.53 (q, 1H), 1.26 (s, 3H), 0.77 (s, 3H). ESIMS m/z [M+H]$^+$ 363.2.

Example 39: ±trans 4-[3-{[(2-ethyl-5-fluorophenyl)amino]methyl}-2,2-dimethylcyclopropyl]benzenesulfonamide

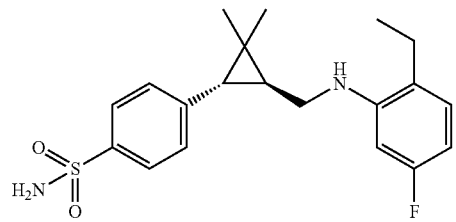 [SMILES: CCc1ccc(F)cc1NC[C@H]1[C@H](c2ccc(S(N)(=O)=O)cc2)C1(C)C]

Intermediate CF (0.500 g, 1.3 mmol) was reacted as described under General Procedure F to give the title compound (200 mg, 41%) as a white solid after purification by column chromatography (cyclohexane→1:1 EtOAc/cyclohexane). $^1$H NMR (300 MHz, d$_6$-DMSO) δ 7.67 (d, 2H), 7.31-7.25 (m, 4H), 6.91 (t, 1H), 6.39 (dd, 1H), 6.26 (dt, 1H), 5.17 (br s, 1H), 3.23 (m, 2H), 2.42 (q, 2H), 1.87 (d, 1H), 1.55 (q, 1H), 1.26 (s, 3H), 1.09 (d, 3H), 0.76 (s, 3H). ESIMS m/z [M+H]$^+$ 377.1.

Example 40: ±trans 4-[3-({[2-fluoro-5-(trifluoromethoxy)phenyl]amino}methyl)-2,2-dimethylcyclopropyl]benzenesulfonamide

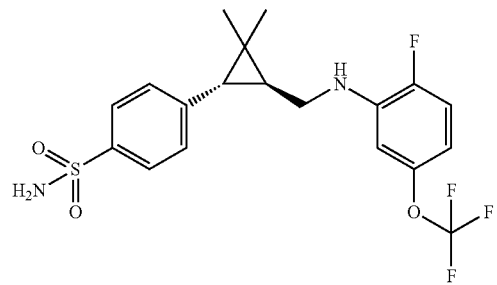 [SMILES: CC1(C)[C@@H](CNc2cc(OC(F)(F)F)ccc2F)[C@@H]1c1ccc(S(N)(=O)=O)cc1]

Intermediate CI (200 mg, 0.45 mmol) was reacted as described under General Procedure F to give the title compound (70 mg, 36%) as a clear colourless oil after purification by column chromatography (cyclohexane→1:1 EtOAc/cyclohexane). $^1$H NMR (300 MHz, d$_6$-DMSO) δ 7.66 (d, 2H), 7.30-7.25 (m, 4H), 7.09 (dd, 1H), 6.72 (dd, 1H), 6.46-6.43 (m, 1H), 5.95 (br s, 1H), 3.33-3.22 (m, 2H), 1.86 (d, 1H), 1.55 (q, 1H), 1.25 (s, 3H), 0.75 (s, 3H). ESIMS m/z [M+H]$^+$ 433.1.

Example 41: ±trans 4-[3-({[5-fluoro-2-(trifluoromethoxy)phenyl]amino}methyl)-2,2-dimethylcyclopropyl]benzenesulfonamide

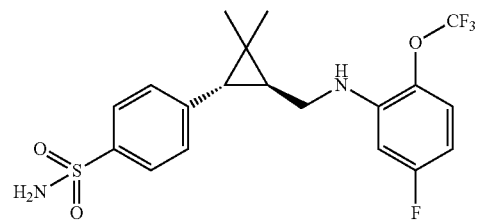 [SMILES: CC1(C)[C@@H](CNc2cc(F)ccc2OC(F)(F)F)[C@@H]1c1ccc(S(N)(=O)=O)cc1]

Intermediate CJ (130 mg, 0.3 mmol) was reacted as described under General Procedure F to give the title compound (60 mg, 46%) as a clear colourless oil after purification by column chromatography (cyclohexane→1:1 EtOAc/cyclohexane). $^1$H NMR (300 MHz, d$_6$-DMSO) δ 7.66 (d, 2H), 7.29-7.24 (m, 4H), 7.17-7.11 (m, 1H), 6.69 (dd, 1H), 6.32. (dt, 1H), 5.96 (br s, 1H), 3.35-3.20 (m, 2H), 1.86 (d, 1H), 1.56 (q, 1H), 1.24 (s, 3H), 0.74 (s, 3H). ESIMS m/z [M+H]$^+$ 433.1.

Example 42: ±trans 4-(3-{[(2-methoxypyridin-3-yl)amino]methyl}-2,2-dimethylcyclopropyl)benzenesulfonamide

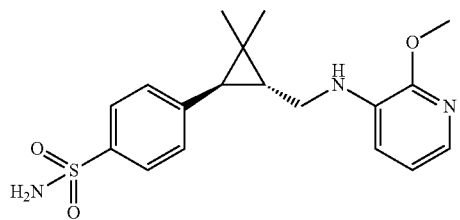 [SMILES: COc1ncccc1NC[C@@H]1[C@@H](c2ccc(S(N)(=O)=O)cc2)C1(C)C]

Intermediate CK (135 mg, 0.53 mmol) was reacted as described under General Procedure I to furnish the title compound as a white solid (30 mg, 47%) after purification by column chromatography (100% cyclohexane→50% EtOAc/cyclohexane). $^1$H NMR (300 MHz, d$_6$-DMSO) δ 7.67 (d, 2H), 7.35-7.24 (m, 5H), 6.86-6.74 (m, 2H), 5.03-4.99 (m, 1H), 3.85 (s, 3H), 3.25-3.19 (m, 2H), 1.87 (d, 1H), 1.67 (q, 1H), 1.25 (s, 3H), 0.77 (s, 3H). ESIMS m/z [M+H]$^+$ 362.2. Mp=98-100° C.

Example 43: ±trans 4'-[3-{[(5-chloro-2-methoxyphenyl)amino]methyl}-2,2-dimethylcyclopropyl]biphenyl-2-ol

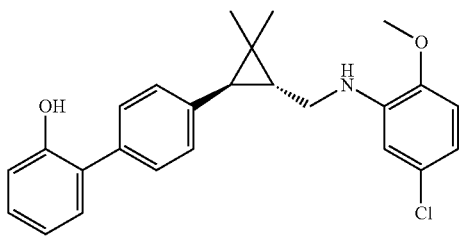 [SMILES: COc1ccc(Cl)cc1NC[C@@H]1[C@@H](c2ccc(-c3ccccc3O)cc2)C1(C)C]

Intermediate CP (135 mg, 0.32 mmol) was reacted as described under General Procedure F to give the title compound as a white solid (102 mg, 78%) after purification by column chromatography (cyclohexane→60% cyclohexane/EtOAc). $^1$H NMR (300 MHz, CDCl$_3$) δ 7.40-7.36 (m, 2H), 7.32-7.22 (m, 5H), 7.00-6.97 (m, 2H), 6.66 (s, 3H), 5.26 (br s, 1H), 3.84 (s, 3H), 3.29 (dq, 2H), 1.83 (d, 1H), 1.54-1.43 (m, 1H), 1.31 (s, 3H), 0.93 (s, 3H). ESIMS m/z [M+H]$^+$ 408.1.

Example 44: ±trans 4-[3-{[(2-ethoxyphenyl)amino]methyl}-2,2-dimethylcyclopropyl]benzenesulfonamide

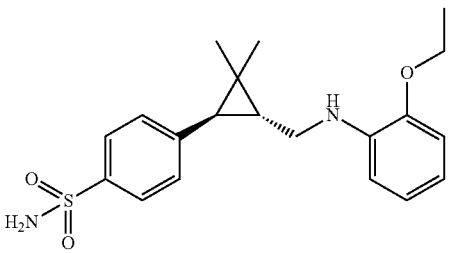 [SMILES: CCOc1ccccc1NC[C@@H]1[C@@H](c2ccc(S(N)(=O)=O)cc2)C1(C)C]

Example 27 (98 mg, 0.24 mmol) was reacted as described under Example 25 to furnish the title compound as a white solid (50 mg, 56%) after purification by column chromatography. $^1$H NMR (300 MHz, d$_6$-DMSO) δ 7.70 (d, 2H), 7.32 (d, 2H), 7.26 (s, 2H), 6.81-6.75 (m, 2H), 6.65 (d, 1H), 6.54 (t, 1H), 4.63 (m, 1H), 4.01 (q, 2H), 3.27-3.23 (m, 2H), 1.90 (d, 1H), 1.58 (q, 1H), 1.32 (t, 3H), 1.29 (s, 3H), 0.80 (s, 3H). ESIMS m/z [M+H]$^+$ 375.1. Mp=46-48° C.

Example 45: ±trans 4-[3-({[5-chloro-2-(trifluoromethyl)phenyl]amino}methyl)-2,2-dimethylcyclopropyl]benzenesulfonamide

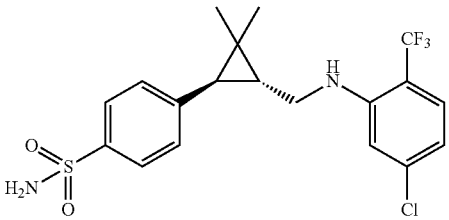 [SMILES: CC1(C)[C@H](CNc2cc(Cl)ccc2C(F)(F)F)[C@H]1c1ccc(S(N)(=O)=O)cc1]

Intermediate CR (150 mg, 0.36 mmol) was reacted as described under General Procedure F to furnish the title compound as a white solid (50 mg, 32%) after purification by chromatography. $^1$H NMR (300 MHz, d$_6$-DMSO) δ 7.67 (d, 2H), 7.40 (d, 1H), 7.28 (d, 2H), 7.23 (s, 2H), 6.95 (s, 1H), 6.68 (d, 1H), 5.53 (m, 1H), 3.40-3.36 (m, 2H), 1.90 (d, 1H), 1.54 (q, 1H), 1.26 (s, 3H), 0.76 (s, 3H). ESIMS m/z [M+H]$^+$ 433.0. Mp=124-126° C.

Example 46: ±trans N-{4-[3-{[(5-chloro-2-methoxyphenyl)amino]methyl}-2,2-dimethylcyclopropyl]phenyl}methanesulfonamide

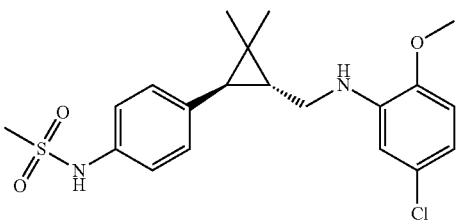

Intermediate CS (150 mg, 0.35 mmol) was reacted as described under General Procedure F to furnish the title compound as a white solid (137 mg, 94%) after purification by chromatography (100% cyclohexane→60% EtOAc/cyclohexane). ¹H NMR (300 MHz, CDCl₃) δ 7.13 (s, 4H), 6.73-6.69 (m, 2H), 6.48 (br s, 1H), 3.84 (s, 3H), 3.35-3.25 (m, 2H), 2.99 (s, 3H), 2.00 (s, 2H), 1.75 (d, 1H), 1.46-1.42 (m, 1H), 1.25 (s, 3H), 0.84 (s, 3H). ESIMS m/z [M+H]⁺ 409.1.

Example 47: Enantiomer A of trans N-{4-[3-{[(8-chloro-2-methoxyphenyl)amino]methyl}-2,2-dimethylcyclopropyl]phenyl}methanesulfonamide Example 48: Enantiomer B of trans N-(4-[3-{[(5-chloro-2-methoxyphenyl)amino]methyl}-2,2-dimethylcyclopropyl]phenyl)methanesulfonamide

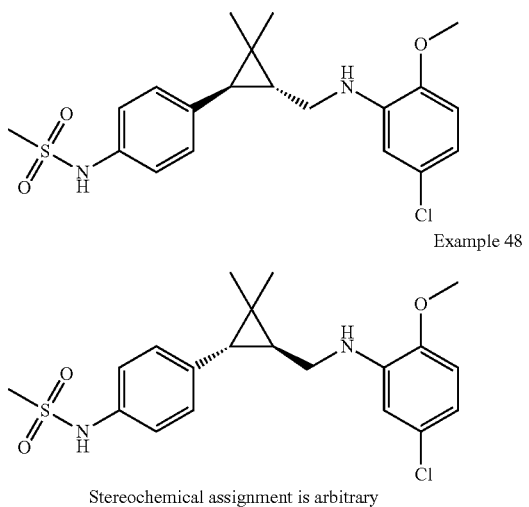

Example 47

Example 48

Stereochemical assignment is arbitrary

The trans-racemate Example 46 was separated into individual, enantiomers by preparative HPLC (Chiralpak OJ-H (20×250) mm, 5 μm, 10 mL/min, n-Hexane:Ethanol, 1:1, Inj. V., 200 μL (10 mg/injection)), Example 47 is the first eluting isomer, Rt=17.45 min, 100% ee, and Example 48 is the second eluting Isomer, Rt=26.03 min, 100% ee.

Example 49: ±trans 4-[2-{[(3-methylpyridin-2-yl)amino]methyl}spiro[2.4]hept-1-yl]benzenesulfonamide

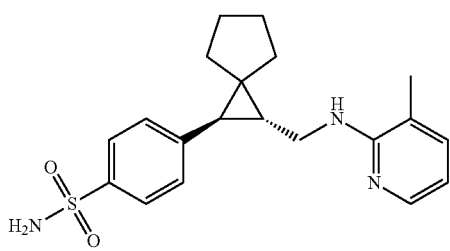 [SMILES: Cc1cccnc1NC[C@@H]1[C@@H](c2ccc(S(N)(=O)=O)cc2)C12CCCC2]

Intermediate CV (140 mg, 0.50 mmol) and 3-methyl-2-pyridinamine (54 mg, 0.05 mmol) were reacted as described under General Procedure I to furnish the title compound as a white solid (18 mg, 10%) after purification by column chromatography followed by p-TLC. ¹H NMR (300 MHz, d₆-DMSO) δ 7.86 (d, 1H), 7.67 (d, 2H), 7.21-7.17 (m, 5H), 6.41 (dd, 1H), 5.83 (t, 1H), 3.51-3.35 (m, 2H), 2.01 (s, 3H), 1.96-1.89 (m, 3H), 1.83-1.37 (m, 6H), 1.12-1.00 (m, 1H). ESIMS m/z [M+H]⁺ 372.2. Mp=82-84° C.

Example 50: 4-[(1S,3S)-3-({[2-(difluoromethoxy)-4-fluorophenyl]amino}methyl)-2,2-dimethylcyclopropyl]benzenesulfonamide

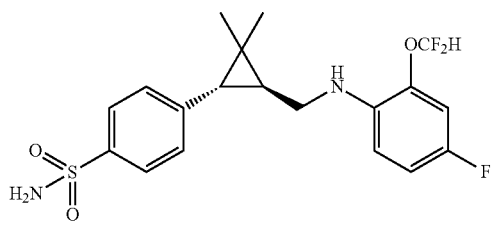

Intermediate CY (130 mg, 0.51 mmol) and 2-(difluoromethoxy)-4-fluoroaniline (95 mg, 0.54 mmol) were reacted as described for Example 33 to furnish the title compound as a pale pink oil (85 mg, 40%) following purification by pTLC (30% EtOAc/hexane). ¹H NMR (300 MHz, CDCl₃) δ 7.83 (d, 2H), 7.28 (d,), 6.89-6.82 (m, 2H), 6.69-5.20 (m, 2H), 4.81 (s, 2H), 4.03 (br s, 1H), 3.35 (dd, 1H), 3.21 (dd, 1H), 1.84 (d, 1H), 1.52-1.46 (m, 1H), 1.31 (s, 3H), 1.86 (s, 3H). ESIMS m/z [m+H]⁺ 415.0.

Example 51: 4-[(1R,3R)-3-({[2-(difluoromethoxy)-4-fluorophenyl]amino}methyl)-2,2-dimethylcyclopropyl]benzenesulfonamide

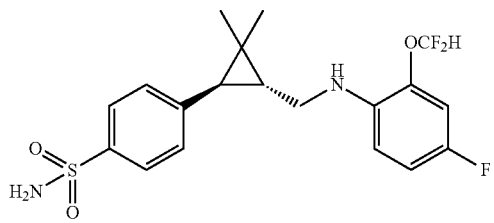

Intermediate DB (130 mg, 0.51 mmol) and 2-(difluoromethoxy)-4-fluoroaniline (95 mg, 0.54 mmol) were reacted as described under Example 33 to furnish the title compound as a pale pink oil (97 mg, 46%) following purification by pTLC (35% EtOAc/hexane). ¹H NMR (300 MHz, CDCl₃) δ 7.83 (d, 2H), 7.28 (d, 2H), 6.90-6.83 (m, 2H), 6.69-5.20 (m, 2H), 4.76 (s, 2H), 4.03 (br s, 1H), 3.35 (dd, 1H), 3.21 (dd, 1H), 1.84 (d, 1H), 1.53-1.46 (m, 1H), 1.32 (s, 3H), 1.86 (s, 3H). ESIMS m/z [M+H]⁺ 415.0

Example 52: 4-[(1S,2S)-2-({[5-fluoro-2-(trifluoromethoxy)phenyl]amino}methyl)cyclopropyl]benzenesulfonamide

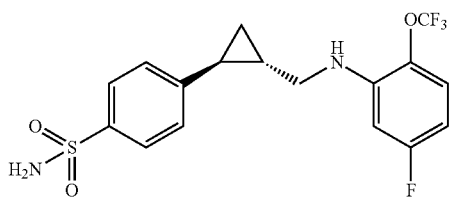

Intermediate DD (190 mg, 0.45 mmol) was reacted as described under General Procedure F to furnish the title compound as a white solid (17 mg, 9%) after purification by column chromatography. $^1$H NMR (300 MHz, d$_6$-DMSO) δ 7.64 (d, 2H), 7.20-7.11 (m, 5H), 6.66 (dd, 1H), 6.32 (td,), 6.11-6.08 (m, 1H), 3.19 (t, 2H), 1.98-1.92 (m, 1H), 1.43 (m, 1H) 1.03-0.97 (m, 2H). ESIMS m/z [M+H]$^+$ 405.1. Mp=115-118° C.

Example 53: 4-[(1R,2R)-2-({[5-fluoro-2-(trifluoromethoxy)phenyl]amino}methyl)cyclopropyl]benzenesulfonamide

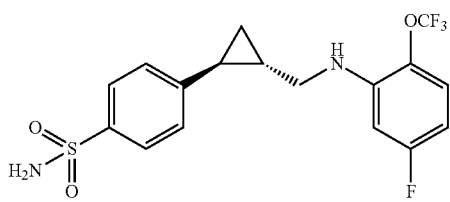 [SMILES: NS(=O)(=O)c1ccc([C@H]2C[C@@H]2CNc2cc(F)ccc2OC(F)(F)F)cc1]

Intermediate DF (120 mg, 0.29 mmol) was reacted as described under General Procedure F to furnish the title compound as a white solid (55 mg, 47%) after purification by column chromatography. $^1$H NMR (300 MHz, d$_6$-DMSO) δ 7.64 (d, 2H), 7.20-7.11 (m, 5H), 6.66 (dd, 1H), 6.32 (td, 1H), 6.11-6.08 (m, 1H), 3.19 (t, 2H), 1.98-1.92 (m, 1H), 1.43 (m, 1H) 1.03-0.97 (m, 2H). ESIMS [M+H]$^+$ 405.1. Mp=115-118° C.

Example 54: ±trans 4-{[-2-{[(5-chloro-2-methoxyphenyl)amino]methyl}cyclopropyl]methyl}benzenesulfonamide

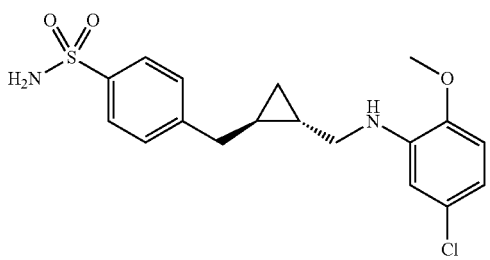 [SMILES: COc1ccc(Cl)cc1NC[C@H]1C[C@@H]1Cc1ccc(S(N)(=O)=O)cc1]

Intermediate DI (1.0 g, 3.5 mmol) was reacted as described under General Procedure F to furnish the title compound as a white solid (500 mg, 53%) after purification by column chromatography. $^1$H NMR (300 MHz, d$_6$-DMSO) δ 7.72 (d, 2H), 7.45 (d, 2H), 7.23 (s, 2H), 6.75 (d, 1H), 6.53-6.50 (m, 2H), 4.80-4.72 (m, 1H), 3.74 (s, 3H), 3.17-3.08 (m, 2H), 2.85-2.26 (m, 2H), 1.26-1.09 (m, 2H), 0.77-0.71 (m, 1H), 0.26-0.18 (m, 1H). ESIMS m/z [M+H]$^+$ 381.1. Mp=126-128° C.

Example 55: ±trans 4-[3-{[(5-chloro-2-methoxyphenyl)amino]methyl}-2,2-dimethylcyclopropyl]-N-hydroxybenzenesulfonamide

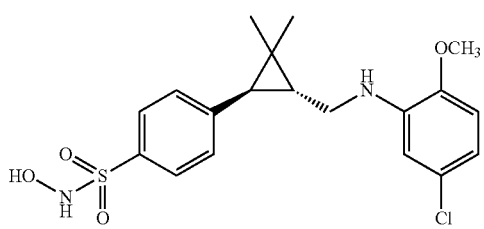 [SMILES: COc1ccc(Cl)cc1NC[C@@H]1[C@@H](c2ccc(S(=O)(=O)NO)cc2)C1(C)C]

Intermediate DK (49 mg, 0.12 mmol) was reacted as described under General Procedure F to furnish the title compound (12 mg, 95%) after purification by pTLC (40% EtOAc/hexane). $^1$H NMR (300 MHz, CDCl$_3$) δ 7.87-7.83 (m, 2H), 7.36-7.32 (m, 2H), 6.71-6.59 (m, 4H), 6.22 (brs, 1H), 3.83 (s, 3H), 3.30-3.25 (m, 2H), 1.86 (d, 1H), 1.67 (brs, 1H), 1.54 (q, 1H), 1.33 (s, 3H), 0.88 (s, 3H). ESIMS m/z [M+H]$^+$ 411.0.

Example 56: ±trans 4-[3-{[(5-chloro-2-methoxyphenyl)amino]methyl}-2,2-dimethylcyclopropyl]benzenesulfonohydrazide

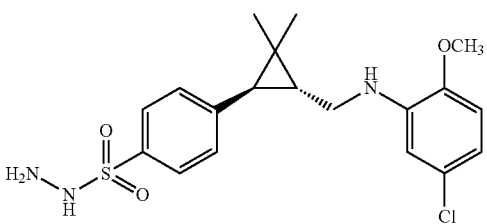 [SMILES: COc1ccc(Cl)cc1NC[C@@H]1[C@@H](c2ccc(S(=O)(=O)NN)cc2)C1(C)C]

Intermediate DL (0.200 g, 0.47 mmol) was reacted as described under General Procedure F to furnish the title compound as a crystalline solid (36 mg, 19%) after purification by column chromatography (50% EtOAc/hexane) followed by recrystallisation from Et$_2$O. $^1$H NMR (300 MHz, CDCl$_3$) δ 7.83-7.79 (m, 2H), 7.35-7.32 (m, 2H), 6.68-6.58 (m, 3H), 5.57 (brs, 1H), 4.34 (br s, 1H), 3.83 (s, 3H), 3.62 (brs, 2H), 3.35-3.20 (m, 2H), 1.86 (d, 1H), 1.53 (q, 1H), 1.33 (s, 3H), 0.88 (s, 3H). ESIMS m/z [M+H]$^+$ 410.0.

Example 57: Enantiomer A of trans 4-[3-{[(4-fluoro-2-methylphenyl)amino]methyl}-2,2-dimethylcyclopropyl]benzenesulfonamide Example 58: Enantiomer B of trans 4-[3-{[(4-fluoro-2-methylphenyl)amino]methyl}-2,2-dimethylcyclopropyl]benzenesulfonamide

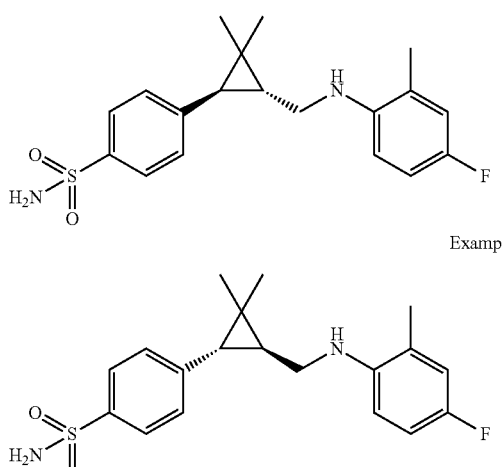

Stereochemical assignment is arbitrary

The trans-racemate Example 38 was separated into individual enantiomers by SFC (Lux cellulose-3 (250×4.6) mm, 5 m, CO$_2$/Methanol 7:3, 3 mLmin$^{-1}$, 35° C., 100 bar), Example 57 is the first eluting isomer, Rt=5.58 min, 100% ee, and Example 58 is the second eluting isomer, Rt=7.20 min, 100% ee.

Example 59: ±trans N-[4-(3-{[(5-chloro-2-methoxyphenyl)amino]methyl}-2,2-dimethylcyclopropyl)phenyl]sulfuric diamide

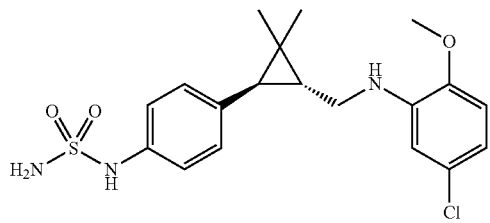 [SMILES: COc1ccc(Cl)cc1NC[C@@H]1[C@@H](c2ccc(NS(N)(=O)=O)cc2)C1(C)C]

A small Schlenk flask was charged with K$_3$PO$_4$ (1.91 g, 9.0 mmol) under a dry atmosphere of nitrogen (drying tube fitted), 1,4-dioxane (33 ml) was added followed by BuXPhos (104 mg, 0.245 mmol) and Pd$_2$(dba)$_3$ (75 mg, 0.0818 mmol). The mixture was freeze-pump-thaw degassed three times. Intermediate DO (3.23 g, 8.18 mmol) and sulfamide (944 mg, 9.82 mmol) were added and the reaction mixture stirred under a nitrogen atmosphere at room temperature for 30 minutes before heating to 80° C. overnight. The reaction mixture was cooled to room temperature, diluted with EtOAc and washed with HCl (1M aq. 2×), dried (MgSO$_4$) and concentrated in vacuo. The product was purified by pTLC (40% EtOAc/hexane) to yield 111 mg (3%) of the title compound. $^1$H NMR (300 MHz, CDCl$_3$) δ 7.15 (s, 4H), 6.67-6.57 (m, 3H), 6.38 (br s, 1H), 4.66 (br s, 2H), 4.35 (br s, 1H), 3.83 (s, 3H), 3.30-3.18 (m 2H), 1.76 (d, 1H), 1.39 (q, 1H), 1.29 (s, 3H), 0.88 (s, 3H). ESIMS m/z [M+H]$^+$ 410.0.

Example 60: Enantiomer A of trans N-[4-(3-{[(6-chloro-2-methoxyphenyl)amino]methyl}-2,2-dimethylcyclopropyl)phenyl]sulfuric diamide Example 61: Enantiomer B of trans N-[4-(3-{[(5-chloro-2-methoxyphenyl)amino]methyl}-2,2-dimethylcyclopropyl)phenyl]sulfuric diamide

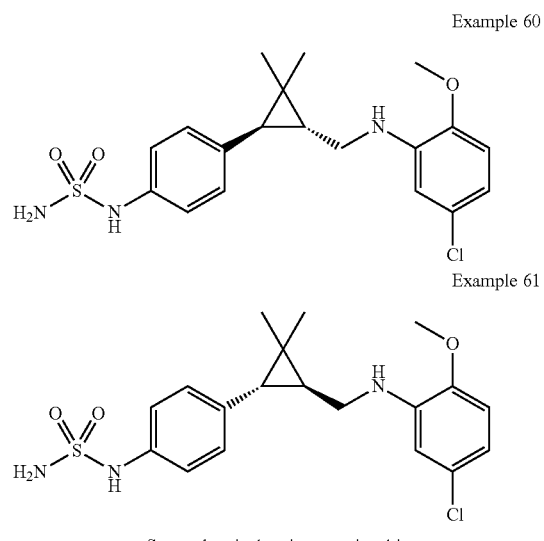

Stereochemical assignment is arbitrary

The trans-racemate Example 59 was separated into individual enantiomers by chiral HPLC (Chiralcel OJ-H (250× 4.6) mm, 5 μm, mobile phase n-hexane:EtOH 30:70, 1 mLmin$^{-1}$), Example 60 is the first eluting isomer, Rt=11.9 min, 100% ee, and Example 61 is the second eluting isomer, Rt=19.3 min, 98.14% ee.

Example 62: trans 4-(3-{[(2,2-difluorocyclohexyl)amino]methyl}-2,2-dimethylcyclopropyl)benzenesulfonamide

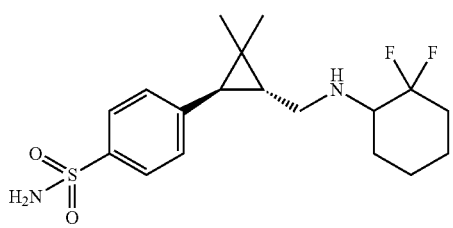 [SMILES: CC1(C)[C@H](CNC2CCCCC2(F)F)[C@H]1c1ccc(S(N)(=O)=O)cc1]

Intermediate DQ (0.415 g) was reacted as described under General Procedure F to furnish the title compound (27 mg) as a colourless solid, as a pair of diastereomers, after purification by column chromatography (60% EtOAc/hexane) followed by pTLC (50% EtOAc/CHCl$_3$) and recrystalisation from EtOAc and hexane. $^1$H NMR (300 MHz, CDCl$_3$) δ 7.83-7.79 (m, 2H), 7.30-7.26 (m, 2H), 4.74 (brs, 2H), 3.03-2.78 (m, 3H), 2.21-2.13 (m, 1H), 2.00-1.89 (m, 1H), 1.80-1.26 (m, 11H), 0.82-0.81 (m, 3H). ESIMS m/z [M+H]$^+$ 373.3.

Pharmacology

Example P1: CellLux Fluorescence Assay to Detect Agonists and Positive Allosteric Modulators of α7 nAChR Compounds were screened for positive allosteric modulation (PAM) of α7 nACh receptors on the CellLux (Perkin Elmer) with a fluorescence-based calcium assay. Activation of the α7 nAChR by endogenous ligands, results in a calcium flux which can be measured using ion specific fluorescent dyes. The fluorescence assay was run in a high throughput format on the CellLux, an automated fluorescent plate reader with liquid handling capabilities. The assay measured intracellular calcium changes in a GH4C1 cell line stably expressing α7 nAChRs, when treated with compounds that positively modulated an ACh-induced response. Compound was added first to identify any agonist activity followed by ACh addition (EC20 concentration) to measure PAM activity.

Prior to assay, α7/GH4C1 cells were seeded in 96-well plates (PDL-coated) and incubated for 48 hours at 33° C. in 5% CO$_2$. The cells were grown in F10Ham media plus 15% horse serum, 2.5% FCS, 2 mM penicillin, 2 mM streptomycin, 2 mM glutamine and 10 mM Hepes (Invitrogen). 0.5 mM sodium butyrate, a growth arrestor, was added to the cells during the incubation period to increase expression of α7 nAChR. On the day of assessment, the media was removed and the cells were washed with HBSS buffer (1 mM CaCl$_2$, 0.5 mM MgCl$_2$, 0.4 mM MgSO$_4$, 5 mM KCL, 0.4 mM KHPO$_4$, 4 mM NaHCO$_3$, 137 mM NaCl, 0.3 mM Na$_2$HPO$_4$, 5.5 mM glucose and 1M Hepes, pH7.4) and then Fluo-4 Direct Calcium dye (Molecular Probes; Excitation: 495 nm; Emission: 516 nm) was added. The cells were incubated with dye for 30 minutes at 33° C. Compound addition, ACh addition and fluorescence measurements were performed on the CellLux.

The CellLux recorded fluorescent responses at 5 second intervals starting with a 10 second baseline reading, the compound was then added and the response was read for 1 minute. ACh was then added and the response read for a further 2 minutes, a total of 4 minutes. This protocol detects agonist and PAM activity of compounds at the α7 nAChR.

Compounds were tested at 6 doses, in triplicate, 0.03, 0.1, 0.3, 1, 3 and 10 uM. Working stocks were prepared in DMSO from 10 mM DMSO stocks and then 10× starting stocks were prepared by diluting 1:100 in HBSS buffer (0.1% DMSO final). A 10× starting dilution of an EC20 concentration of ACh was prepared in HBSS buffer (0.1% DMSO final). Negative control was HBSS buffer (0.1% DMSO final).

Data was analysed by calculating % potentiation of compound compared to the ACh control response, where ACh potentiation was set at 0%. Peak/base values were calculated for each compound concentration (n=3) using AssayPro program (CellLux) and these values were used to determine % potentiation based on the ACh control peak/base value. Compounds were identified as active if they showed statistically significant potentiation of the control ACh response. For active compounds % potentiation values were used to calculate compound EC50 values in GraphPad Prism 4.

Example P2: Electrophysiology Protocol to Detect α7 nAChR Positive Allosteric Modulator Activity Compound Preparation:

Tested compounds were prepared by serial dilutions of 10 mM stock solution in DMSO to concentrations of the compound 1000 times higher than its final concentration. The DMSO stock solutions were then diluted 1:100 in the recording buffer bringing DMSO concentration to 1%. These intermediate solutions were further diluted 10 times with buffer to obtain final concentrations and lower DMSO concentration to 0.1%.

Acetylcholine chloride (ACh) purchased from Sigma-Aldrich (Sigma-Aldrich, St Louis, Mo.) was used as an α7 nAChR agonist at a concentration corresponding to EC$_{20}$ measured by peak current.

Calculation of the Effect on α7 nAChR-Mediated Currents:

The effect of tested compounds on ACh-evoked currents was calculated by the following formula:

$$\text{Effect (\%)} = \left(\left(\frac{I_{compound}}{I_{control}}\right) - 1\right) \times 100$$

Therefore, zero indicates no effect, negative numbers correspond to percentage of inhibition and positive numbers to percentage of potentiation relative to control ACh responses at EC$_{20}$.

The formula was used for calculations of effects on both peak current and area under curve (AUC).

Example P2.1: Automated Planar Patch-Clamp

Compounds of the invention may be evaluated by electrophysiology using a Patchliner® (Nanion Technologies GmbH, Germany), an automated planar patch-clamp platform of medium throughput was used as a first step in electrophysiological assessment of α7 nAChR positive allosteric modulators (PAMs).

Briefly, intracellular (KCl—50 mM, NaCl—10 mM, KF—60 mM, EGTA—20 mM, HEPES—10 mM, pH—7.2, 285 mOsmol) and extracellular (NaCl—140 mM, KCl—4 mM, CaCl$_2$—2 mM, MgCl$_2$—1 mM, HEPES—10 mM, D-Glucose—5 mM, pH—7.4, 298 mOsmol) solutions were automatically pipetted onto NPC-16 chip (medium resistance ~2.5-2.6 MΩ). Suspension of GH4C1 cells expressing rat α7 nAChRs was introduced in 4 wells of a medium resistance chip and suction was applied to attract cells in the holes. The extracellular solution was subsequently exchanged to high calcium solution (NaCl—80 mM, KCl—3 mM, CaCl$_2$—45 mM, HEPES—10 mM, pH—7.4, 298 mOsmol) followed by gigaohm seal formation and obtaining whole-cell configuration. The rest of protocol was carried out in the high-calcium recording solution. Holding potential was −70 mV throughout the protocol. A control response to 60 or 100 μM of ACh was obtained first. Next, a cell was pre-incubated with compound of interest at 3 μM for ~30 s after which the compound was co-applied with acetylcholine.

Amplitude of the responses was measured in HEKA Patchmaster software (HEKA Elektronik, Germany) and percentage of potentiation calculated. Recording was repeated unless a minimum of two replicates had been obtained per compound.

Example P2.2: Manual Patch Clamp

Compound of the invention may be evaluated by electrophysiology on a manual patch-clamp setup using a fast-application add-on Dynaflow® (Cellectricon AB, Sweden). The fast application system allows resolution of true peak amplitudes, which otherwise would be affected by rapid receptor desensitization, and thus greatly improves measurement precision with fast ligand gated channels such as α7 nAChR.

GH4C1 cells expressing rat α7 nAChRs were patch-clamped in the recording chamber of 16-channel re-usable Dynaflow® ReSolve chips using EPC10 USB amplifier (HEKA Elektronik, Germany). Extracellular solution contained NaCl—137 mM, KCl—5 mM, $CaCl_2$—2.5 mM, $MgCl_2$—1 mM, HEPES—10 mM, D-Glucose—10 mM, pH—7.4. Thin wall borosilicate glass electrodes (Harvard Apparatus) were pulled to a resistance of 2-4 MΩ when filled with intracellular solution ($K^+$-gluconate—120 mM, KCl—5 mM, HEPES—10 mM, EGTA—10 mM, $MgCl_2$—1 mM, ATP—2 mM, pH—7.2). Cells were held at −70 mV. Cells with series resistance below 15 MΩ were kept and 40% compensation was utilized routinely.

The recording protocol consisted of obtaining of two control ACh responses ($EC_{20}$, peak, 250 ms pulse) prior to 30 s pre-incubation with a tested compound (3 µM) followed by 250 MS co-application of 3 µM compound plus $EC_{20}$ ACh. Dose-responses for selected compounds were obtained by a continuous compound application of increasing concentrations alternated with co-applications of compound plus $EC_{20}$ ACh every 30 seconds.

Current amplitudes along with net charge carried (area under curve, AUC) were measured in Patchmaster software (HEKA Elektronik, Germany) and percentage of peak current and AUC potentiation by test compounds was calculated using the above mentioned formula. Dose-responses for selected compounds were fitted and plotted in Prism4/5 (GraphPad Software, Inc., CA).

Example P3: Animal Model of Cognitive Enhancement—T-Maze Continuous Alternation Task (T-CAT)—Mouse The cognition enhancing properties of the compounds in the invention were evaluated in an animal model where cognitive impairment is pharmacologically induced by Scopolamine, a muscarinic receptor antagonist which is used as a standard/reference drug for inducing cognitive deficits in healthy humans and animals.

The T-maze Continuous Alternation Task (T-CAT) measures spontaneous alternation, which is the innate tendency of mice to alternate free choices in a T-maze over a series of successive runs. This sequential procedure relies on working memory and is sensitive to various pharmacological manipulations affecting memory processes.

The T-maze apparatus is made of gray Plexiglas with a main stem (55 cm long×10 cm wide×25 cm high) and two arms (30 cm long×10 cm wide×25 cm high) positioned at 90 degree angle relative to the main stem. A start box (15 cm long×10 cm wide) is separated from the main stem by a sliding door. Sliding doors are also provided to close specific arms during the forced-choice alternation task.

The experimental protocol consists of one single session, which starts with 1 "forced-choice" trial, followed by 14 "free-choice" trials. In the first "forced-choice" trial, the animal is confined for 5 s in the start arm and then it is released while either the left or right goal arm is blocked by a sliding door. The animal will negotiate the maze, eventually enter the open goal arm, and return to the start position. Immediately after the return to the start position, the left or right goal door is opened and the animal is allowed to choose freely between the left and right goal arm ("free choice" trials). The animal is considered to have entered an arm when it places four paws in the arm. A session is terminated and the animal is removed from the maze as soon as 14 free-choice trials have been performed or 10 minutes have elapsed, whichever event occurs first. The percentage of alternation over the 14 free-choice trials is determined for each mouse and is used as an index of working memory performance. This percentage is defined as entry in a different arm of the T-maze over successive visits (i.e., left-right-left-right, etc).

Scopolamine administered 20 minutes prior the initiation of the T-maze session is used to induce disruption in the spontaneous alternation of mice. Test compounds are administered 60 minutes prior the start of the T-maze session in order to evaluate their ability to reverse the scopolamine effect.

The apparatus is cleaned between each animal using alcohol (70°). Urine and faeces are removed from the maze. During the trials, animal handling and the visibility of the operator are minimized as much as possible.

Example P4: Animal Model of Cognitive Enhancement—Novel Object Recognition Test—Rat The object recognition task is used to assess the short term memory in rats and is based on the natural tendency of rats to preferentially explore a novel versus a familiar object, which requires memory of the familiar object.

Equipment

The apparatus consists of an open acrylic glass cage (101 cm×101 cm; with 45 cm walls) within which animals can move freely. The two objects used in the assay are a metallic ball and a black box. The animal's approaches to the objects are recorded by an observer using stopwatch.

Methods

Step 1—Habituation:

Twenty four hours before the first trial, animals are allowed to habituate to the open-field apparatus for 15 minutes Step 2—Acquisition Trial:

One object (Object A) is placed in a particular corner of the central square. Animals are randomly exposed to the experimental situation for 10 minutes. Their explorative approaches to the object are recorded. Animals which don't display locomotor activity (total immobility) or do not explore the object are excluded.

Step 3—Retention Trial:

The test for retention is performed 30 minutes after the acquisition trial. Object A and the second object (Object B) are placed on adjacent corners of the central square. Each animal is exposed to the experimental situation for 10 minutes while exploratory approaches towards the two objects are recorded.

Step 4—Recognition Index:

For each animal, the time taken to explore object A (tA) and object B (tB) are recorded and the recognition index (RI)

determined using the formula: RI=tB/(tA+tB)×100 where tB is the time spent exploring Object B and tA is the time spent exploring object A, values which are collected during the retention trial. In addition, the results are also expressed as the difference between exploration time of the new and the familiar objects.

Drugs and Treatment Groups:

Each animal receives test substances or vehicle treatments at times shown below:

| Groups | Treatment | Time |
| --- | --- | --- |
| Control | vehicle (per os) | 1 hour before the acquisition trial |
| Scopolamine | 0.6 mg/kg (i.p.) | 20 min before the acquisition trial |
| Test Compounds | (dose) mg/kg (per os) | 1 hour before the acquisition trial |

Data Analysis

One-way analysis of variance (ANOVA) followed by Fishers Protected Least Significant Difference is used to compare pairs of group means. $p \leq 0.05$ are deemed significant.

Biological Data

Compounds shown in Table 1 were evaluated by automated planar patch clamp on the Patchliner® as described in Example P2.1. Table 1 shows the % effect on peak potentiation caused by 3 μM of compounds of the invention in the presence of acetylcholine. The compounds are designated either as Type I or Type II modulators based on the electrophysiology trace. Type 1 predominately affects the peak current. Type II modulators affect the peak current and also delay the desensitization of the receptor.

TABLE 1

| Example | Peak potentiation at 3 μM compound | Type I or Type II |
| --- | --- | --- |
| 1 | 5520% | II |
| 2 | 2999% | II |
| 3 | 969% | I |
| 4 | 7909% | II |
| 5 | 2566% | II |
| 6 | 506% | I |
| 7 | 134% | I |
| 8 | 9894% | II |
| 9 | 2101% | II |
| 10 | 2996% | II |
| 11 | 15% | II |
| 12 | 401% | I |
| 13 | 3124% | II |
| 14 | 1104% | II |
| 15 | 413% | I |
| 16 | 236% | I |
| 17 | 2862% | I |
| 18 | 2857% | I |
| 19 | 762% | I |
| 20 | 1072% | I |
| 21 | 14696% | II |
| 22 | 12311% | II |
| 23 | 8940% | II |
| 24 | 901% | II |
| 25 | 3409% | II |
| 26 | 455% | II |
| 27 | 4068% | I |
| 28 | 8167% | II |
| 29 | 456% | II |
| 30 | 419% | I |
| 31 | 17430% | II |
| 32 | 8931% | II |
| 33 | 1501% | II |
| 34 | 3661% | II |

TABLE 1-continued

| Example | Peak potentiation at 3 μM compound | Type I or Type II |
| --- | --- | --- |
| 35 | 57% | II |
| 36 | 125% | II |
| 37 | 9231% | II |
| 38 | 8655% | II |
| 39 | 5276% | II |
| 40 | 309% | II |
| 41 | 2437% | I |
| 42 | 2418% | II |
| 43 | 100% | I |
| 44 | 1813% | I |
| 45 | 2417% | I |
| 46 | 783% | I |
| 47 | 867% | I |
| 49 | 1450% | II |
| 50 | 8167% | II |
| 51 | 171% | I |
| 52 | 3068% | II |
| 53 | 4388% | II |
| 54 | 574% | I |
| 55 | 724% | I |
| 56 | 131% | I |
| 57 | 473% | I |
| 58 | 17581% | II |
| 59 | 3158% | I |
| 62 | 38% | II |

Compounds shown in Table 2 showed a significant effect in the mouse T-maze Continuous Alternation Task as described in Example P3. The compounds were dosed orally at 10 mg/kg.

TABLE 2

| Example | T-maze % control at 10 mg/kg |
| --- | --- |
| 3 | 62 |
| 13 | 80 |
| 17 | 100 |
| 20 | 100 |
| 21 | 100 |
| 30 | 70 |
| 50 | 77 |
| 51 | 81 |

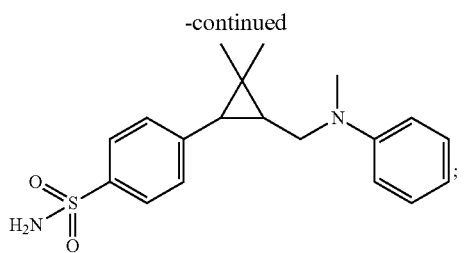
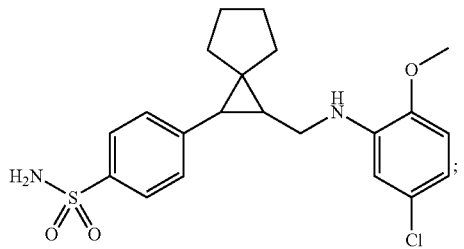
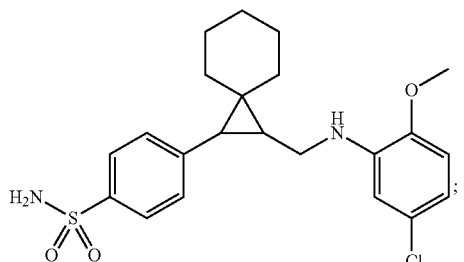
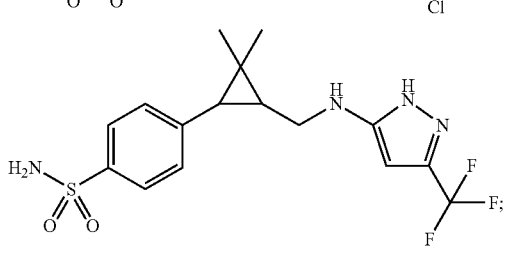
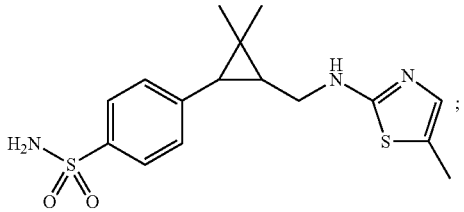
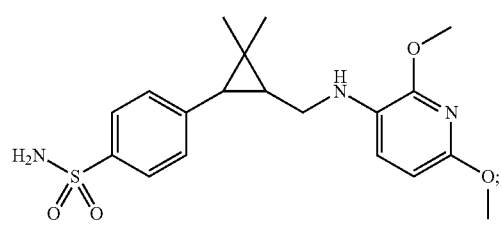

119
-continued
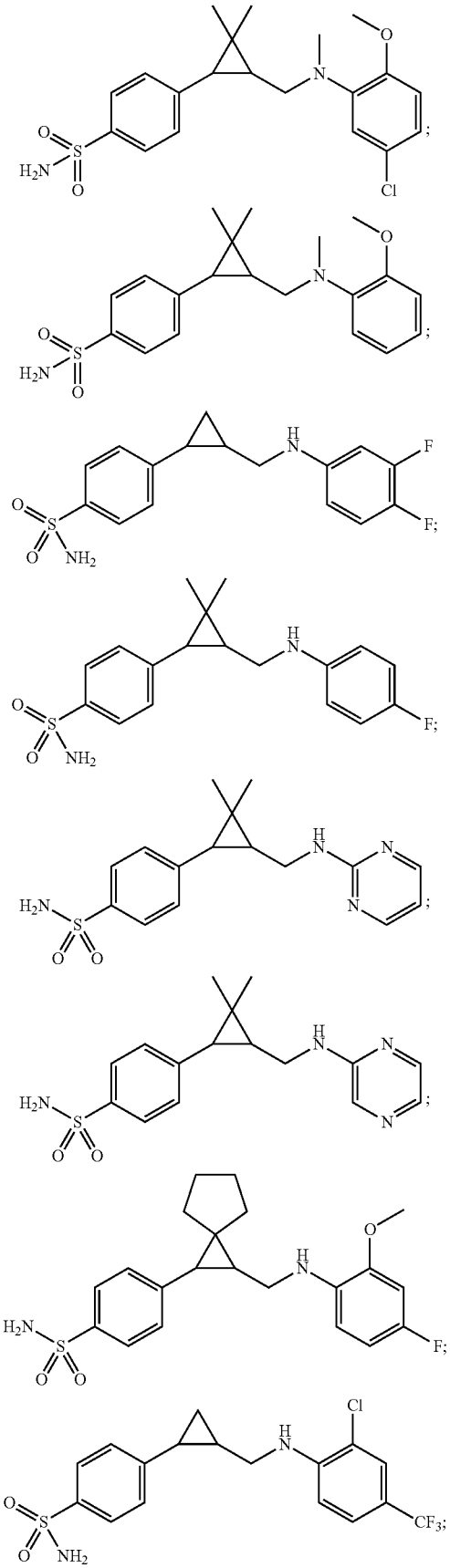
120
-continued
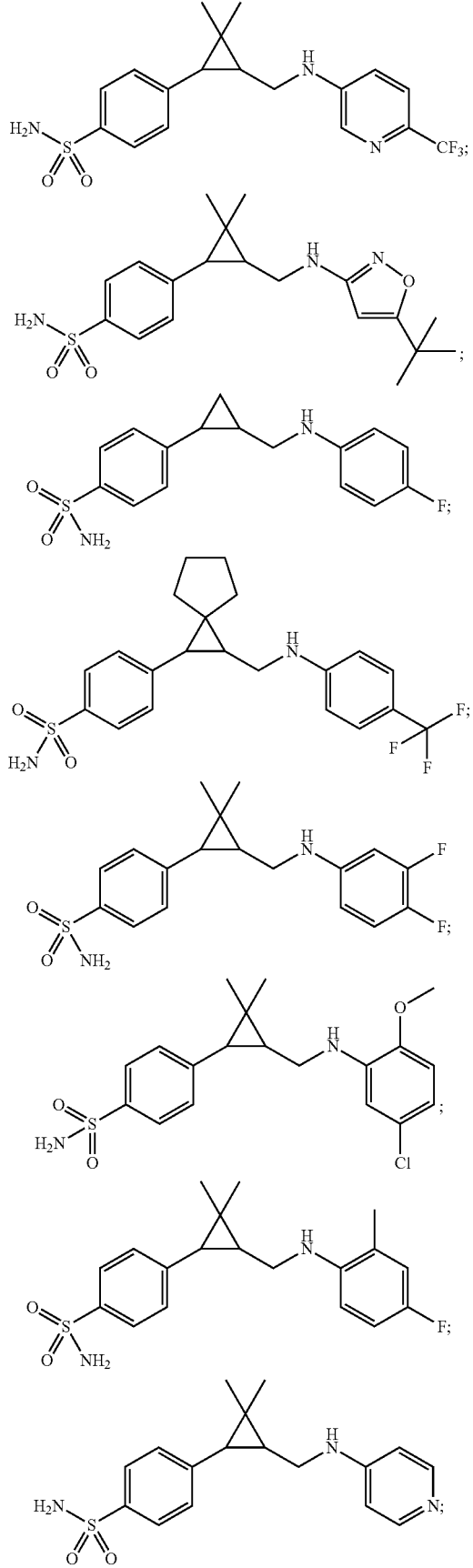

-continued
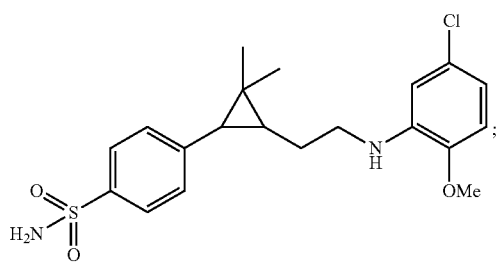
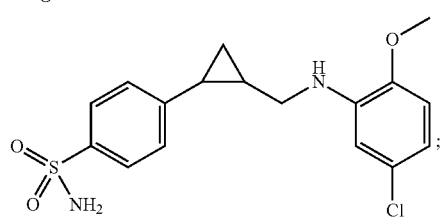
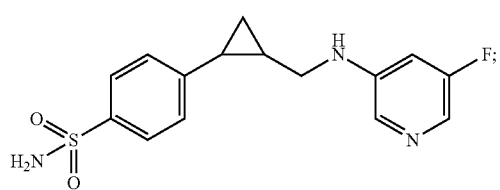
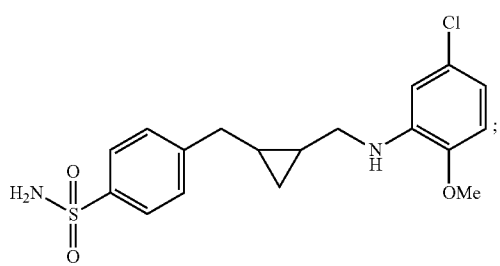
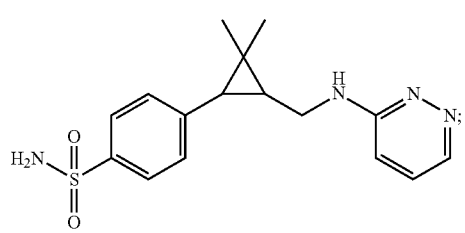
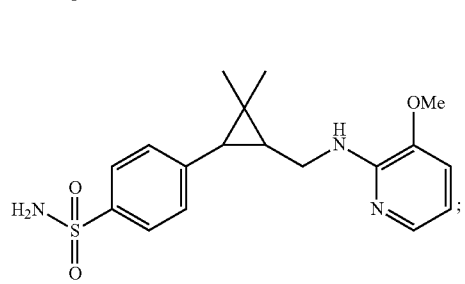
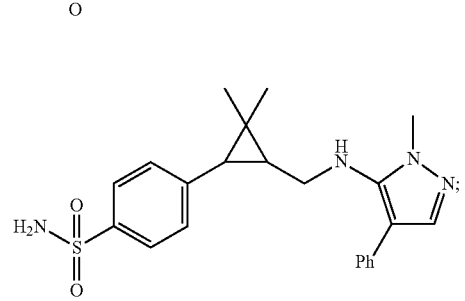
-continued
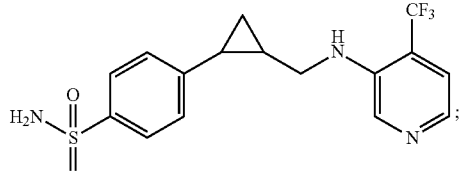
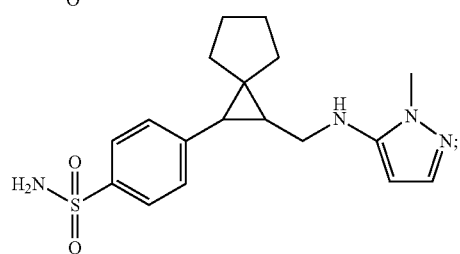
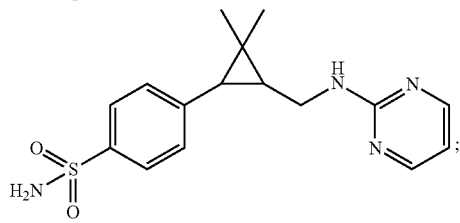
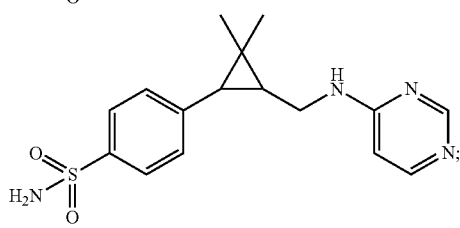
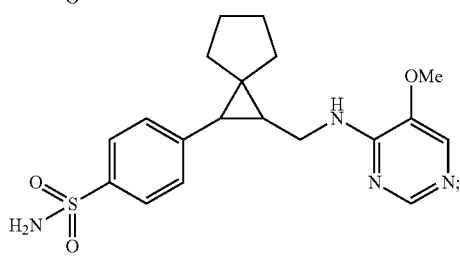
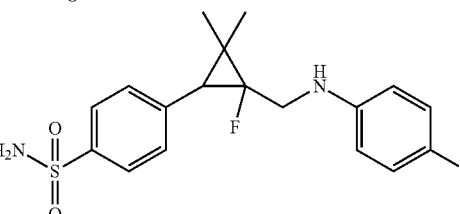
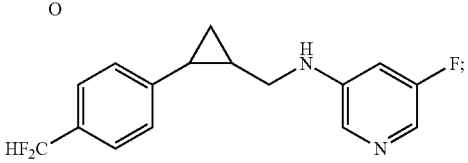
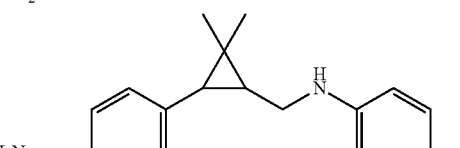

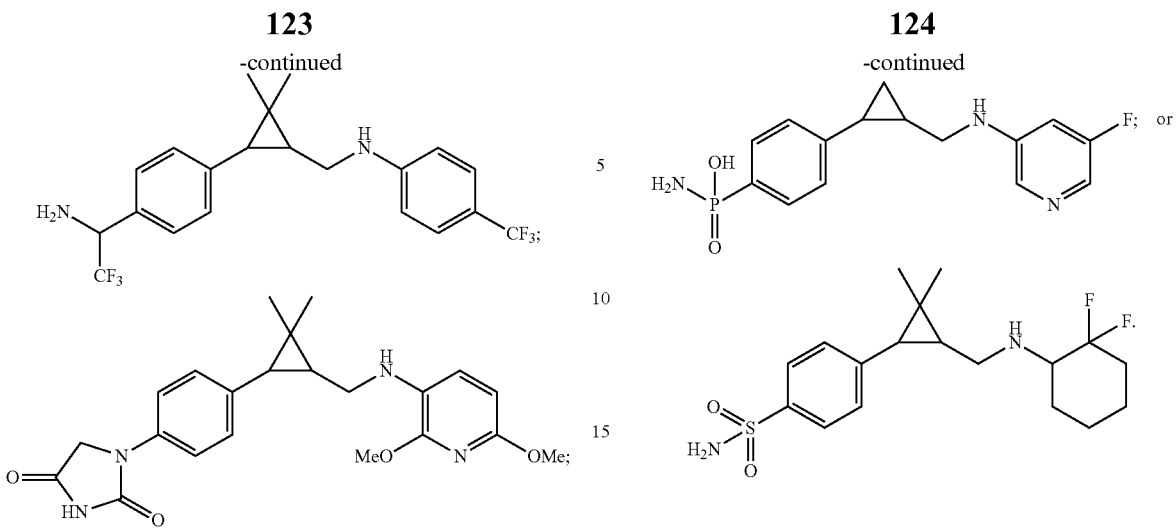

The invention claimed is:

1. A compound represented by formula (Ia'), or a pharmaceutically acceptable salt thereof:

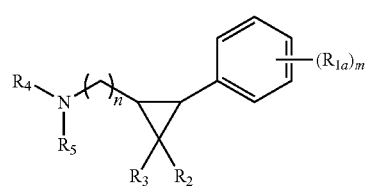

(Ia')

wherein n is 1;

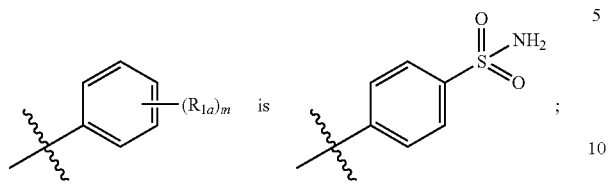 is $R_2$ is selected from $C_1$-$C_4$ alkyl, $C_1$-$C_4$ haloalkyl, phenyl, F, or Cl;

$R_3$ is selected from hydrogen, $C_1$-$C_4$ alkyl, $C_1$-$C_4$ haloalkyl, F, Cl, or CN; or $R_2$ and $R_3$ together form $C_{4-9}$ cycloalkyl or $C_{4-9}$ cycloalkenyl;

$R_4$ is selected from optionally substituted heteroaryl, optionally substituted heterocyclyl, or optionally substituted aryl; and $R_5$ is independently selected from hydrogen, or $C_1$-$C_4$ alkyl;

wherein the optional substituents are each independently selected from halogen, $C_{1-6}$ alkyl, $C_{1-6}$alkoxy, $C_{2-6}$ alkenyl, $C_{2-6}$ alkynyl, $C_{1-6}$haloalkyl, $C_{1-6}$ haloalkoxy, —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —P=O(OH)NH$_2$, —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''', and —S(O)$_2$R'''', wherein R''' is lower alkyl or cycloalkyl and wherein R'''' is lower alkyl, cycloalkyl or OH.

2. A compound according to claim 1, or a pharmaceutically acceptable salt thereof, wherein $R_2$ and $R_3$ are both $C_1$-$C_3$ alkyl (preferably methyl), or $R_2$ and $R_3$ together form a $C_4$-$C_9$ cycloalkyl ring.

3. A compound according to claim 1 or a pharmaceutically acceptable salt thereof, wherein $R_2$ and $R_3$ are both F.

4. A compound according to claim 1 or a pharmaceutically acceptable salt thereof, wherein $R_2$ and $R_3$ are both methyl.

5. A compound according to claim 1 or a pharmaceutically acceptable salt thereof, wherein $R_2$ is methyl, and $R_3$ is hydrogen.

6. A compound according to claim 1 or a pharmaceutically acceptable salt thereof, wherein $R_2$ and $R_3$ together form a $C_4$-$C_9$ cycloalkyl ring, preferably cyclopentyl or cyclohexyl ring.

7. A compound or stereoisomer thereof, or a pharmaceutically acceptable salt thereof, represented by the following:

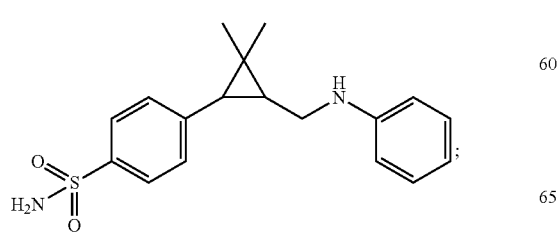

-continued